United States Patent
Srivastava et al.

(10) Patent No.: US 12,065,467 B2
(45) Date of Patent: *Aug. 20, 2024

(54) HIGH-TRANSDUCTION-EFFICIENCY rAAV VECTORS, COMPOSITIONS, AND METHODS OF USE

(71) Applicant: University of Florida Research Foundation, Incorporated, Gainesville, FL (US)

(72) Inventors: Arun Srivastava, Gainesville, FL (US); George Vladimirovich Aslanidi, Gainesville, FL (US); Kim M. Van Vliet, Gainesville, FL (US); Mavis Agbandje-McKenna, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/810,729

(22) Filed: Jul. 5, 2022

(65) Prior Publication Data
US 2023/0129762 A1   Apr. 27, 2023

Related U.S. Application Data

(60) Continuation of application No. 16/283,705, filed on Feb. 22, 2019, now Pat. No. 11,434,260, which is a
(Continued)

(51) Int. Cl.
*C12N 7/00* (2006.01)
*C07K 14/005* (2006.01)
*C12N 15/86* (2006.01)

(52) U.S. Cl.
CPC ............ *C07K 14/005* (2013.01); *C12N 15/86* (2013.01); *C12N 2750/14122* (2013.01); *C12N 2750/14143* (2013.01); *C12N 2750/14145* (2013.01)

(58) Field of Classification Search
None
See application file for complete search history.

(56) References Cited

U.S. PATENT DOCUMENTS

| | | | |
|---|---|---|---|
| 6,156,303 A | 12/2000 | Russell et al. | |
| 6,491,907 B1 | 12/2002 | Rabinowitz et al. | |

(Continued)

FOREIGN PATENT DOCUMENTS

| | | |
|---|---|---|
| CA | 2720097 A1 | 10/2008 |
| CA | 2826273 A1 | 8/2012 |

(Continued)

OTHER PUBLICATIONS

Bartel et al., "Enhancing the clinical potential of AAV vectors by capsid engineering to evade pre-existing immunity," Frontiers in Microbiology, vol. 2, Article 204: 1-10 (Year: 2011).*

(Continued)

*Primary Examiner* — M Franco G Salvoza
(74) *Attorney, Agent, or Firm* — Wolf, Greenfield & Sacks, P.C.

(57) ABSTRACT

The present invention provides AAV capsid proteins comprising modification of one or a combination of the surface-exposed lysine, serine, threonine and/or tyrosine residues in the VP3 region. Also provided are rAAV virions comprising the AAV capsid proteins of the present invention, as well as nucleic acid molecules and rAAV vectors encoding the AAV capsid proteins of the present invention. Advantageously, the rAAV vectors and virions of the present invention have improved efficiency in transduction of a variety of cells, (Continued)

tissues and organs of interest, when compared to wild-type rAAV vectors and virions.

21 Claims, 47 Drawing Sheets

Specification includes a Sequence Listing.

Related U.S. Application Data division of application No. 15/444,235, filed on Feb. 27, 2017, now Pat. No. 10,294,281, which is a division of application No. 14/401,442, filed as application No. PCT/US2013/041234 on May 15, 2013, now Pat. No. 9,611,302, which is a continuation-in-part of application No. 13/840,224, filed on Mar. 15, 2013, now Pat. No. 9,725,485.

(60) Provisional application No. 61/647,318, filed on May 15, 2012.

(56) References Cited

U.S. PATENT DOCUMENTS

| | | | |
|---|---|---|---|
| 7,052,692 | B1 | 5/2006 | Srivastava et al. |
| 8,445,267 | B2 | 5/2013 | Zhong et al. |
| 8,802,440 | B2 | 8/2014 | Zhong et al. |
| 9,157,098 | B2 | 10/2015 | Zhong et al. |
| 9,611,302 | B2 | 4/2017 | Srivastava et al. |
| 9,725,485 | B2 | 8/2017 | Srivastava et al. |
| 9,775,918 | B2 | 10/2017 | Zhong et al. |
| 9,920,097 | B2 | 3/2018 | Zhong et al. |
| 10,011,640 | B2 | 7/2018 | Srivastava et al. |
| 10,294,281 | B2 | 5/2019 | Srivastava et al. |
| 10,308,957 | B2 | 6/2019 | Boye et al. |
| 10,426,844 | B2 | 10/2019 | Agbandje-McKenna et al. |
| 10,648,000 | B2 | 5/2020 | Hauswirth et al. |
| 10,723,768 | B2 | 7/2020 | Zhong et al. |
| 10,793,606 | B2 | 10/2020 | Zolotukhin et al. |
| 10,815,279 | B2 | 10/2020 | Srivastava et al. |
| 10,927,150 | B2 | 2/2021 | Aslanidi et al. |
| 10,934,327 | B2 | 3/2021 | Srivastava et al. |
| 11,124,544 | B2 | 9/2021 | Srivastava et al. |
| 11,332,502 | B2 | 5/2022 | Zolotukhin et al. |
| 11,434,260 | B2 | 9/2022 | Srivastava et al. |
| 2003/0138772 | A1 | 7/2003 | Gao et al. |
| 2003/0219733 | A1 | 11/2003 | Clark et al. |
| 2006/0088936 | A1 | 4/2006 | Warrington et al. |
| 2006/0292117 | A1 | 12/2006 | Loiler et al. |
| 2009/0197338 | A1 | 8/2009 | Vandenberghe et al. |
| 2010/0104561 | A1 | 4/2010 | Zhong et al. |
| 2013/0203841 | A1 | 8/2013 | Zhong et al. |
| 2013/0216501 | A1 | 8/2013 | Zhong et al. |
| 2013/0224836 | A1 | 8/2013 | Muramatsu |
| 2013/0310443 | A1 | 11/2013 | Srivastava et al. |
| 2014/0050701 | A1 | 2/2014 | Zhong et al. |
| 2014/0341852 | A1 | 11/2014 | Srivastava et al. |
| 2015/0133530 | A1 | 5/2015 | Srivastava et al. |
| 2016/0106865 | A1 | 4/2016 | Zhong et al. |
| 2016/0333372 | A1 | 11/2016 | Srivastava et al. |
| 2016/0361439 | A1 | 12/2016 | Agbandje-McKenna et al. |
| 2016/0369299 | A1 | 12/2016 | Boye et al. |
| 2017/0275337 | A1 | 9/2017 | Srivastava et al. |
| 2017/0356009 | A1 | 12/2017 | Lu et al. |
| 2018/0030096 | A1 | 2/2018 | Aslanidi et al. |
| 2018/0036428 | A1 | 2/2018 | Zhong et al. |
| 2018/0105559 | A1 | 4/2018 | Zhong et al. |
| 2018/0135074 | A1 | 5/2018 | Srivastava et al. |
| 2018/0193489 | A1 | 7/2018 | Hobbs et al. |
| 2018/0223312 | A1 | 8/2018 | Srivastava et al. |
| 2018/0244727 | A1 | 8/2018 | Zhong et al. |
| 2019/0000943 | A1 | 1/2019 | Aslanidi |
| 2019/0016759 | A1 | 1/2019 | Srivastava et al. |
| 2019/0127424 | A1 | 5/2019 | Srivastava et al. |
| 2019/0284244 | A1 | 9/2019 | Srivastava et al. |
| 2020/0010510 | A1 | 1/2020 | Aslanidi et al. |
| 2020/0093938 | A1 | 3/2020 | Pan et al. |
| 2021/0040156 | A1 | 2/2021 | Zhong et al. |
| 2021/0253644 | A1 | 8/2021 | Srivastava et al. |
| 2021/0269487 | A1 | 9/2021 | Aslanidi et al. |
| 2022/0347317 | A1 | 11/2022 | Srivastava et al. |
| 2023/0136849 | A1 | 5/2023 | Srivastava et al. |

FOREIGN PATENT DOCUMENTS

| | | | | |
|---|---|---|---|---|
| CN | 102159713 | A | 8/2011 | |
| CN | 102994549 | A | 3/2013 | |
| CN | 103060331 | A | 4/2013 | |
| CN | 104470945 | A | 3/2015 | |
| EP | 1310571 | A2 | 5/2003 | |
| EP | 1486567 | A1 | 12/2004 | |
| EP | 2660325 | A2 | 11/2013 | |
| JP | 2002/538770 | A | 11/2002 | |
| JP | 7004328 | B2 | 2/2022 | |
| WO | WO 2000/65038 | A2 | 11/2000 | |
| WO | WO 2001/83692 | A2 | 11/2001 | |
| WO | WO 2003/006616 | A2 | 1/2003 | |
| WO | WO 2003/052052 | A2 | 6/2003 | |
| WO | WO 2004/027019 | A2 | 4/2004 | |
| WO | WO 2004/111248 | A2 | 12/2004 | |
| WO | WO-2004112727 | A2 * | 12/2004 | ......... A61K 38/4846 |
| WO | WO 2005/033321 | A2 | 4/2005 | |
| WO | WO 2006/110689 | A2 | 10/2006 | |
| WO | WO 2006/119150 | A2 | 11/2006 | |
| WO | WO 2008/124724 | A1 | 10/2008 | |
| WO | WO 2008/145400 | A2 | 12/2008 | |
| WO | WO 2009/154452 | A1 | 12/2009 | |
| WO | WO 2011/133890 | A1 | 10/2011 | |
| WO | WO 2012/057363 | A2 | 5/2012 | |
| WO | WO 2013/158879 | A1 | 10/2013 | |
| WO | WO 2013/173512 | A1 | 11/2013 | |
| WO | WO 2014/193716 | A1 | 12/2014 | |
| WO | WO 2016/126857 | A1 | 8/2016 | |

OTHER PUBLICATIONS

NCBI Blast alignment of SEQ ID No. 13 and instant SEQ ID No. 2 (Year: 2023).*
Examination Report dated Oct. 22, 2013, issued in CIPO 2,720,097 (2 pages).
EP Examination Report dated Jan. 27, 2011, issued in EP 08733161. 7-2405 (3 pages).
Response to EP Examination Report dated Jul. 25, 2011, issued in EP 08733161.7-2405 (8 pages).
Extended European Search Report for Application No. EP 18201865.5 mailed Feb. 27, 2019.
International Search Report and Written Opinion for Application No. PCT/US2008/059647 mailed Sep. 10, 2008.
International Preliminary Report on Patentability for Application No. PCT/US2008/059647 mailed Oct. 22, 2009.
Partial European Search Report for Application No. EP 20210108.5 mailed Jun. 2, 2021.
Extended European Search Report for Application No. EP 20210108.5 mailed Sep. 13, 2021.
International Search Report and Written Opinion for Application No. PCT/US2013/041234 mailed Feb. 13, 2014.
International Preliminary Report on Patentability for Application No. PCT/US2013/041234 mailed Nov. 27, 2014.
Partial European Search Report for Application EP 18202680.7 mailed Apr. 29, 2019.
Extended European Search Report for Application No. EP 18202680.7 mailed Jul. 31, 2019.
International Search Report and Written Opinion for Application No. PCT/US2014/039015 mailed Nov. 24, 2014.
International Preliminary Report on Patentability for Application No. PCT/US2014/039015 mailed Dec. 3, 2015.
International Search Report and Written Opinion for Application No. PCT/US2016/016422 mailed May 5, 2016.

(56) References Cited

OTHER PUBLICATIONS

International Preliminary Report on Patentability for Application No. PCT/US2016/016422 mailed Aug. 17, 2017.
Invitation to Pay Additional Fees for Application No. PCT/US2022/025916, mailed Oct. 19, 2022.
[No Author Listed] Database UniProt KB, Accession B4Y866 (B4Y886_9VIRU9), Integrated into UniProt KB/TrEMBL Sep. 23, 2008, Last modified Jul. 31, 2019. 4 pages.
[No Author Listed] Database UniProt KB, Accession Q808W7 (Q808W7-9VIRU), Integrated into UniProt KB/TrEMBL Jun. 1, 2003, Last modified Jul. 31, 2019. 4 pages.
[No Author Listed] Database UnitprotKB, Accession No. Q9YIJ1 (Q9YIJ1_9VIRU), Integrated into UniProt KB/TrEMBL May 1, 2009, Last modified Jun. 2, 2021.
[No Author Listed] NCBI Blast Alignment of instant SEQ ID No. 1 and SEQ ID No. 1 of 10815279 (Year: 2022).
[No Author Listed] NCBI Blast Alignment of instant SEQ ID No. 1 and SEQ ID No. 1 of Zhong et al. (Year: 2022).
[No Author Listed] NCBI Blast Alignment of instant SEQ ID No. 1 and SEQ ID No. 6 of 10011640 (Year: 2022).
[No Author Listed] NCBI Blast Alignment of instant SEQ ID No. 1 and SEQ ID No. 6 of 9920097 (Year: 2022).
[No Author Listed], Genbank Submission; NIH/NCBI Accession No. YP_680426. Major coat protein VP1 [Adeno-associated virus]. Jul. 25, 2006.
Asher et al., Clinical development on the frontier: gene therapy for duchenne muscular dystrophy. Expert Opin Biol Ther. Mar. 2020;20(3):263-274. doi: 10.1080/14712598.2020.1725469. Epub Feb. 12, 2020.
Aslanidi et al., High-efficiency transduction of human monocyte-derived dendritic cells by capsid-modified recombinant AAV2 vectors. Vaccine. Jun. 6, 2012;30(26):3908-17. doi: 10.1016/j.vaccine.2012.03.079. Epub Apr. 10, 2012.
Aslanidi et al., Optimization of the capsid of recombinant adeno-associated virus 2 (AAV2) vectors: the final threshold? PLoS One. 2013;8(3):e59142. doi: 10.1371/journal.pone.0059142. Epub Mar. 19, 2013.
Aslanidi et al., Abstract 116. Site-directed mutagenesis of surface-exposed tyrosine, serine, and threonine residues leads to high-efficiency transduction by recombinant adeno-associated virus 2 vectors. Mol Ther. 2012;20(Supp. 1):S48.
Aslanidi et al., Abstract 333: High-Efficiency Transduction of Primary Human Monocyte-Derived Dendritic Cells by Recombinant AAV6 Vectors Containing Mutations in Surface-Exposed Serine and Threonine Residues. Molecular Therapy. 2013;21(Supp. 1):S129.
Aslanidi et al., Abstract 334: Optimization of the capsid of recombinant adeno-associated virus 2 (AAV2) vectors: the final threshold? Molecular Therapy. 2013;21(Supp. 1):S129.
Aslanidi et al., Abstract 368. High-Efficiency transduction of primary human monocyte-derived dendritic cells by recombinant adeno-associated virus 2 vectors containing mutations in surface-exposed serine and threonine residues. Mol Ther. 2012;20(Supp. 1):S144.
Aslanidi et al., Abstract C240: Modification on the capsid of recombinant adeno-associated virus vectors (rAAV) leads to high-efficiency transduction of human monocyte-derived dendritic cells (moDCs). Mol Cancer Ther. Nov. 2011. 10(11): Abstract C240. 3 Pages.
Asokan et al., The AAV vector toolkit: poised at the clinical crossroads. Mol Ther. Apr. 2012;20(4):699-708. doi: 10.1038/mt.2011.287. Epub Jan. 24, 2012.
Auricchio et al., Exchange of surface proteins impacts on viral vector cellular specificity and transduction characteristics: the retina as a model. Hum Mol Genet. Dec. 15, 2001;10(26):3075-81. doi: 10.1093/hmg/10.26.3075.
Bantel-Schaal et al., Human adeno-associated virus type 5 is only distantly related to other known primate helper-dependent parvoviruses. J Virol. Feb. 1999;73(2):939-47.
Cheng et al., Development of optimized AAV3 serotype vectors: mechanism of high-efficiency transduction of human liver cancer cells. Gene Ther. Apr. 2012;19(4):375-84. doi: 10.1038/gt.2011.105. Epub Jul. 21, 2011. Author Manuscript, 24 pages.
Chiorini et al., Capsid Protein [Adeno-associated virus-5] Genbank Accession No. YP-068409 Dec. 8, 2008. 2 pages.
Dalkara et al., Enhanced gene delivery to the neonatal retina through systemic administration of tyrosine-mutated AAV9. Gene Ther. Feb. 2012;19(2):176-81. doi: 10.1038/gt.2011.163. Epub Oct. 20, 2011.
De Oliveira et al., Herpes simplex virus type 1/adeno-associated virus hybrid vectors. Open Virol J. Jun. 18, 2010;4:109-22. doi: 10.2174/1874357901004030109.
Doroudchi et al., Virally delivered channelrhodopsin-2 safely and effectively restores visual function in multiple mouse models of blindness. Mol Ther. Jul. 2011;19(7):1220-9. doi: 10.1038/mt.2011.69. Epub Apr. 19, 2011.
Duan et al., Enhancement of muscle gene delivery with pseudotyped adeno-associated virus type 5 correlates with myoblast differentiation. J Virol. Aug. 2001;75(16):7662-71. doi: 10.1128/JVI.75.16.7662-7671.2001.
Endell, Generation of enhanced gene delivery vectors by directed evolution of adeno-associated virus. Dissertation, LMU Munchen: Faculty of Chemistry and Pharmacy. 2006, 126 pages.
Gabriel et al., Bioengineering of AAV2 capsid at specific serine, threonine, or lysine residues improves its transduction efficiency in vitro and in vivo. Hum Gene Ther Methods. Apr. 2013;24(2):80-93. doi: 10.1089/hgtb.2012.194. Epub Mar. 15, 2013.
Gabriel et al., Targeted Mutagenesis of Ubiquitin-Binding Lysine Residues on the Adeno-Associated Virus (AAV)2 Capsid Improves Its Transduction Efficiency. Mol Ther. 2012;20(Supp. 1):S146.
Gao et al., Clades of Adeno-associated viruses are widely disseminated in human tissues. J Virol. Jun. 2004;78(12):6381-8.
Gao et al., Novel adeno-associated viruses from rhesus monkeys as vectors for human gene therapy. Proc Natl Acad Sci U S A. Sep. 3, 2002;99(18):11854-9. Epub Aug. 21, 2002.
Genbank Accession No. AAC55049.1. capsid protein [Adeno-associated virus-3]. Muramatsu et al., Dated Jul. 14, 1996. 2 pgs.
Genbank Accession No. AAN03857.1. capsid protein [Adeno-associated virus-8]. Gao et al., Dated Sep. 5, 2002. 2 pgs.
Genbank Accession No. AAS99284.1 . capsid protein VP1 [Adeno-associated virus]. Gao et al., Dated Jun. 24, 2004. 2 pgs.
Glushakova et al., 459. High-Efficiency Transduction of Human Hepatoblastoma and Hepatocellular Carcinoma Cells by the Wild-Type and the Tyrosine-Mutant AAV3 Serotype Vectors. Mol Ther. 2009;17(Supp. 1):S179.
Grimm et al., Liver transduction with recombinant adeno-associated virus is primarily restricted by capsid serotype not vector genotype. J Virol. Jan. 2006;80(1):426-39. doi: 10.1128/JVI.80.1.426-439.2006.
Grimm et al., Titration of AAV-2 particles via a novel capsid ELISA: packaging of genomes can limit production of recombinant AAV-2. Gene Ther. Jul. 1999;6(7):1322-30. doi: 10.1038/sj.gt.3300946.
Halbert et al., Repeat transduction in the mouse lung by using adeno-associated virus vectors with different serotypes. J Virol. Feb. 2000;74(3):1524-32. doi: 10.1128/jvi.74.3.1524-1532.2000.
Hareendran et al., 115. Bio-Engineering of Adeno-Associated Virus Serotype (AAV)-2 Capsid at Serine/Threonine Residues Improves Its Transduction Efficiency Both In Vitro and In Vivo. Mol Ther. May 2012;20(S1):S47.
Horowitz et al., Tyrosine cross-linking reveals interfacial dynamics in adeno-associated viral capsids during infection. ACS Chemical Biology, pubs.acs.org/acschemicalbiology, ACS Publications, ACS Chem Biol. Jun. 15, 2012;7(6):1059-66. doi: 10.1021/cb3000265. Epub Apr. 6, 2012.
Jayandharan et al., 372. Human Hematopoietic Stem Cell Transduction by AAV Vectors: Identification of AAV6 as the Most Efficient Serotype, and Further Augmentation in Transduction Efficiency with Point-Mutations at Tyrosine Residues 705 and 731in the Viral Capsid. Mol Ther. 2009;17(Supp. 1):S145-6.
Jayandharan et al., Activation of the NF-kappaB pathway by adeno-associated virus (AAV) vectors and its implications in immune

(56) References Cited

OTHER PUBLICATIONS response and gene therapy. Proc Natl Acad Sci U S A. Mar. 1, 2011;108(9):3743-8. doi: 10.1073/pnas.1012753108. Epub Feb. 14, 2011.

Kauss et al., 457. Tyrosine-Modified rAAV2 Vectors Display Enhanced Transduction of Human Hematopoietic Stem Cells. Mol Ther. 2009;17(Supp. 1):S178.

Kauss et al., Enhanced long-term transduction and multilineage engraftment of human hematopoietic stem cells transduced with tyrosine-modified recombinant adeno-associated virus serotype 2. Hum Gene Ther. Sep. 2010;21(9):1129-36. doi: 10.1089/hum.2010.016.

Kay et al., Targeting photoreceptors via intravitreal delivery using novel, capsid-mutated AAV vectors. PLoS One. Apr. 26, 2013;8(4):e62097. doi: 10.1371/journal.pone.0062097. Print 2013.

Kern et al., Identification of a heparin-binding motif on adeno-associated virus type 2 capsids. J Virol. Oct. 2003;77(20):11072-81.

Ku et al., Gene therapy using self-complementary Y733F capsid mutant AAV2/8 restores vision in a model of early onset Leber congenital amaurosis. Hum Mol Genet. Dec. 1, 2011;20(23):4569-81. doi: 10.1093/hmg/ddr391. Epub Aug. 31, 2011.

Le Meur et al., Restoration of vision in RPE65-deficient Briard dogs using an AAV serotype 4 vector that specifically targets the retinal pigmented epithelium. Gene Therapy 14(4):292-303 (Feb. 2007), 12 pages.

Li et al., High-efficiency transduction of fibroblasts and mesenchymal stem cells by tyrosine-mutant AAV2 vectors for their potential use in cellular therapy. Hum Gene Ther. Nov. 2010;21(11):1527-43. doi: 10.1089/hum.2010.005. Epub Oct. 6, 2010.

Li et al., Site-Directed Mutagenesis of Surface-Exposed Lysine Residues Leads to Improved Transduction by AAV2, But Not AAV8, Vectors in Murine Hepatocytes In Vivo. Hum Gene Ther Methods. Dec. 2015;26(6):211-20. doi: 10.1089/hgtb.2015.115. Epub Oct. 27, 2015.

Li et al., Site-Directed Mutagenesis of Surface-Exposed Lysine Residues Leads to Improved Transduction by Recombinant Aav2 and Aav8 Vectors in Murine Hepatocytes in Vivo. Mol Ther. 2013;21(Supp 1):S208-9.

Li et al., The fecal viral flora of California sea lions. J Virol. Oct. 2011;85(19):9909-17. doi: 10.1128/JVI.05026-11. Epub Jul. 27, 2011.

Ling et al., Selective in vivo targeting of human liver tumors by optimized AAV3 vectors in a murine xenograft model. Hum Gene Ther. Dec. 2014;25(12):1023-34. doi: 10.1089/hum.2014.099.

Ling et al., Development of Optimized AAV Serotype Vectors for High-Efficiency Transduction at Further Reduced Doses. Hum Gene Ther Methods. Aug. 2016;27(4):143-9. doi: 10.1089/hgtb.2016.054.

Ling et al., Enhanced transgene expression from recombinant single-stranded D-sequence-substituted adeno-associated virus vectors in human cell lines in vitro and in murine hepatocytes in vivo. J Virol. Jan. 15, 2015;89(2):952-61. doi: 10.1128/JVI.02581-14. Epub Oct. 29, 2014.

Ling et al., The role of glucocorticoid receptor signaling in adeno-associated virus 2 infection. Molecular Therapy. 2016;24(Supp. 1):S6.

Lochrie et al., Mutations on the External Surfaces of Adeno-Associated Virus Type 2 Capsids That Affect Transduction and Neutralization. Journal of Virology 80(2):821-834 (Jan. 2006), 14 pages.

Locke et al., Transduction of Human Adipose-Derived Mesenchymal Stem Cells by Recombinant Adeno-Associated Virus Vectors. Copyrgt. Mary Ann Liebert, Inc., DOI: 10.1089/ten.tec.2011.0153, Tissue Engineering: Part C; vol. 17, No. 9,2011, pp. 949-959.

Maheshri et al., Directed evolution of adeno-associated virus yields enhanced gene delivery vectors. Nat Biotechnol. Feb. 2006;24(2):198-204. doi: 10.1038/nbt1182. Epub Jan. 22, 2006.

Markusic et al., 765. Novel AAV2 Tyrosine Mutant Capsids Provide Long-Term Therapeutic Factor IX Expression in a Difficult to Tolerize Murine Hemophilia Model. Mol Ther. 2009;17(Supp. 1):S292.

Markusic et al., High-Efficiency Transduction and Correction of Murine Hemophelia B Using AAV2 Vectors Devoid of Multiple Surface-Exposed Tyrosines. Molecular Therapy. Dec. 2010;18(12):2048-56. doi: 10.1038/mt.2010.172. Epub Aug. 24, 2010.

Martino et al., Engineered AAV vector minimizes in vivo targeting of transduced hepatocytes by capsid-specific CD8+ T cells. Blood. Mar. 21, 2013;121(12):2224-33. doi: 10.1182/blood-2012-10-460733. Epub Jan. 16, 2013.

McClements et al., Gene therapy for retinal disease. Transl Res. Apr. 2013;161(4):241-54. doi: 10.1016/j.trsl.2012.12.007. Epub Jan. 8, 2013. Author Manuscript, 23 pages.

Mendell et al., Assessment of Systemic Delivery of rAAVrh74.MHCK7.micro-dystrophin in Children With Duchenne Muscular Dystrophy: A Nonrandomized Controlled Trial. JAMA Neurol. Sep. 1, 2020;77(9):1122-1131. doi: 10.1001/jamaneurol.2020.1484.

Mori et al., Two novel adeno-associated viruses from cynomolgus monkey: pseudotyping characterization of capsid protein. Virology. Dec. 20, 2004;330(2):375-83.

Nelson et al., Lehninger Principles of Biochemistry. 2005. 4th edition. Chapter 3. Amino Acids, Peptides, and Proteins. W.H. Freeman and Company, New York: 75-115.

Opie et al., Identification of amino acid residues in the capsid proteins of adeno-associated virus type 2 that contribute to heparan sulfate proteoglycan binding. J Virol. Jun. 2003;77(12):6995-7006.

Pandya et al., Rationally designed capsid and transgene cassette of AAV6 vectors for dendritic cell-based cancer immunotherapy. Immunol Cell Biol. Feb. 2014;92(2):116-23. doi: 10.1038/icb.2013.74. Epub Nov. 12, 2013.

Pang et al., Long-Term Retinal Function and Structure Rescue Using Capsid Mutant AAV8 Vector in the rd10 Mouse, a Model or Recessive Retinitis Pigmentosa. Copyrgt. The American Society of Gene & Cell Therapy, Molecular Therapy, pp. 1-9,2010.

Petrs-Silva et al., High-Efficiency Transduction of the Mouse Retina by Tyrosine-Mutant AAV Serotype Vectors. Copyrgt. The American Society of Gene & Cell Therapy, www.moleculartherapy.org, Molecular Therapy, vol. 17, No. 3, pp. 463-471, Mar. 2009.

Petrs-Silva et al., Novel Properties of Tyrosine-Mutant AAV2 Vectors in the Mouse Retina. Copyrgt. The American Society of Gene & Cell Therapy, www.moleculartherapy.org, Molecular Therapy, vol. 19, No. 2, pp. 293-301, Feb. 2011.

Qi et al., Comparison of Transduction Efficiency of Tyrosine-Mutant AAV Serotype Vectors in Kidney. Copyrgt. 2012 The Authors Clinical and Experimental Pharmacology and Physiology, .Copyrgt. 2012 Wiley Publishing Asia Pty Ltd., doi:10.1111/1440-1681.12037, 8 pages.

Qiao et al., 451. Comparison of Transduction Efficiency of Tyrosine-Mutant AAV Vectors in Muscle. Mol Ther. 2009;17(Supp. 1):S175-6.

Qiao et al., Adeno-Associated Virus Serotype 6 Capsid Tyrosine-to-Phenylalanine Mutations Improve Gene Transfer to Skeletal Muscle. Human Gene Therapy 21:1343-1348 (Oct. 2010),.Copyrgt. Mary Ann Liebert, Inc., doi: 10.1089/hum.2010.003, pp. 1343-1348.

Qiao et al., Single Tyrosine Mutation in AAV8 and AAV9 Capsids Is Insufficient to Enhance Gene Delivery to Skeletal Muscle and Heart. Human Gene Therapy Methods: Part B 23:29-37 (Feb. 2012), .COPYRGT. Mary Ann Liebert, Inc., doi: 10.1089/hgtb.2011.229, pp. 29-37.

Qing et al., Development of Capsid-Modified Next Generation AAVrh74 Vectors with Increased Transduction Efficiency in Primary Human Skeletal Muscle Cells: Implications in Gene Therapy of Muscular Dystrophies. Molecular Therapy. Apr. 27, 2021; 29(4 Supp 1):159-160.

Qing et al., Role of tyrosine phosphorylation of a cellular protein in adeno-associated virus 2-mediated transgene expression. Proc Natl Acad Sci U S A. Sep. 30, 1997;94(20):10879-84. doi: 10.1073/pnas.94.20.10879.

Radivojac et al., Identification, analysis, and prediction of protein ubiquitination sites. Proteins. Feb. 1, 2010;78(2):365-80. Author manuscript, 30 pages.

Rakoczy et al., Development of Gene Therapy-Based Strategies for the Treatment of Eye Diseases. Drug Development Research. 1999;46:277-285.

(56) References Cited

OTHER PUBLICATIONS

Rosario et al., Microglia-specific targeting by novel capsid-modified AAV6 vectors. Mol Ther Methods Clin Dev. Apr. 13, 2016;3:16026. doi: 10.1038/mtm.2016.26.
Ruan et al., Development of an Anti-Angiogenic Therapeutic Model Combining scAAV2-delivered siRNAs and Noninvasive Photoacoustic Imaging of Tumor Vasculature Development. Cancer Lett. (2012), http://dx.doi.org/10.1016/j.canlet.2012.11.016,Dec. 4, 2012, 10 pages.
Rutledge et al., Infectious clones and vectors derived from adeno-associated virus (AAV) serotypes other than AAV type 2. J Virol. Jan. 1998;72(1):309-19.
Ryals et al., Quantifying Transduction Efficiencies of Unmodified and Tyrosine Capsid Mutant AAV Vectors in Vitro Using Two Ocular Cell Lines. Molecular Vision 2011; 17:1090-1102 (http://www.molvis.org/molvis/v17/a124), Apr. 29, 2011,pp. 1090-1102.
Schaffer et al., GenBank Submission: ADW24578. Apr. 7, 2005. 2 pages.
Sen et al., Improved adeno-associated virus (AAV) serotype 1 and 5 vectors for gene therapy. Sci Rep. 2013;3:1832. doi: 10.1038/srep01832.
Sen et al., Targeted modifications in adeno-associated virus serotype 8 capsid improves its hepatic gene transfer efficiency in vivo. Hum Gene Ther Methods. Apr. 2013;24(2):104-16. doi: 10.1089/hgtb.2012.195.
Shieh et al., Re: "Moving Forward After Two Deaths in a Gene Therapy Trial of Myotubular Myopathy" by Wilson and Flotte. Hum Gene Ther. Aug. 2020;31(15-16):787. doi: 10.1089/hum.2020.217.
Shin et al., A Simplified Immune Suppression Scheme Leads to Persistent Micro-Dystrophin Expression in Duchenne Muscular Dystrophy Dogs. Human Gene Therapy 23:202-209 (Feb. 2012), .Copyrgt. Mary Ann Libert, Inc., doi: 10.1089/hum.2011,147, pp. 202-209.
Shoti et al., Development of Genome-Modified Generation X Single-Stranded AAVrh74 Vectors with Improved Transgene Expression in Primary Human Skeletal Muscle Cells. Molecular Therapy. Apr. 27, 2021;29(4 Supp 1):184-185.
Song et al., High-efficiency transduction of primary human hematopoietic stem cells and erythroid lineage-restricted expression by optimized AAV6 serotype vectors in vitro and in a murine xenograft model in vivo. PLoS One. 2013;8(3):e58757. doi: 10.1371/journal.pone.0058757. Epub Mar. 14, 2013.
Song et al., Optimizing the transduction efficiency of capsid-modified AAV6 serotype vectors in primary human hematopoietic stem cells in vitro and in a xenograft mouse model in vivo. Cytotherapy. 2013;15:986-98. Author Manuscript, 22 pages.
Ussher et al., Optimized Transduction of Human Monocyte-Derived Dendritic Cells by Recombinant Adeno-Associated Virus Serotype 6. Human Gene Therapy 21:1675-1686 (Dec. 2010), .Copyrgt. Mary Ann Liebert, Inc., doi: 10.1089/hum.2010.078,pp. 1675-1686.
Vandenberghe et al., [Naturally occurring singleton residues in AAV capsid impact performance and illustrate structural constraints in 70012] B4Y882_9VIRU sequence alignment, Submitted Sep. 23, 2008. 2 Pages. [Also cited as Vandenberghe et al., Naturally occurring singleton residues in AAV capsid impact performance and illustrate structural constraints. Submitted 2007. EMBL/GenBank/DDBJ databases. Accession No. B4Y882_9VIRU.
Wang et al., Limitations of encapsidation of recombinant self-complementary adeno-associated viral genomes in different serotype capsids and their quantitation. Hum Gene Ther Methods. Aug. 2012;23(4):225-33. doi: 10.1089/hgtb.2012.090.
Yan et al. Ubiquitination of both Adeno-Associated Virus Type 2 and 5 Capsid Proteins Affects the Transduction Efficiency of Recombinant Vectors, Journal of Virology 76(5):2043-2053 (Mar. 2002), 11 pages.
Zhang et al., 453. Novel Tyrosine Mutant Vectors Expand the Utilities of AAV-Mediated Muscle Gene Therapy. Mol Ther. 2009;17(Supp. 1):S176-7.
Zhong et al., 371. High-Efficiency Transduction of Human Cells In Vitro and Murine Hepatocytes In Vivo at Further Reduced Doses of AAV2 Vectors Containing Multiple-Mutations in Surface-Exposed Tyrosine Residues in the Viral Capsid. Mol Ther. 2009;17(Supp. 1):S145.
Zhong et al., 90. Critical Requirement of a Cellular Chaperone Protein, FKBP52, for Intracellular Trafficking and Nuclear Transport of Tyrosine-Mutant AAV2 Vectors for High-Efficiency Transduction of Murine Embryo Fibroblasts. Mol Ther. 2009;17(Supp. 1):S36-7.
Zhong et al., A Dual Role of EGFR Protein Tyrosine Kinase Signaling in Ubiquitination of AAV2 Capsids and Viral Second-strand DNA Synthesis. The American Society of Gene Therapy, Molecular Therapy 15(7):1323-1330 (Jul. 2007), 8 pages.
Zhong et al., Evaluation of Primitive Murine Hematopoietic Stem and Progenitor Cell Transduction In Vitro and In Vivo by Recombinant Adeno-Associated Virus Vector Serotypes 1 Through 5. Human Gene Therapy 17(3):321-333 (Mar. 2006), 13 pages.
Zhong et al., Next generation of adeno-associated virus 2 vectors: Point mutations in tyrosines lead to high-efficiency transduction at lower doses. Proc Natl Acad Sci U S A. Jun. 3, 2008;105(22):7827-32. doi: 10.1073/pnas.0802866105. Epub May 29, 2008. Erratum in Proc Natl Acad Sci U S A. Aug. 5, 2008;105(31):11032.
Zolotukhin et al., Production and purification of serotype 1, 2, and 5 recombinant adeno-associated viral vectors. Methods. Oct. 2002;28(2):158-67. doi: 10.1016/s1046-2023(02)00220-7.
International Search Report and Written Opinion for Application No. PCT/US2022/025916 mailed Feb. 1, 2023.
Yazicioglu et al., AAV-Rh74 capsid protein VP1 variant Y253F/Y275F/Y447F/Y703F/Y707F/Y733F, GSP Database Accession No. BX21206, Dec. 19, 2013. 1 page.
International Preliminary Report on Patentability for Application No. PCT/US2022/025916 mailed Nov. 2, 2023.
Li et al., Engineering adeno-associated virus vectors for gene therapy. Nat Rev Genet. Apr. 2020;21(4):255-272. doi: 10.1038/s41576-019-0205-4. Epub Feb. 10, 2020.
Wu et al., Adeno-associated virus serotypes: vector toolkit for human gene therapy. Mol Ther. Sep. 2006;14(3):316-27. doi: 10.1016/j.ymthe.2006.05.009. Epub Jul. 7, 2006.
U.S. Appl. No. 18/287,711, filed Oct. 20, 2023, Srivastava et al.
PCT/US2022/025916, Nov. 2, 2023, International Preliminary Report on Patentability.

\* cited by examiner

| CAPSID | SEQUENCE |
|---|---|
| | 1                                                                                                    100 |
| AAV1 (1) | MAADGYLPDWLEDNLSEGIREWWDLKPGAPKPPKANQQKQDDGRGLVLPGYKYLGPFNGLDKGEPVNAADAAALEHDKAYDQQLKAGDNPYLRYNHADAEF |
| AAV2 (1) | MAADGYLPDWLEDTLSEGIRQWWKLKPGPPPPKPAERHKDDSRGLVLPGYKYLGPFNGLDKGEPVNEADAAALEHDKAYDRQLDSGDNPYLKYNHADAEF |
| AAV3 (1) | MAADGYLPDWLEDNLSEGIREWWALKPGVPQPKANQQHQDNARGLVLPGYKYLGPGNGLDKGEPVNEADAAALEHDKAYDQQLKAGDNPYLKYNHADAEF |
| AAV4 (1) | -MTDGYLPDWLEDNLSEGVREWWALQPGAPKPKANQQHQNAHQDQAKGLVLPGYNYLGPGNGLDRGEPVNRADEVAREHDISYNEQLEAGDNPYLKYNHADAEF |
| AAV5 (1) | MSFVDHPPDWLEEVG--EGLREFLGLEAGPPKPKPNQQHQDQARGLVLPGYNYLGPGNGLDRGEPVNRADEVAREHDISYNEQLEAGDNPYLRYNHADAEF |
| AAV6 (1) | MAADGYLPDWLEDNLSEGIREWWDLKPGAPKPPKANQQKQDDGRGLVLPGYKYLGPFNGLDKGEPVNAADAAALEHDKAYDQQLKAGDNPYLRYNHADAEF |
| AAV7 (1) | MAADGYLPDWLEDNLSEGIREWWDLKPGAPKPKANQQKQDNGRGLVLPGYKYLGPFNGLDKGEPVNAADAAALEHDKAYDQQLQAGDNPYLRYNHADAEF |
| AAV8 (1) | MAADGYLPDWLEDNLSEGIREWWALKPGAPKPKANQQHQDDGRGLVLPGYKYLGPFNGLDKGEPVNAADAAALEHDKAYDQQLKAGDNPYLKYNHADAEF |
| AAV9 (1) | MAADGYLPDWLEDNLSEGIREWWALKPGAPQPKANQQKANQQHQDNARGLVLPGYKYLGPGNGLDKGEPVNAADAAALEHDKAYDQQLKAGDNPYLKYNHADAEF |
| AAV10 (1) | MAADGYLPDWLEDNLSEGIREWWDLKPGAPKPKANQQKQDDGRGLVLPGFNGLDKGEPVNAADAAALEHDKAYDQQLKAGDNPYLRYNHADAEF |
| | 101                                                                                                  200 |
| AAV1 (101) | QERLQEDTSFGGNLGRAVFQAKKRVLEPLGLVEEGAKTAPGKKRPVEQSPQE-PDSSSGIGKTGQQPAKKRLNFGQTGDSESVPDPQPLGEPPATPAAVG |
| AAV2 (101) | QERLKEDTSFGGNLGRAVFQAKKRVLEPLGLVEEPVKTAPGKKRPVEHSPVE-PDSSSGTGKAGQQPARKRLNFGQTGDADSVPDPQPLGQPPAAPSGLG |
| AAV3 (101) | QERLQEDTSFGGNLGRAVFQAKKRVLEPLGLVEEAAKTAPGKKGAVDQSPQE-PDSSSGVGKSGKQPARKRLNFGQTGDSESVPDPQPLGEPPAAPTSLG |
| AAV4 (100) | CQRLQEDTSFGGNLGRAVFQAKKRVLEPLGLVEQAGETAPGKKRPLIESPQQ-PDSSTGIGKKGKQPAKKKLVFEDETGAGDGP---PEGSTSGAMSDDS |
| AAV5 (100) | QEKLADDTSFGGNLGRAVFQAKKRVLEPFGLVEEGAKTAPTGKRIDDHFPKR------KKARTEEDSKPSTSSDAEAGPSGS-QQLQIPAQPASSLG |
| AAV6 (101) | QERLQEDTSFGGNLGRAVFQAKKRVLEPLGLVEEGAKTAPGKKRPVEQSPQE-PDSSSGIGKTGQQPAKKRLNFGQTGDSESVPDPQPLGEPPATPAAVG |
| AAV7 (101) | QERLQEDTSFGGNLGRAVFQAKKRVLEPLGLVEEGAKTAPAKKRPVEPSPQRSPDSSTGIGKKGQQPARKRLNFGQTGDSESVPDPQPLGEPPAAPSSVG |
| AAV8 (101) | QERLQEDTSFGGNLGRAVFQAKKRVLEEAAKTAPGKKRPVEPSPQRSPDSSTGIGKKGQQPARKRLNFGQTGDSESVPDPQPLGEPPAAPSGVG |
| AAV9 (101) | QERLKEDTSFGGNLGRAVFQAKKRILEPLGLVEEAAKTAPGKKRPVEQSPQE-PDSSAGIGKSGAQPAKKRLNFGQTGDTESVPDPQPIGEPPAAPSGVG |
| AAV10 (101) | QERLQEDTSFGGNLGRAVFQAKKRVLEPLGLVEEGAKTAPGKKRPVEPSPQRSPDSSTGIGKKGQQPAKKRLNFGQTGDSESVPDPQPIGEPPAGPSGLG |
| | 201                                                                                                  300 |
| AAV1 (200) | PTTMASGGGAPMADNNEGADGVGNASGNWHCDSTWLGDRVITTSTRTWALPTYNNHLYKQISSAST-GASNDNHYFGYSTPWGYFDFNRFHCHFSPRDWQ |
| AAV2 (200) | TNTMATGSGAPMADNNEGADGVGNSSGNWHCDSTWMGDRVITTSTRTWALPTYNNHLYKQISSQS--GASNDNHYFGYSTPWGYFDFNRFHCHFSPRDWQ |
| AAV3 (200) | SNTMASGGGAPMADNNEGADGVGNSSGNWHCDSQWLGDRVITTSTRTWALPTYNNHLYKQISSQS--GASNDNHYFGYSTPWGYFDFNRFHCHFSPRDWQ |
| AAV4 (196) | EMRAAAGGAAVEGG--QGADVGNASGDWHCDSTWSEGHVTTSTRTWVLPTYNNHLYKRLGESLQ-----SNTYNGFSTPWGYFDFNRFHCHFSPRDWQ |
| AAV5 (190) | ADTMSAGGGPLGDNNQGADGVGNASGDWHCDSTWMGDRVVTKSTRTWVLPSYNNHQYREIKSGS-VDGSNANAYFGYSTPWGYFDFNRFHSWSPRDWQ |
| AAV6 (200) | PTTMASGGGAPMADNNEGADGVGNASGNWHCDSTWLGDRVITTSTRTWALPTYNNHLYKQISSAST-GASNDNHYFGYSTPWGYFDFNRFHCHFSPRDWQ |
| AAV7 (201) | SGTVAAGGGAPMADNNEGADGVGSSSGNWHCDSTWLGDRVITTSTRTWALPTYNNHLYKQISSETAG-STNDNTYFGYSTPWGYFDFNRFHCHFSPRDWQ |
| AAV8 (201) | PNTMAAGGGAPMADNNEGADGVGSSSGNWHCDSQWLGDRVITTSTRTWALPTYNNHLYKQISNGTSGGATNDNTYFGYSTPWGYFDFNRFHCHFSPRDWQ |
| AAV9 (200) | SLIMASGGGAPVADNNEGADGVGSSSGNWHCDSTWLGDRVITTSTRTWALPTYNNHLYKQISNSTSGGSSNDNAYFGYSTPWGYFDFNRFHCHFSPRDWQ |
| AAV10 (201) | SGTMAAGGGAPMADNNEGADGVGSSSGNWHCDSTWLGDRVITTSTRTWALPTYNNHLYKQISNGTSGGSTNDNTYFGYSTPWGYFDFNRFHCHFSPRDWQ |

*FIG. 2A-1*

```
              301                                                                                       400
AAV1  (299)   RLINNNWGFRPKRLNFKLFNIQVKEVTTNDGVTTIANNLTSTVQVFSDSEYQLPYVLGSAHQGCLPPFPADVFMIPQYGYLTLNNGSQA---VGRSSFYC
AAV2  (298)   RLINNNWGFRPKRLNFKLFNIQVKEVTQNDGTTTIANNLTSTVQVFTDSEYQLPYVLGSAHQGCLPPFPADVFMVPQYGYLTLNNGSQA---VGRSSFYC
AAV3  (298)   RLINNNWGFRPKKLSFKLFNIQVRGVTQNDGTTTIANNLTSTVQVFTDSEYQLPYVLGSAHQGCLPPFPADVFMVPQYGYLTLNNGSQA---VGRSSFYC
AAV4  (289)   RLINNNWGFRPKAMRVKIFNIQVKEVTTSNGETTVANNLTSTVQIFADSSYELPYVMDAGQEGSLPPFPNDVFMVPQYGYCGLVTGNTSQQQTDRNAFYC
AAV5  (289)   RLINNYWGFRPRSLRVKIFNIQVKEVTVQDSTTTIANNLTSTVQVFTDDYQLPYVVGNGTEGCLPAFPQVFTLPQYGYATLNRDNTEN-PTERSSFFC
AAV6  (299)   RLINNNWGFRPKRLNFKLFNIQVKEVTTNDGVTTIANNLTSTVQVFSDSEYQLPYVLGSAHQGCLPPFPADVFMIPQYGYLTLNNGSQA---VGRSSFYC
AAV7  (300)   RLINNNWGFRPKKLRFKLRFKLFNIQVKEVTQNEGTKTIANNLTSTIQVFTDSEYQLPYVLGSAHQGCLPPFPADVFMIPQYGYLTLNNGSQS---VGRSSFYC
AAV8  (301)   RLINNNWGFRPKRLSFKLFNIQVKEVTQNEGTKTIANNLTSTIQVFTDSEYQLPYVLGSAHQGCLPPFPADVFMIPQYGYLTLNNGSQA---VGRSSFYC
AAV9  (300)   RLINNNWGFRPKRLNFKLFNIQVKEVTDNNGVKTIANNLTSTVQVFTDSDYQLPYVLGSAHEGCLPPFPADVFMIPQYGYLTLNDGSQA---VGRSSFYC
AAV10 (301)   RLINNNWGFRPKRLNFKLFNIQVKEVTQNEGTKTIANNLTSTIQVFTDSEYQLPYVLGSAHQGCLPPFPADVFMIPQYGYLTLNNGSQA---VGRSSFYC
              401                                                                                       500
AAV1  (396)   LEYFPSQMLRTGNNFTFSYTFEEVPFHSSYAHSQSLDRLMNPLIDQYLYYLNRTQ-NQSGSAQNKDLLFSRGSPAGMSVQPKNWLPGPCYRQQRVSKTKT
AAV2  (395)   LEYFPSQMLRTGNNFTFSYTFEDVPFHSSYAHSQSLDRLMNPLIDQYLYYLSRIN-TPSGTTTQSRLQFSQAGASDIRDQSRNWLPGPCYRQQRVSKTSA
AAV3  (395)   LEYFPSQMLRTGNNFQFSYTFEDVPFHSSYAHSQSLDRLMNPLIDQYLYYLNRTQGTTSGTTNQSRLLFSQAGPQSMSLQARNWLPGPCYRQQRLSKTAN
AAV4  (389)   LEYFPSQMLRTGNNFEITYSFEKVPFHSMYAHSQSLDRLMNPLIDQYLWGLQSTTGTTLNAGTATTNFKLRPTNFSNFKKNWLPGPSIKQQGFSKTAN
AAV5  (388)   LEYFPSKMLRTGNNFEFTYNFEEVPFHSSFAPSQNLFKLANPLVDQYLYRFVSTN------NTGGVQFNKNLAGRYANTYKNWFPGPMGRTQWNLGSG
AAV6  (396)   LEYFPSQMLRTGNNFTFSYTFEDVPFHSSYAHSQSLDRLMNPLIDQYLYYLNRTQ-NQSGSAQNKDLLFSRGSPAGMSVQPKNWLPGPCYRQQRVSKTKT
AAV7  (397)   LEYFPSQMLRTGNNFEFSYSFEDVPFHSSYAHSQSLDRLMNPLIDQYLYYLARTQSNPGGTAGNRELQFYQGGPSTMAEQAKNWLPGPCFRQQRVSKTLD
AAV8  (398)   LEYFPSQMLRTGNNFQFTYTFEDVPFHSSYAHSQSLDRLMNPLIDQYLYYLSRTQTT-GGTANTQTLGFSQGGPNTMANQAKNWLPGPCYRQQRVSTTTG
AAV9  (397)   LEYFPSQMLRTGNNFQFSYEFENVPFHSSYAHSQSLDRLMNPLIDQYLYYLYLSKTING--SGONQQTLKFSVAGPSNMAVQGRNYIPGPSYRQQRVSTVT
AAV10 (398)   LEYFPSQMLRTGNNFEFSYQFEDVPFHSSYAHSQSLDRLMNPLIDQYLYYLSRTQST-GGTAGTQLLFSQAGPNNMSAQAKNWLPGPCYRQQRVSTTLS
              501                                                                                       600
AAV1  (495)   DN------NNSNFTWTGASKYNLNGRESIINPGTAMASHKDDEDKFFPMSGVMIFGKE---SAGASNTALDNVMITDEEEIKATNPVATERFGTVAVNFQS
AAV2  (494)   DN------NNSEYSWTGATKYHLNGRDSLVNPGPAMASHKDDEEKFFPQSGVLIFGKQ---GSEKTNVDIEKVMITDEEEIRTTNPVATEQYGSVSTNLQR
AAV3  (495)   DN------NNSNFPWTAASKYHLNGRDSLVNPGPAMASHKDDEEKFFPMHGNLIFGKE---GTTASNAELDNVMITDEEEIRTTNPVATEQYGTVANNLQS
AAV4  (489)   QNYKIPATGSDSLIKYETHSTLDGRWSALTPGPPMATAGPADSKFS-NSQLIFAGPK---QNGNTATVPGTLIFTSEEELAATNATDTDMWGNLPGGDQS
AAV5  (481)   VN------RASVSAFATTNRMELEGASYQVPPQPNGMTNNLQGSNTYALENTMIFNSQPANPGTTATYLEGNMLITSESETQPVNRVAYNVGGQMATNNQS
AAV6  (495)   DN------NNSNFTWTGASKYNLNGRESIINPGTAMASHKDDEDKFFPMSGVMIFGKE---SAGASNTALDNVMITDEEEIKATNPVATERFGTVAVNLQS
AAV7  (497)   QN------NNSNFAWTGATKYHLNGRNSLANPGIAMATHKDDEDRFFPSSGVLIFGKT---GATNKTTLENVLMTNEEEIRPTNPVATEEYGIVSSNLQA
AAV8  (497)   QN------NNSNFAWTAGTKYHLNGRNSLANPGVAMATHKDDEDRFFPSNGILIFGKQ---NAARDNADYSDVMLTSEEEIKTTNPVATEEYGIVADNLQQ
AAV9  (495)   QN------NNSEFAWPGASSWALNGRNSLMNPGPAMASHKEGEDRFFPLSGSLIFGKQ---GTGRDNVDADKVMITNEEEIKTTNPVATESYGQVATNHQS
AAV10 (497)   QN------NNSNFAWTGATKYHLNGRDSLVNPGVAMATHKDDEERFFPSSGVLMFGKQ---GAGKDNVDYSSVMLTSEEEIKTTNPVATEQYGVVADNLQQ
```

FIG. 2A-2

```
                601                                                                                    700
AAV1  (587) SSTDPATGDVHAMGALPGMVWQDRDVYLQGPIWAKIPHTDGHFHPSPLMGGFGLKNPPPQILIKNTPVPANPPAEFSATKFASFITQYSTGQVSVEIEWE
AAV2  (586) GNRQAATADVNTQGVLPGMVWQDRDVYLQGPIWAKIPHTDGHFHPSPLMGGFGLKHPPPQILIKNTPVPANPSTTFSAAKFASFITQYSTGQVSVEIEWE
AAV3  (587) SNTAPTTGTVNHQGALPGMVWQDRDVYLQGPIWAKIPHTDGHFHPSPLMGGFGLKHPPPQIMIKNTPVPANPPTTFSPAKFASFITQYSTGQVSVEIEWE
AAV4  (585) NSNLPTVDRLTALGAVPGMVWQNRDIYYQGPIWAKIPHTDGHFHPSPLIGGFGLKHPPPQIFIKNTPVPANPATTESSTPVNSFITQYSTGQVSVQIDWE
AAV5  (576) STTAPATGTYNLQEIVPGSVWMERDVYLQGPIWAKIPETGAHFHPSPAMGGFGLKHPPPMLIKNTPVPGN-ITSFSDVPVSSFITQYSTGQVTVEMEWE
AAV6  (587) SSTDPATGDVHVMGALPGMVWQDRDVYLQGPIWAKIPHTDGHFHPSPLMGGFGLKHPPPQILIKNTPVPANPPAEFSATKFASFITQYSTGQVSVEIEWE
AAV7  (588) ANTAAQTQVVNNQGALPGMVWQNRDVYLQGPIWAKIPHTDGNFHPSPLMGGFGLKHPPPQILIKNTPVPANPPEVFTPAKFASFITQYSTGQVSVEIEWE
AAV8  (589) QNTAPQIGTVNSQGALPGMVWQNRDVYLQGPIWAKIPHTDGNFHPSPLMGGFGLKHPPPQILIKNTPVPADPPTTFNQSKLNSFITQYSTGQVSVEIEWE
AAV9  (587) AQAQAQTGWVQNQGILPGMVWQDRDVYLQGPIWAKIPHTDGNFHPSPLMGGFGMKHPPPQILIKNTPVPADPPTTAFNKDKLNSFITQYSTGQVSVEIEWE
AAV10 (589) QNAAPIVGAVNSQGALPGMVWQNRDVYLQGPIWAKIPHTDGNFHPSPLMGGFGLKHPPPQILIKNTPVPADPPTTFSQAKLASFITQYSTGQVSVEIEWE
                701                                        751
AAV1  (687) LQKENSKRWNPEVQYTSNYAKSANVDFTVDNNGLYTEPRPIGTRYLTRPL- SEQ ID NO:1
AAV2  (686) LQKENSKRWNPEIQYTSNYNKSVNVDFTVDTNGVYSEPRPIGTRYLTRNL- SEQ ID NO:2
AAV3  (687) LQKENSKRWNPEIQYTSNYNKSVNVDFTVDTNGVYSEPRPIGTRYLTRNL- SEQ ID NO:3
AAV4  (685) IQKERSKRWNPEVQFTSNYGQQNSLLWAPDAAGKYTEPRAIGTRYLTHHL- SEQ ID NO:4
AAV5  (675) LKKENSKRWNPEIQYTNNYNDPQFVDFAPDSTGEYRTTRPIGTRYLTRPL- SEQ ID NO:5
AAV6  (687) LQKENSKRWNPEVQYTSNYAKSANVDFTVDNNGLYTEPRPIGTRYLTRPL- SEQ ID NO:6
AAV7  (688) LQKENSKRWNPEIQYTSNFEKQTGVDFAVDSQGVYSEPRPIGTRYLTRNL- SEQ ID NO:7
AAV8  (689) LQKENSKRWNPEIQYTSNYYKSTSVDFAVNTEGVYSEPRPIGTRYLTRNL- SEQ ID NO:8
AAV9  (687) LQKENSKRWNPEIQYTSNYYKSNNVEFAVNTEGVYSEPRPIGTRYLTRNL- SEQ ID NO:9
AAV10 (689) LQKENSKRWNPEIQYTSNYYKSTNVDFAVNTDGTYSEPRPIGTRYLTRNL- SEQ ID NO:10
```

FIG. 2A-3

| AAV1 | AAV2 | AAV3 | AAV4 | AAV5 | AAV6 | AAV7 | AAV8 | AAV9 | AAV10 | AAV11 | AAV12 |
|---|---|---|---|---|---|---|---|---|---|---|---|
| NA | K24 | NA | NA | NA | NA | NA | NA | NA | NA | NA | NA |
| K26 | K26 | K26 | NA | NA | K26 | K26 | K26 | K26 | K26 | K26 | K26 |
| K31 | NA | NA | K30 | K30 | K31 | K31 | K31 | NA | K31 | K31 | NA |
| K33 | K33 | K33 | K32 | K32 | K33 | K33 | K33 | K33 | K33 | K33 | K33 |
| K38 | NA | NA | NA | NA | K38 | K38 | K38 | NA | K38 | K38 | NA |
| NA | K39 | NA | K50 | NA | NA | NA | NA | NA | NA | NA | NA |
| K51 | K51 | K51 | K60 | NA | K51 | K51 | K51 | K51 | K51 | K51 | K51 |
| K61 | K61 | K61 | K76 | NA | K61 | K61 | K61 | K61 | K61 | K61 | K61 |
| K77 | K77 | K77 | NA | NA | K77 | K77 | K77 | K77 | K77 | K77 | K77 |
| NA | NA | NA | K83 | NA | NA | NA | NA | NA | NA | NA | K81 |
| K84 | NA | K84 | K91 | NA | K84 | K84 | NA | K84 | K84 | K84 | NA |
| NA | K92 | K92 | NA | NA | NA | NA | NA | K92 | NA | NA | K92 |
| NA | NA | NA | NA | K102 | NA | NA | NA | NA | NA | NA | NA |
| NA | K105 | NA | NA | NA | NA | NA | NA | K105 | NA | NA | NA |
| NA | NA | NA | NA | K115 | NA | NA | NA | NA | NA | NA | NA |
| K122 | K122 | K122 | K121 | K121 | K122 | K122 | K122 | K122 | K122 | K122 | K122 |
| K123 | K123 | K123 | K122 | K122 | K123 | K123 | K123 | K123 | K123 | K123 | K123 |
| K137 | K137 | K137 | NA | K136 | K137 | K137 | K137 | K137 | K137 | K137 | K137 |
| K142 | K142 | K142 | K141 | NA | K142 | K142 | K142 | K142 | K142 | K142 | K142 |
| K143 | K143 | K143 | K142 | K142 | K143 | K143 | K143 | K143 | K143 | K143 | K142 |
| NA | NA | NA | NA | NA | NA | NA | NA | NA | NA | NA | K148 |
| NA | NA | NA | NA | K150 | NA | NA | NA | NA | NA | NA | NA |
| NA | NA | NA | NA | K152 | NA | NA | NA | NA | NA | NA | NA |
| NA | NA | NA | NA | K153 | NA | NA | NA | NA | NA | NA | NA |
| K161 | K161 | K161 | K160 | NA | K161 | K162 | K162 | K161 | K162 | K160 | K160 |
| NA | NA | NA | K161 | NA | NA | K163 | K163 | NA | K163 | K161 | K164 |
| NA | NA | NA | NA | NA | NA | NA | NA | NA | NA | NA | K165 |
| NA | NA | NA | NA | NA | NA | NA | NA | NA | NA | NA | K166 |

*FIG. 2B-1*

| | | | | | | | | | | | |
|---|---|---|---|---|---|---|---|---|---|---|---|
| NA | NA | K164 | K163 | NA | NA | NA | NA | NA | NA | NA | NA |
| NA | NA | NA | NA | K161 | NA | NA | NA | NA | NA | NA | K168 |
| K168 | NA | NA | K167 | NA | K168 | K168 | NA | K168 | K169 | K163 | NA |
| K169 | K169 | K169 | K168 | NA | K169 | K169 | K170 | K169 | K170 | NA | NA |
| NA | NA | NA | K169 | K232-I | NA | NA | NA | NA | NA | NA | NA |
| K258-S | K258-S | K258-S | K525-S | K251-S | K258-S | K259-S | K259-S | K258-S | K259-S | NA | NA |
| NA | NA | NA | NA | NA | NA | NA | NA | NA | NA | NA | NA |
| K310-I | K309-I | K309-I | K300-I | NA | K310-I | K311-I | K311-I | K311-I | K300-I | K309-I |
| NA | NA | K310-I | NA | NA | NA | K312-I | NA | NA | NA | NA | NA |
| K315-I | K314-I | K314-I | K305-I | K305-I | K315-I | K316-I | K317-I | K316-I | K305-I | K314-I |
| K322-I | K321-I | K321-I | K312-I | K312-I | K322-I | K323-I | K324-I | K323-I | K312-I | K321-I |
| NA | NA | NA | NA | NA | NA | NA | K333-S | K332-S | K333-S | NA | NA |
| NA | NA | NA | NA | K394-I | NA | NA | NA | NA | NA | NA | K384-I |
| NA | NA | NA | K411-I | NA | NA | NA | NA | NA | NA | NA | NA |
| NA | NA | NA | NA | K425-I | NA | NA | NA | K449-S | NA | K410-I | K419-I |
| NA | NA | NA | NA | NA | NA | NA | NA | K462-S | NA | NA | NA |
| K459-I | NA | NA | K459-I | K451-I | K459-I | NA | NA | NA | NA | NA | NA |
| NA | NA | NA | K469-I | NA | NA | NA | NA | NA | NA | NA | NA |
| NA | NA | NA | K470-I | K462-I | K476-I | K478-I | K478-I | NA | K458-I | K467-I |
| K476-I | NA | NA | K479-S | NA | NA | NA | NA | NA | K469-I | NA |
| NA | NA | NA | NA | NA | NA | NA | NA | NA | K478-I | K487-I |

FIG. 2B-2

| | | | | | | | | | | | |
|---|---|---|---|---|---|---|---|---|---|---|---|
| NA | NA | NA | NA | NA | NA | NA | NA | NA | NA | NA | K490-I |
| K491-S | K490-S | K491-S | K485-S | NA | K491-S | NA | NA | NA | NA | K484-S | K490-S |
| K493-S | NA | NA | NA | NA | K493-S | K493-S | NA | NA | NA | NA | NA |
| NA | NA | NA | K492-S | NA | NA | NA | NA | NA | NA | K491-S | K493-S |
| NA | NA | NA | K503-S | NA | NA | NA | NA | NA | NA | K502-S | K511-S |
| K508-S | K507-S | K508-S | NA | NA | K508-S | K510-S | K510-S | NA | K510-S | NA | NA |
| K528-S | K527-S | K528-S | NA | NA | K528-S | K530-S | K530-S | K528-S | K530-S | NA | NA |
| NA | NA | NA | NA | NA | K531-S | NA | NA | NA | NA | NA | NA |
| K533-S | K532-S | K533-S | K532-S | NA | K533-S | NA | NA | NA | NA | NA | NA |
| NA | NA | NA | NA | NA | NA | NA | NA | NA | NA | NA | NA |
| K545-S | K544-S | K545-S | K544-S | NA | K545-S | K547-S | K547-S | K545-S | K547-S | NA | NA |
| NA | NA | NA | NA | NA | NA | NA | NA | NA | NA | NA | NA |
| NA | K549-S | NA | NA | NA | NA | NA | NA | NA | NA | NA | NA |
| NA | NA | NA | NA | NA | NA | K553-S | NA | NA | NA | NA | NA |
| NA | K556-S | NA | NA | NA | NA | NA | NA | K557-S | NA | NA | NA |
| K567-S | NA | NA | NA | NA | K567-S | NA | K569-S | K567-S | K569-S | NA | NA |
| K621-I | K620-I | K621-I | K619-I | K610-I | K621-I | K622-I | K623-I | K621-I | K623-I | K618-I | K627-I |
| K641-I | K640-I | K641-I | K639-I | K630-I | K641-I | K642-I | K643-I | K641-I | K643-I | K638-I | K647-I |
| K650-I | K649-I | K650-I | K648-I | K639-I | K650-I | K651-I | K652-I | K650-I | K652-I | K647-I | K656-I |
| NA | NA | NA | NA | NA | NA | NA | NA | K664-I | NA | NA | NA |
| K666-S | K665-S | K666-S | NA | NA | K666-S | K667-S | K668-S | K666-S | K668-S | NA | NA |
| NA | NA | NA | NA | K676-I | NA | NA | NA | NA | NA | NA | NA |
| K689-I | K688-I | K689-I | K687-I | K677-I | K689-I | K690-I | K691-I | K689-I | K691-I | K686-I | K695-I |
| K693-I | K692-I | K693-I | K691-I | K681-I | K693-I | K694-I | K695-I | K693-I | K695-I | K690-I | K699-I |
| K707-S | K706-S | K707-S | NA | NA | K707-S | K708-S | K709-S | K707-S | K709-S | NA | NA |
| NA | NA | NA | K718-I | NA | NA | NA | NA | NA | NA | K717-I | NA |

*FIG. 2B-3*

| CAPSID | SEQUENCE | |
|---|---|---|
| | 1 | 100 |
| AAV1 (1) | MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF | |
| AAV2 (1) | MAADGYLPDWLEDTLSEGIRQWWKLKPGPPPKPAERHKDDSRGLVLPGYKYLGPFNGLDKGEPVNEADAAALEHDKAYDRQLDSGDNPYLKYNHADAEF | |
| AAV3 (1) | MAADGYLPDWLEDNLSEGIREWWALKPGVPQPKANQHQDNRRGLVLPGYKYLGPFNGLDKGEPVNEADAAALEHDKAYDQQLKAGDNPYLKYNHADAEF | |
| AAV4 (1) | -MTDGYLPDWLEDNLSEGVREWWALQPGAPKPKANQQHQDNARGLVLPGYKYLGPGNGLDKGEPVNAADAAALEHDKAYDQQLKAGDNPYLKYNHADAEF | |
| AAV5 (1) | MSFVDHPPDWLEEVG-EGLREFLGLEAGPPKPKPNQQHQDQARGLVLPGYNYLGPGNGLDRGEPVNRADEVAREHDISYNEQLEAGDNPYLKYNHADAEF | |
| AAV6 (1) | MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF | |
| AAV7 (1) | MAADGYLPDWLEDNLSEGIREWWALKPGAPKPKANQQKQDNGRGLVLPGYKYLGPFNGLDKGEPVNAADAAALEHDKAYDQQLKAGDNPYLRYNHADAEF | |
| AAV8 (1) | MAADGYLPDWLEDNLSEGIREWWALKPGAPKPKANQQKQDDGRGLVLPGYKYLGPFNGLDKGEPVNAADAAALEHDKAYDQQLQAGDNPYLRYNHADAEF | |
| AAV9 (1) | MAADGYLPDWLEDNLSEGIREWWALKPGAPQPKANQQHQDNARGLVLPGYKYLGPGNGLDKGEPVNAADAAALEHDKAYDQQLKAGDNPYLKYNHADAEF | |
| AAV10 (1) | MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF | |
| | 101 | 200 |
| AAV1 (101) | QERLQEDTSFGGNLGRAVFQAKKRVLEPLGLVEEGAKTAPGKKRPVEQSPQE-PDSSSGIGKTGQQPAKKRLNFGQTGDSESVPDPQPLGEPPATPAAVG | |
| AAV2 (101) | QERLKEDTSFGGNLGRAVFQAKKRVLEPLGLVEEPVKTAPGKKRPVEHSPVE-PDSSSGTGKAGQQPARKRLNFGQTGDADSVPDPQPLGQPPAAPSGLG | |
| AAV3 (101) | QERLQEDTSFGGNLGRAVFQAKKRILEPLGLVEEAAKTAPGKKRPVEHHSPVE-PDSSSGVGKSGKQPARKRLNFGQTGDSESVPDPQPLGEPPAAPTSLG | |
| AAV4 (100) | QQRLQEDTSFGGNLGRAVFQAKKRVLEPLGLVEQAGETAPGKKRPLIESPQQ-PDSSTGIGKKGKQPAKKKLVFEDETGAGDP---PEGSTSGAMSDDS | |
| AAV5 (100) | QEKLADDTSFGGNLGKAVFQAKKRVLEPFGLVEEGAKTAPTGKRIDDHFPKR------KKARTEEDSKPSTSSDAEAGPSGS-QQLQIPAQPASSLG | |
| AAV6 (101) | QERLQEDTSFGGNLGRAVFQAKKRVLEPLGLVEEGAKTAPGKKRPVEQSPQE-PDSSSGIGKTGQQPAKKRLNFGQTGDSESVPDPQPLGEPPATPAAVG | |
| AAV7 (101) | QERLQEDTSFGGNLGRAVFQAKKRVLEPLGLVEEGAKTAPAKKRPVEPSPQRSPDSSTGIGKKGQQPARKRLNFGQTGDSESVPDPQPLGEPPAAPSSVG | |
| AAV8 (101) | QERLQEDTSFGGNLGRAVFQAKKRVLEPLGLVEEAAKTAPGKKRPVEPSPQRSPDSSTGIGKSGAQPAKKRLNFGQTGDSESVPDPQPLGEPPAAPSGVG | |
| AAV9 (101) | QERLKEDTSFGGNLGRAVFQAKKRLLEPLGLVEEPLKTAPGKKRPVEQSPQE-PDSSAGIGKSGAQPAKKRLNFGQTGDTESVPDPQPLGEPPAAPSGVG | |
| AAV10 (101) | QERLQEDTSFGGNLGRAVFQAKKRVLEPLGLVEEGAKTAPGKKRPVEPSPQRSPDSSTGIGKKGQQPAKKRLNFGQTGDSESVPDPQPIGEPPAGPSGLG | |
| | 201 | 300 |
| AAV1 (200) | PTTMASGGGAPMADNNEGADGVGNASGNWHCDSTWLGDRVITTSTRTWALPTYNNHLYKQISSAST-GASNDNHYFGYSTPWGYFDFNRFHCHFSPRDWQ | |
| AAV2 (200) | TNTMATGSSGAPMADNNEGADGVGNSSGNWHCDSTWMGDRVITTSTRTWALPTYNNHLYKQISSQS--GASNDNHYFGYSTPWGYFDFNRFHCHFSPRDWQ | |
| AAV3 (201) | SNTMASGGGAPMADNNEGADGVGSSSGNWHCDSQWLGDRVITTSTRTWSEGHVTTSTRTWVLPTYNNHLYKQISSQS--GASNDNHYFGYSTPWGYFDFNRFHCHFSPRDWQ | |
| AAV4 (196) | EMRAAAGGAAVEGG--QGADGVGNASGDWHCDSTWMGDRVVTKSTRTWVLPSYNNHQYREIKSGS-VDGSNANAYFGYSTPWGYFDFNRFHSHWSPRDWQ | |
| AAV5 (190) | ADTMSAGGGPLGDNNQGADGVGNASGDWHCDSTWMGDRVITTSTRTWVLPSYNNHLYKRLGESLQ------SNTYNGFSTPWGYFDFNRFHCHFSPRDWQ | |
| AAV6 (200) | PTTMASGGGAPMADNNEGADGVGNASGNWHCDSTWLGDRVITTSTRTWALPTYNNHLYKQISSAST-GASNDNHYFGYSTPWGYFDFNRFHSHWSPRDWQ | |
| AAV7 (201) | SGTVAAGGGAPMADNNEGADGVGSSSGNWHCDSTWLGDRVITTSTRTWALPTYNNHLYKQISSETAG-STNDNTYFGYSTPWGYFDFNRFHCHFSPRDWQ | |
| AAV8 (201) | PNTMAAGGGAPMADNNEGADGVGSSSGNWHCDSTWLGDRVITTSTRTWALPTYNNHLYKQISNGTSGGATNDNTYFGYSTPWGYFDFNRFHCHFSPRDWQ | |
| AAV9 (201) | SLTMASGGAPVADNNEGADGVGSSSGNWHCDSQWLGDRVITTSTRTWALPTYNNHLYKQISNSTSGGSSNDNAYFGYSTPWGYFDFNRFHCHFSPRDWQ | |
| AAV10 (201) | SGTMAAGGGAPMADNNEGADGVGSSSGNWHCDSTWLGDRVITTSTRTWALPTYNNHLYKQISNGTSGGSTNDNTYFGYSTPWGYFDFNRFHCHFSPRDWQ | |

FIG. 2C-1

```
                                                                                                                                            400
         301
AAV1 (299)   RLINNNWGFRPKRLNFKLFNIQVKEVTTNDGVTTIANNLTSTVQVFSDSEYQLPYVLGSAHQGCLPFPADVFMIPQYGYLTLNNGSQA----VGRSSFYC
AAV2 (298)   RLINNNWGFRPKRLNFKLFNIQVKEVTQNDGTTTIANNLTSTVQVFTDSEYQLPYVLGSAHQGCLPPFPADVFMVPQYGYLTLNNGSQA----VGRSSFYC
AAV3 (298)   RLINNNWGFRPKKLSFKLFNIQVRGVTQNDGTTTIANNLTSTVQVFTDSEYQLPYVLGSAHQGCLPPFPADVFMVPQYGYLTLNNGSQA----VGRSSFYC
AAV4 (289)   RLINNNWGMRPKAMRVKIFNIQVKEVTTSNGETTVANNLTSTVQIFADSSYELPYVMDAGQEGSLPPFPNDVFMVPQYGYCGLVTGNTSQQQTDRNAFYC
AAV5 (289)   RLINNYWGFRPRSLRVKIFNIQVKEVTVQDSTTTIANNLTSTVQVFTDDDYQLPYVVGNGTEGCLPAFPPQVETLPQYGYATLNRDNTEN-PTERSSFFC
AAV6 (299)   RLINNNWGFRPKRLNFKLFNIQVKEVTTNDGVTTIANNLTSTVQVFSDSEYQLPYVLGSAHQGCLPPFPADVFMIPQYGYLTLNNGSQA----VGRSSFYC
AAV7 (300)   RLINNNWGFRPKRLRFKLFNIQVKEVTQNDGTTTIANNLTSTIQVFSDSEYQLPYVLGSAHQGCLPPFPADVFMIPQYGYLTLNNGSQS----VGRSSFYC
AAV8 (301)   RLINNNWGFRPKRLSFKLFNIQVKEVTQNEGTKTIANNLTSTIQVFTDSEYQLPYVLGSAHQGCLPPFPADVFMIPQYGYLTLNNGSQA----VGRSSFYC
AAV9 (300)   RLINNNWGFRPKRLNFKLFNIQVKEVTDNNGVKTIANNLTSTVQVFTDSDYQLPYVLGSAHEGCLPPFPADVFMIPQYGYLTLNDGSQA----VGRSSFYC
AAV10 (301)  RLINNNWGFRPKRLNFKLFNIQVKEVTQNEGTKTIANNLTSTIQVFTDSEYQLPYVLGSAHQGCLPPFPADVFMIPQYGYLTLNNGSQA----VGRSSFYC
                                                                                                                                            500
         401
AAV1 (396)   LEYFPSQMLRTGNNFTFSYTFEEVPFHSSYAHSQSLDRLMNPLIDQYLYYLNRTQ-NQSGSAQNKDLLFSRGSPAGMSVQPKNWLPGPCYRQQRVSKTKT
AAV2 (395)   LEYFPSQMLRTGNNFTFSYTFEDVPFHSSYAHSQSLDRLMNPLIDQYLYYLSRTN-TPSGTTTQSRLQFSQAGASDIRDQSRNWLPGPCYRQQRVSKTSA
AAV3 (395)   LEYFPSQMLRTGNNFQFSYTFEDVPFHSSYAHSQSLDRLMNPLIDQYLYYLNRTQGTTSGTTNQSRLLFSQAGPQSMSLQARNWLPGPCYRQQRLSKTAN
AAV4 (389)   LEYFPSQMLRTGNNFEITYSFEKVPFHSMYAHSQSLDRLMNPLIDQYLWGLQSTTTGTTLNAGTATTNFTKLRPTNFSNFKKNWLPGPSIKQQGFSKTAN
AAV5 (388)   LEYFPSKMLRTGNNFEFTYNFEEVPFHSSFAPSQNLFKLANPLVDQYLYRFVSTN------NTGGVQFNKNLAGRYANTYKNWFPGPMGRTQGWNLGSG
AAV6 (396)   LEYFPSQMLRTGNNFTFSYTFEDVPFHSSYAHSQSLDRLMNPLIDQYLYYLNRTQ-NQSGSAQNKDLLFSRGSPAGMSVQPKNWLPGPCYRQQRVSKTKT
AAV7 (397)   LEYFPSQMLRTGNNFEFSYSFEDVPFHSSYAHSQSLDRLMNPLIDQYLYYLARTQSNPGGTAGNRELQFYQGGPSTMAEQAKNWLPGPCFRQQRVSKTLD
AAV8 (398)   LEYFPSQMLRTGNNFQFTYTFEDVPFHSSYAHSQSLDRLMNPLIDQYLYYLSRTQT-GGTANTQTLGFSQGGPNTMANQAKNWLPGPCYRQQRVSTTTG
AAV9 (397)   LEYFPSQMLRTGNNFQFSYEFENVPFHSSYAHSQSLDRLMNPLIDQYLYYLSKTING--SGQNQQTLKFSVAGPSNMAVQGRNYIPGPSYRQQRVSTTVT
AAV10 (398)  LEYFPSQMLRTGNNFEFSYQFEDVPFHSSYAHSQSLDRLMNPLIDQYLYYLSRTQST-GGTAGTQQLLFSQAGPNNMSAQAKNWLPGPCYRQQRVSTTLS
                                                                                                                                            600
         501
AAV1 (495)   DN-----NNSNFTWTGASKYNLNGRESIINPGTAMASHKDDEDKFFPMSGVMIFGKE---SAGASNTALDNVMITDEEEIKATNPVATERFGTVAVNFQS
AAV2 (494)   DN-----NNSEYSWTGATKYHLNGRDSLVNPGPAMASHKDDEEKFFPQSGVLIFGKQ---GSEKTNVDIEKVMITDEEEIRTTNPVATEQYGSVSTNLQR
AAV3 (495)   DN-----NNSNFPWTAASKYHLNGRDSLVNPGPAMASHKDDEEKFFPMHGNLIFGKE---GTTASNAELDNVMITDEEEIRTTNPVATEQYGTVANNLQS
AAV4 (489)   QNYKIPATGSDSLIKYETHSTLDGRWSALTPGPPMATAGPADSKFS-NSQLIFAGPK---QNGNTATVPGTLIFTSEEELAATNATDTDMWGNLPGGDQS
AAV5 (481)   VN-----RASVSAFATTNRMELEGASYQVPPQPNGMTNNLQGSNTYALENTMIFNSQPANPGTTATYLEGNMLITSESETQPVNRVAYNVGGQMATNNQS
AAV6 (495)   DN-----NNSNFTWTGASKYNLNGRESIINPGTAMASHKDDKDKFFPMSGVMIFGKE---SAGASNTALDNVMITDEEEIKATNPVATERFGTVAVNLQS
AAV7 (497)   QN-----NNSNFAWTGATKYHLNGRNSLVNPGVAMATHKDDEDRFFPSSGVLIFGKT---GATNKTTLENVLMTNEEEIRPTNPVATEEYGIVSSNLQA
AAV8 (497)   QN-----NNSNFAWTAGTKYHLNGRNSLANPGIAMATHKDDEERFFPSNGILIFGKQ---NAARDNADYSDVMLTSEEEIKTTNPVATEEYGIVADNLQQ
AAV9 (495)   QN-----NNSEFAWPGASSWALNGRNSLMNPGPAMASHKEGEDRFFPLSGSLIFGKQ---GTGRDNVDADKVMITNEEEIKTTNPVATESYGQVATNHQS
AAV10 (497)  QN-----NNSNFAWTGATKYHLNGRDSLVNPGVAMATHKDDEERFFPSSGVMLTSEEEIKTTNPVATEQYGVVADNLQQ---GAGKDNVDYSSVMLTSEEEIKTTNPVATEQYGVVADNLQQ
```

FIG. 2C-2

```
        601                                                                                         700
AAV1  (587) SSTDPATGDVHAMGALPGMVWQDRDVYLQGPIWAKIPHTDGHFHPSPLMGGFGLKNPPPQILIKNTPVPANPPAEFSATKFASFITQYSTGQVSVEIEWE
AAV2  (586) GNRQAATADVNTQGVLPGMVWQDRDVYLQGPIWAKIPHTDGHFHPSPLMGGFGLKHPPPQILIKNTPVPANPSTTFSAAKFASFITQYSTGQVSVEIEWE
AAV3  (587) SNTAPTTGTVNHQGALPGMVWQDRDVYLQGPIWAKIPHTDGHFHPSPLMGGFGLKHPPPQIMIKNTPVPANPPTTFSPAKFASFITQYSTGQVSVEIEWE
AAV4  (585) NSNLPTVDRLTALGAVPGMVWQNRDIYYQGPIWAKIPHTDGHFHPSPLIGGFGLKHPPPQIFIKNTPVPANPATTFSSTPVNSFITQYSTGQVSVQIDWE
AAV5  (576) STTAPATGTYNLQEIVPGSVWMERDVYLQGPIWAKIPETGAHFHPSPAMGGFGLKHPPPMLIKNTPVPGN-ITSFSDVPVSSFITQYSTGQVTVEMEWE
AAV6  (587) SSTDPATGDVHVMGALPGMVWQDRDVYLQGPIWAKIPHTDGHFHPSPLMGGFGLKHPPPQILIKNTPVPANPPAEFSATKFASFITQYSTGQVSVEIEWE
AAV7  (588) ANTAAQTQVVNNQGALPGMVWQNRDVYLQGPIWAKIPHTDGNFHPSPLMGGFGLKHPPPQILIKNTPVPANPPEVFTPAKFASFITQYSTGQVSVEIEWE
AAV8  (589) QNTAPQIGTVNSQGALPGMVWQNRDVYLQGPIWAKIPHTDGNFHPSPLMGGFGLKHPPPQILIKNTPVPADPPTTFNQSKLNSFITQYSTGQVSVEIEWE
AAV9  (587) AQAQTGWVQNQGILPGMVWQDRDVYLQGPIWAKIPHTDGNFHPSPLMGGFGMKHPPPQILIKNTPVPADPPTAFNKDKLNSFITQYSTGQVSVEIEWE
AAV10 (589) QNAAPIVGAVNSQGALPGMVWQNRDVYLQGPIWAKIPHTDGNFHPSPLMGGFGLKHPPPQILIKNTPVPADPPTTFSQAKLASFITQYSTGQVSVEIEWE
        701                                    751
AAV1  (687) LQKENSKRWNPEVQYTSNYAKSANVDFTVDNNGLYTEPRPIGTRYLTRPL- SEQ ID NO: 1
AAV2  (686) LQKENSKRWNPEIQYTSNYNKSVNVDFTVDTNGVYSEPRPIGTRYLTRNL- SEQ ID NO: 2
AAV3  (687) LQKENSKRWNPEIQYTSNYNKSVNVDFTVDTNGVYSEPRPIGTRYLTRNL- SEQ ID NO: 3
AAV4  (685) IQKERSKRWNPEVQFTSNYGQQNSLLWAPDAAGKYTEPRAIGTRYLTHHL- SEQ ID NO: 4
AAV5  (675) LKKENSKRWNPEIQYTNNYNDPQFVDFAPDSTGEYRTTRPIGTRYLTRPL- SEQ ID NO: 5
AAV6  (687) LQKENSKRWNPEVQYTSNYAKSANVDFTVDNNGLYTEPRPIGTRYLTRPL- SEQ ID NO: 6
AAV7  (688) LQKENSKRWNPEIQYTSNFEKQTGVDFAVDSQGVYSEPRPIGTRYLTRNL- SEQ ID NO: 7
AAV8  (689) LQKENSKRWNPEIQYTSNYYKSTSVDFAVNTEGVYSEPRPIGTRYLTRNL- SEQ ID NO: 8
AAV9  (687) LQKENSKRWNPEIQYTSNYYKSNNVEFAVNTEGVYSEPRPIGTRYLTRNL- SEQ ID NO: 9
AAV10 (689) LQKENSKRWNPEIQYTSNYYKSTNVDFAVNTDGTYSEPRPIGTRYLTRNL- SEQ ID NO: 10
```

FIG. 2C-3

| CAPSID | SEQUENCE |
|---|---|
| | 1                                                                                                  100 |
| AAV1 (1) | MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF |
| AAV2 (1) | MAADGYLPDWLEDTLSEGIRQWWKLKPGPPPPKPAERHKDDSRGLVLPGYKYLGPFNGLDKGEPVNEADAAALEHDKAYDRQLDSGDNPYLKYNHADAEF |
| AAV3 (1) | MAADGYLPDWLEDNLSEGIREWWALKPGVPQPKANQQHQDNRRGLVLPGYKYLGPGNGLDKGEPVNEADAAALEHDKAYDQQLKAGDNPYLKYNHADAEF |
| AAV4 (1) | -MTDGYLPDWLEDNLSEGVREWWALQPGAPKPKANQQHQDNARGLVLPGYNYLGPGNGLDRGEPVNRADEVAREHDISYNEQLEAGDNPYLKYNHADAEF |
| AAV5 (1) | MSFVDHPPDWLEEVG-EGLREFLGLEAGPPKPKPNQQHQDQARGLVLPGYKYLGPGNGLDKGEPVNAADAAALEHDKAYDQQLKAGDNPYLRYNHADAEF |
| AAV6 (1) | MAADGYLPDWLEDNLSEGIREWWDLKPGAPKPKANQQKQDDGRGLVLPGYKYLGPFNGLDKGEPVNRADEVAREHDISYNEQLEAGDNPYLKYNHADAEF |
| AAV7 (1) | MAADGYLPDWLEDNLSEGIREWWDLKPGAPKPKANQQKQDNGRGLVLPGYKYLGPFNGLDKGEPVNAADAAALEHDKAYDQQLKAGDNPYLRYNHADAEF |
| AAV8 (1) | MAADGYLPDWLEDNLSEGIREWWALKPGAPQPKANQQHQDNARGLVLPGYKYLGPGNGLDKGEPVNAADAAALEHDKAYDQQLQAGDNPYLRYNHADAEF |
| AAV9 (1) | MAADGYLPDWLEDNLSEGIREWWALKPGAPKPKANQQKQDDGRGLVLPGYKYLGPFNGLDKGEPVNAADAAALEHDKAYDQQLKAGDNPYLKYNHADAEF |
| AAV10 (1) | MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF |
| | 101                                                                                                200 |
| AAV1 (101) | QERLQEDTSFGGNLGRAVFQAKKRVLEPLGLVEEGAKTAPGKKRPVEQSPQE-PDSSSGIGKTGQQPAKKRLNFGQTGDSESVPDPQPLGEPPATPAAVG |
| AAV2 (101) | QERLKEDTSFGGNLGRAVFQAKKRVLEPLGLVEEPVKTAPGKKRPVEHSPVE-PDSSSGTGKAGQQPARKRLNFGQTGDADSVPDPQPLGQPPAAPSGLG |
| AAV3 (101) | QERLQEDTSFGGNLGRAVFQAKKRILEPLGLVEEAAKTAPGKKGAVDQSPQE-PDSSSGVGKSGKQPARKRLNFGQTGDSESVPDPQPLGEPPAAPTSLG |
| AAV4 (100) | QQRLQGDTSFGGNLGRAVFQAKKRVLEPLGLVEQAGETAPGKKRPLIESPQQ-PDSSTGIGKKGKQPAKKKLVFEDETGAGDGP---PEGSTSGAMSDDS |
| AAV5 (100) | QEKLADDTSFGGNLGKAVFQAKKRVLEPFGLVEEGAKTAPTGKRIDDHFPKR-------KKARTEEDSKPSTSSDAEAGPSGS-QQLQIPAQPASSLG |
| AAV6 (101) | QERLQEDTSFGGNLGRAVFQAKKRVLEPFGLVEEGAKTAPGKKRPVEQSPQE-PDSSSGIGKTGQQPAKKRLNFGQTGDSESVPDPQPLGEPPATPAAVG |
| AAV7 (101) | QERLQEDTSFGGNLGRAVFQAKKRVLEPLGLVEEGAKTAPAKKRPVEPSPQRSPDSSTGIGKKGQQPARKRLNFGQTGDSESVPDPQPLGEPPAAPSSVG |
| AAV8 (101) | QERLQEDTSFGGNLGRAVFQAKKRVLEPLGLVEEGAKTAPGKKRPVEPSPQRSPDSSTGIGKKGQQPARKRLNFGQTGDSESVPDPQPLGEPPAAPSGVG |
| AAV9 (101) | QERLKEDTSFGGNLGRAVFQAKKRLLEPLGLVEEAAKTAPGKKRPVEQSPQE-PDSSACIGKSGAQPAKKRLNFGQTGDTESVPDPQPIGEPPAAPSGVG |
| AAV10 (101) | QERLQEDTSFGGNLGRAVFQAKKRVLEPLGLVEEGAKTAPGKKRPVEPSPQRSPDSSTGIGKKGQQPARKRLNFGQTGDSESVPDPQPIGEPPAGPSGLG |
| | 201                                                        ◊   ◊       ◊                          300 |
| AAV1 (200) | PTTMASGGGAPMADNNEGADGVGNASGNWHCDSTWLGDRVITTSTRTWALPTYNNHLYKQISSAST-GASNDNHYFGYSTPWGYFDFNRFHCHFSPRDWQ |
| AAV2 (200) | TNTMATGSGAPMADNNEGADGVGNSSGNWHCDSTWMGDRVITTSTRTWALPTYNNHLYKQISSQS--GASNDNHYFGYSTPWGYFDFNRFHCHFSPRDWQ |
| AAV3 (200) | SNTMASGGGAPMADNNEGADGVGSSSGNWHCDSQWLGDRVITTSTRTWALPTYNNHLYKQISSQS--GASNDNHYFGYSTPWGYFDFNRFHCHFSPRDWQ |
| AAV4 (196) | EMRAAAGGAAVEGG--QGADGVGNASGDWHCDSTWSEGHVTTTSTRTWVLPTYNNHLYKRLGESLQ-----SNTYNGFSTPWGYFDFNRFHCHFSPRDWQ |
| AAV5 (190) | ADTMSAGGGGPLGDNNQGADGVGNASGDWHCDSTWMGDRVVTKSTRTWVLPSYNNHQYREIKSGS-VDGSNANAYFGYSTPWGYFDFNRFHSHWSPRDWQ |
| AAV6 (200) | PTTMASGGGAPMADNNEGADGVGNASGNWHCDSTWLGDRVITTSTRTWALPTYNNHLYKQISSAST-GASNDNHYFGYSTPWGYFDFNRFHCHFSPRDWQ |
| AAV7 (201) | SGTVAAGGGANPMADNNEGADGVGSSSGNWHCDSTWLGDRVITTSTRTWALPTYNNHLYKQISSETAG-STNDNTYFGYSTPWGYFDFNRFHCHFSPRDWQ |
| AAV8 (201) | PNTMAAGGGAPMADNNEGADGVGSSSGNWHCDSTWLGDRVITTSTRTWALPTYNNHLYKQISNGTSGGATNDNTYFGYSTPWGYFDFNRFHCHFSPRDWQ |
| AAV9 (200) | SLTMASGGAPVADNNEGADGVGSSSGNWHCDSQWLGDRVITTSTRTWALPTYNNHLYKQISNSTSGGSSNDNAYFGYSTPWGYFDFNRFHCHFSPRDWQ |
| AAV10 (201) | SGTMAAGGGAPMADNNEGADGVGSSSGNWHCDSTWLGDRVITTSTRTWALPTYNNHLYKQISNGTSGGSTNDNTYFGYSTPWGYFDFNRFHCHFSPRDWQ |

FIG. 2D-1

```
                                                                                                           400
              301                                                     ◇
AAV1  (299)   RLINNNWGFRPKRLNFKLFNIQVKEVTTNDGVTTIANNLTSTVQVFSDSEYQLPYVLGSAHQGCLPPFPADVFMIPQYGYLTLNNGSQA---VGRSSFYC
AAV2  (298)   RLINNNWGFRPKRLNFKLFNIQVKEVTQNDGTTIANNLTSTVQVFTDSEYQLPYVLGSAHQGCLPPFPADVFMVPQYGYLTLNNGSQA---VGRSSFYC
AAV3  (298)   RLINNNWGFRPKKLSFKLFNIQVRGVTQNDGTTIANNLTSTVQVFTDSEYQLPYVLGSAHQGCLPPFPADVFMVPQYGYLTLNNGSQA---VGRSSFYC
AAV4  (289)   RLINNNWGMRPKAMRVKIFNIQVKEVTTSNGETTVANNLTSTVQIFADSSYELPYVMDAGQEGSLPPFPNDVFMVPQYGYCGLVTGNTSQQTDRNAFYC
AAV5  (289)   RLINNYWGFRPRSLRVKIFNIQVKEVTVQDSTTIANNLTSTVQVFTDDDYQLPYVVGNGTEGCLPAFPQVFTLPQYGYATLNRDNTEN-PTERSSFFC
AAV6  (299)   RLINNNWGFRPKRLNFKLFNIQVKEVTTNDGVTTIANNLTSTVQVFSDSEYQLPYVLGSAHQGCLPPFPADVFMIPQYGYLTLNNGSQA---VGRSSFYC
AAV7  (300)   RLINNNWGFRPKKLRFKLRFNIQVKEVTTNDGVTTIANNLTSTIQVFDSEYQLPYVLGSAHQGCLPPFPADVFMIPQYGYLTLNNGSQS---VGRSSFYC
AAV8  (301)   RLINNNWGFRPKRLSFKLFNIQVKEVTQNEGTKTIANNLTSTIQVFTDSYQLPYVLGSAHQGCLPPFPADVFMIPQYGYLTLNNGSQA---VGRSSFYC
AAV9  (300)   RLINNNWGFRPKRLNFKLFNIQVKEVTDNNGVKTIANNLTSTVQVFTDSDYQLPYVLGSAHEGCLPPFPADVFMIPQYGYLTLNDGSQA---VGRSSFYC
AAV10 (301)   RLINNNWGFRPKRLNFKLFNIQVKEVTQNEGTKTIANNLTSTIQVFTDSEYQLPYVLGSAHQGCLPPFPADVFMIPQYGYLTLNNGSQA---VGRSSFYC
                                                                                                          ◇ 500
              401
AAV1  (396)   LEYFPSQMLRTGNNFTFSYTFEEVPFHSSYAHSQSLDRLMNPLIDQYLYYLNRTQ-NQSGSAQNKDLLFSRGSPAGMSVQPKNWLPGPCYRQQRVSKTKT
AAV2  (395)   LEYFPSQMLRTGNNFTFSYTFEDVPFHSSYAHSQSLDRLMNPLIDQYLYYLSRTN-TPSGTTTQSRLQFSQAGASDIRDQSRNWLPGPCYRQQRVSKTSA
AAV3  (395)   LEYFPSQMLRTGNNFQFSYTFEDVPFHSSYAHSQSLDRLMNPLIDQYLYYLNRTQGTTSGTTNQSRLLFSQAGPQSMSLQARNWLPGPCYRQQRLSKTAN
AAV4  (389)   LEYFPSQMLRTGNNFEITYSFEKVPFHSMYAHSQSLDRLMNPLIDQYLWGLQSTTTGTTLNAGTATNFTKLRPTNFSNFKKNWLPGPSIKQQGFSKTAN
AAV5  (388)   LEYFPSKMLRTGNNFEFTYNFEEVPFHSSYAHSQSLDRLFKLANPLVDQYLRFVSTN-------NTGGVQFNKNLAGRYANTYKNWFGPMGRTQGWNLGSG
AAV6  (396)   LEYFPSQMLRTGNNFTFSYTFEDVPFHSSYAHSQSLDRLMNPLIDQYLYYLNRTQ-NQSGSAQNKDLLFSRGSPAGMSVQPKNWLPGPCYRQQRVSKTKT
AAV7  (397)   LEYFPSQMLRTGNNFEFSYSFEDVPFHSSYAHSQSLDRLMNPLIDQYLYYLARTQSNPGGTAGNRELQFYQGGPSTMAEQAKNWLPGPCFRQQRVSKTLD
AAV8  (398)   LEYFPSQMLRTGNNFQFTYTFEDVPFHSSYAHSQSLDRLMNPLIDQYLYYLSRTQTT-GGTANTQTLGFSQGGPNTMANQAKNWLPGPCYRQQRVSTTTG
AAV9  (397)   LEYFPSQMLRTGNNFQFSYEFENVPFHSSYAHSQSLDRLMNPLIDQYLYYLSKTING--SQONQQTLKFSVAGPSNMAVQGRNYIPGPSYRQQRVSTTVT
AAV10 (398)   LEYFPSQMLRTGNNFEFSYQFEDVPFHSSYAHSQSLDRLMNPLIDQYLYYLSRTQST-GGTAGTQQLLFSQAGPNNMSAQAKNWLPGPCYRQQRVSTTLS
                                                                                                          ◇* 600
              501
AAV1  (495)   DN------NNSNFTWTGASKYNLNGRESIINPGTAMASHKDDEDKFFPMSGVMIFGKE---SAGASNTALDNVMITDEEEIKATNPVATERFGTVAVNFQS
AAV2  (494)   DN------NNSEYSWTGATKYHLNGRDSLVNPGPAMASHKDDEEKFFPQSGVLIFGKQ---GSEKTNVDIEKVMITDEEEIRTTNPVATEQYGSVSTNLQR
AAV3  (495)   DN------NNSNFPWTAASKYHLNGRDSLVNPGPAMASHKDDEEKFFPMHGNLIFGKE---GTTASNAELDNVMITDEEEIRTTNPVATEQYGTVANNLQS
AAV4  (489)   QNYKIPATGSDSLIKYETHSTLDGRWSALTPGPPMATAGPADSKFS-NSQLIFAGPK---QNGNTATVPGTLIFTSEEELAATNATDTDMWGNLPGGDQS
AAV5  (481)   VN------RASVSAFATTNRMELEGASYQVPPQPNGMTNNLQGSNTYALENTMIFNSQPANPGTTATYLEGNMLITSESETQPVNRVAYNVGGQMATNNQS
AAV6  (495)   DN------NNSNFTWTGASKYNLNGRESIINPGTAMASHKDDRDKFFPMSGVMIFGKE---SAGASNTALDNVMITDEEEIKATNPVATERFGTVAVNLQS
AAV7  (497)   QN------NNSNFAWTGATKYHLNGRNSLANPGIAMATHKDDEERFFPSNGILIFGKT---GATNKTTLENVLMTNEEEIRPTNPVATEEYGIVSSNLQA
AAV8  (495)   QN------NNSNFAWTAGTKYHLNGRNSLMNPGPAMASHKEGEDRFFPLSGSLIFGKQ---NAARDNADYSDVMLTSEEEIKTTNPVATEEYGIVADNLQQ
AAV9  (495)   QN------NNSEFAWPGASSWALNGRNSLMNPGPAMASHKEGEDRFFPLSGSLIFGKQ---GTGRDNVDADKVMITNEEEIKTTNPVATESYGVATNHQS
AAV10 (497)   QN------NNSNFAWTGATKYHLNGRDSLVNPGVAMATHKDDEEERFFPSSGVLMFGKQ---GAGKDNVDYSSVMLTSEEEIKTTNPVATEQYGVVADNLQQ
```

FIG. 2D-2

```
        601       *         ◇            ◇*        ◇     ◇      *                    700
AAV1 (587) SSTDPATGDVHAMGALPGMVWQDRDVYLQGPIWAKIPHTDGHFHPSPLMGGFGLKNPPPQILIKNTPVPANPPAEFSATKFASFITQYSTGQVSVEIEWE
AAV2 (586) GNRQAATADVNTQGVLPGMVWQDRDVYLQGPIWAKIPHTDGHFHPSPLMGGFGLKHPPPQILIKNTPVPANPSTTFSAAKFASFITQYSTGQVSVEIEWE
AAV3 (587) SNTAPTTGTVNHQGALPGMVWQDRDVYLQGPIWAKIPHTDGHFHPSPLMGGFGLKHPPPQIMKNTPVPANPPTTFSPAKFASFITQYSTGQVSVEIEWE
AAV4 (585) NSNLPTVDRLTALGAVPGMVWQNRDIYYQGPIWAKIPHTDGHFHPSPLIGGFGLKHPPPQIFIKNTPVPANPATTFSSTPVNSFITQYSTGQVSVQIDWE
AAV5 (576) STTAPATGTYNLQEIVPGSVWMERDVYLQGPIWAKIPETGAHFHPSPAMGGFGLKHPPPMLIKNTPVPGN-ITSFSDVPVSSFITQYSTGQVTVEMEWE
AAV6 (587) SSTDPATGDVHVMGALPGMVWQDRDVYLQGPIWAKIPHTDGHFHPSPLMGGFGLKHPPPQILIKNTPVPANPPAEFSATKFASFITQYSTGQVSVEIEWE
AAV7 (588) ANTAAQTQVVNNQGALPGMVWQNRDVYLQGPIWAKIPHTDGNFHPSPLMGGFGLKHPPPQILIKNTPVPANPPEVFTPAKFASFITQYSTGQVSVEIEWE
AAV8 (589) QNTAPQIGTVNSQGALPGMVWQNRDVYLQGPIWAKIPHTDGNFHPSPLMGGFGLKHPPPQILIKNTPVPADPPTTFNQSKLNSFITQYSTGQVSVEIEWE
AAV9 (587) AQAQAQTGWVQNQGILPGMVWQNRDVYLQGPIWAKIPHTDGNFHPSPLMGGFGMKHPPPQILIKNTPVPADPPTAFNKDKLNSFITQYSTGQVSVEIEWE
AAV10 (589) QNAAPIVGAVNSQGALPGMVWQNRDVYLQGPIWAKIPHTDGNFHPSPLMGGFGLKHPPPQILIKNTPVPADPPTTFSQAKLASFITQYSTGQVSVEIEWE

701          *      ◇   *     ◇                751
AAV1 (687) LQKENSKRWNPEVQYTSNYAKSANVDFTVDNNGLYTEPRPIGTRYLTRPL- SEQ ID NO:1
AAV2 (686) LQKENSKRWNPEIQYTSNYNKSVNVDFTVDTNGVYSEPRPIGTRYLTRNL- SEQ ID NO:2
AAV3 (687) LQKENSKRWNPEIQYTSNYNKSVNVDFTVDTNGVYSEPRPIGTRYLTRNL- SEQ ID NO:3
AAV4 (685) IQKERSKRWNPEVQFTSNYGQQNSLLWAPDAAGKYTEPRAIGTRYLTHHL- SEQ ID NO:4
AAV5 (675) LKKENSKRWNPEIQYTNNYNDPQFVDFAPDSTGEYRTTRPIGTRYLTRPL- SEQ ID NO:5
AAV6 (687) LQKENSKRWNPEVQYTSNYAKSANVDFTVDNNGLYTEPRPIGTRYLTRPL- SEQ ID NO:6
AAV7 (688) LQKENSKRWNPEIQYTSNYNFEKQTGVDFAVDSQGVYSEPRPIGTRYLTRNL- SEQ ID NO:7
AAV8 (689) LQKENSKRWNPEIQYTSNYYKSTSVDFAVNTEGVYSEPRPIGTRYLTRNL- SEQ ID NO:8
AAV9 (687) LQKENSKRWNPEIQYTSNYYKSNNVEFAVNTEGVYSEPRPIGTRYLTRNL- SEQ ID NO:9
AAV10 (689) LQKENSKRWNPEIQYTSNYYKSTNVDFAVNTDGTYSEPRPIGTRYLTRNL- SEQ ID NO:10
```

FIG. 2D-3

| MUTANT | PACKAGING EFFICIENCY | TRANSDUCTION EFFICIENCY |
|---|---|---|
| AAV2-S261V | ~10-FOLD LOWER | -* |
| AAV2-S264V | NO CHANGE | -* |
| AAV2-S267V | NO DNAse I- RESISTANT PARTICLES | -* |
| AAV2-S276V | ~10-FOLD LOWER | -* |
| AAV2-S384V | ~3-FOLD HIGHER | ~10-FOLD LOWER |
| AAV2-S458V | NO CHANGE | ~4-FOLD HIGHER |
| AAV2-S468V | ~5-FOLD HIGHER | NO CHANGE |
| AAV2-S492V | NO CHANGE | ~2-FOLD HIGHER |
| AAV2-S498V | NO CHANGE | ~10-FOLD LOWER |
| AAV2-S578V | NO CHANGE | ~10-FOLD LOWER |
| AAV2-S658V | ~10-FOLD LOWER | -* |
| AAV2-S662V | NO CHANGE | ~25-FOLD HIGHER |
| AAV2-S668V | NO DNAse I- RESISTANT PARTICLES | -* |
| AAV2-S707V | NO CHANGE | ~10-FOLD LOWER |
| AAV2-S721V | NO CHANGE | NO CHANGE |

*FIG. 5*

| MUTANT | PACKAGING EFFICIENCY | TRANSDUCTION EFFICIENCY |
|---|---|---|
| AAV2-S662V | NO CHANGE | ~25-FOLD HIGHER |
| AAV2-S662A | ~5-FOLD HIGHER | ~3-FOLD HIGHER |
| AAV2-S662D | NO CHANGE | ~8-FOLD HIGHER |
| AAV2-S662F | ~10-FOLD LOWER | NO CHANGE |
| AAV2-S662H | NO CHANGE | ~4-FOLD HIGHER |
| AAV2-S662N | ~10-FOLD LOWER | NO CHANGE |
| AAV2-S662L | ~10-FOLD LOWER | NO CHANGE |
| AAV2-S662I | ~10-FOLD LOWER | NO CHANGE |

*FIG. 7*

WT-AAV2
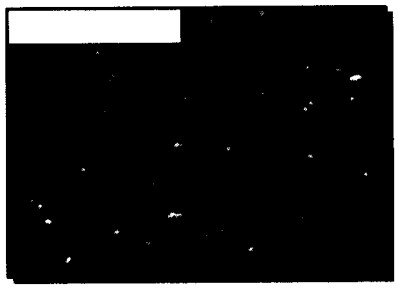
AAV2-S458V
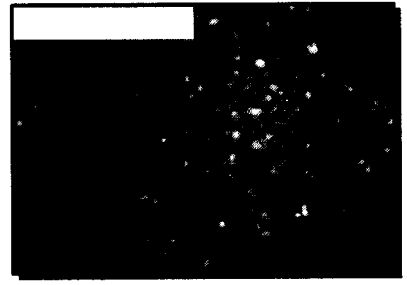
AAV2-S578V
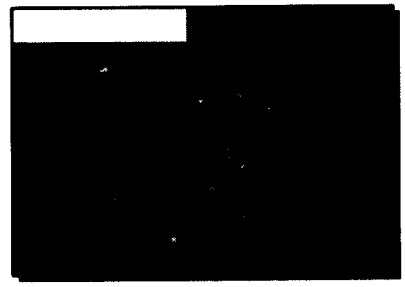
AAV2-S662V
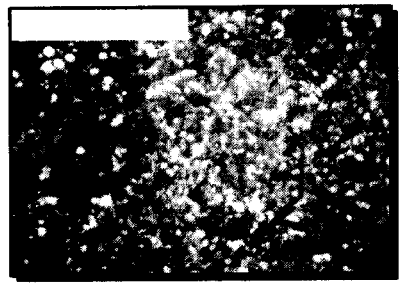
AAV2-S668V
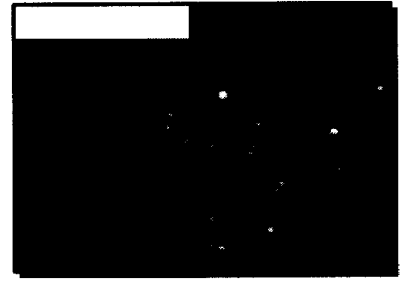
*FIG. 11A*

WT-AAV2
AAV2-T455V
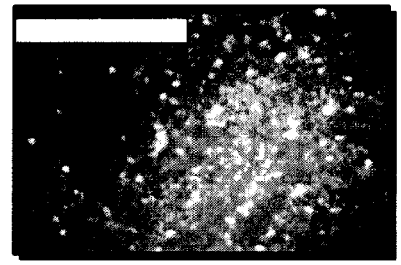
AAV2-T491V
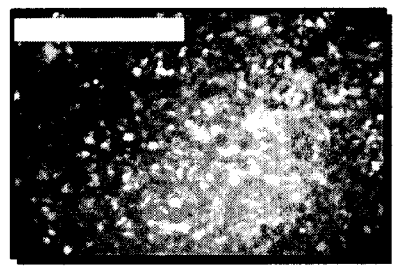
AAV2-T659V
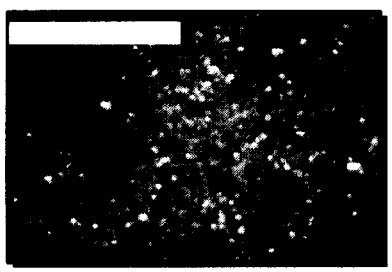
AAV2-T671V
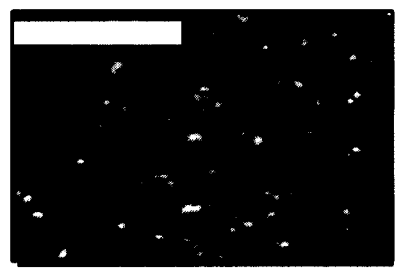
*FIG. 12A*

| WT-AAV2 | T491+550+659V | Y444+500+730F |
|---|---|---|
| 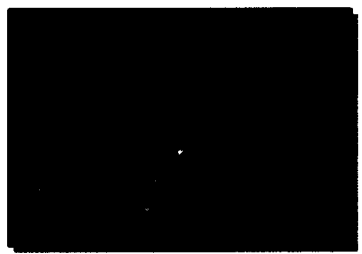 | 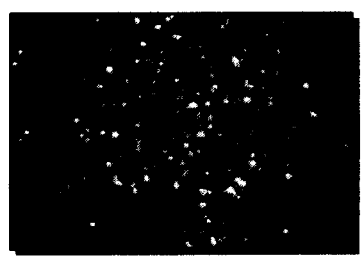 | 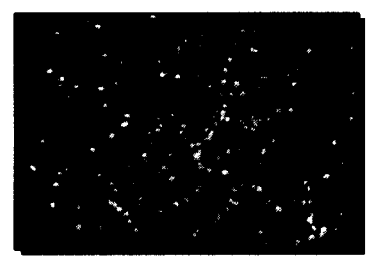 |
| Y444+500+730F T491V | Y444+500+730F S662+T491V | Y444+500+730F T491+550V |
|  | 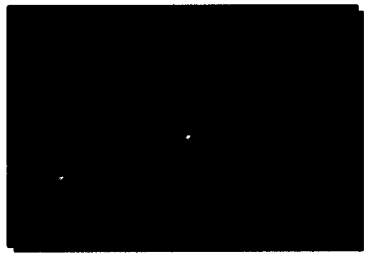 |  |
*FIG. 13A*

MOCK

WT-AAV8

K530E-AAV8

K547E-AAV8

K569-AAV8E

WT-AAV2
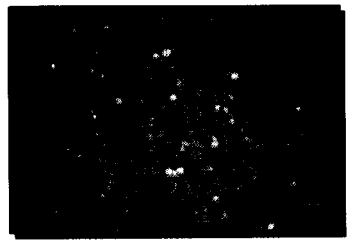
Y444+500+730F
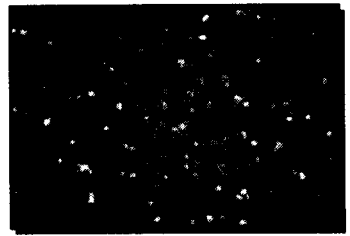
**Y444+500+730F
T491V**
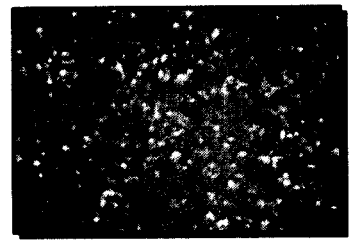
T491+550+659V
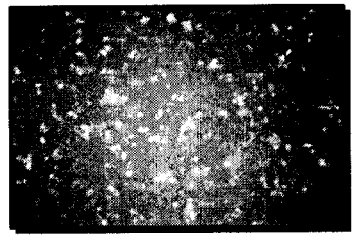
S662V
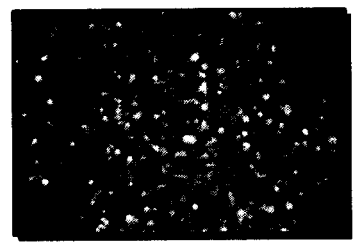
T491V+S662V
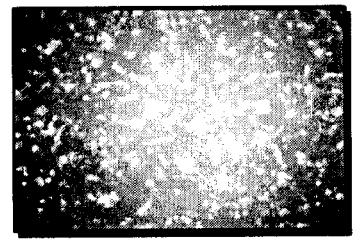
*FIG. 19A*

MOCK WT
 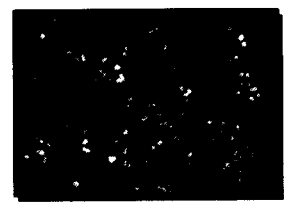
FIG. 21A  FIG. 21B
K258E  K490E  K527E  K532E
 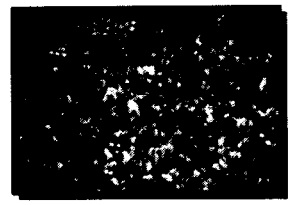  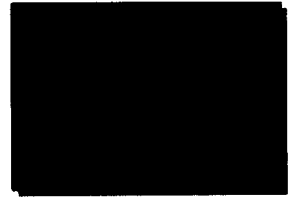
FIG. 21C  FIG. 21D  FIG. 21E  FIG. 21F
K544E  K549E  K556E
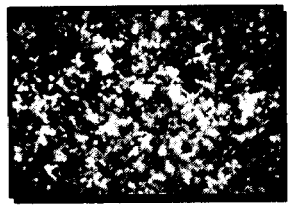 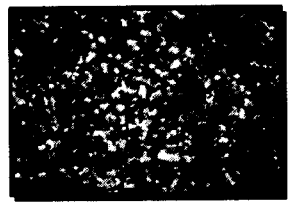 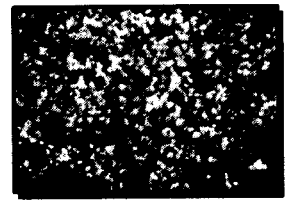
FIG. 21G  FIG. 21H  FIG. 21I MOCK WT
FIG. 22A  FIG. 22B
K258E  K490E  K527E  K532E
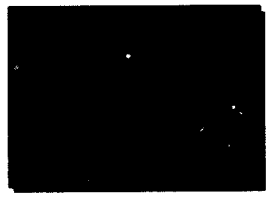
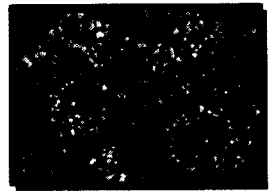
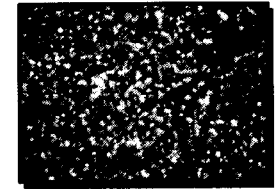
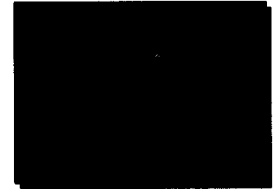
FIG. 22C  FIG. 22D  FIG. 22E  FIG. 22F
K544E  K549E  K556E
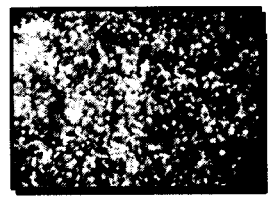
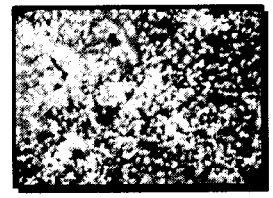
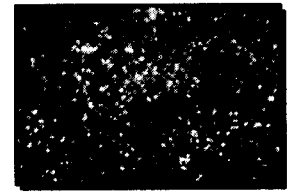
FIG. 22G  FIG. 22H  FIG. 22I

HIGH-TRANSDUCTION-EFFICIENCY rAAV VECTORS, COMPOSITIONS, AND METHODS OF USE

CROSS-REFERENCE TO RELATED APPLICATIONS

The present application is a continuation of U.S. application Ser. No. 16/283,705, filed Feb. 22, 2019, entitled "HIGH-TRANSDUCTION-EFFICIENCY RAAV VECTORS, COMPOSITIONS, AND METHODS OF USE", which is a divisional of U.S. application Ser. No. 15/444,235, filed Feb. 27, 2017, now U.S. Pat. No. 10,294,281 and entitled "HIGH-TRANSDUCTION-EFFICIENCY RAAV VECTORS, COMPOSITIONS, AND METHODS OF USE", which is a divisional of U.S. application Ser. No. 14/401,442, filed Nov. 14, 2014, now U.S. Pat. No. 9,611,302 and entitled "HIGH-TRANSDUCTION-EFFICIENCY RAAV VECTORS, COMPOSITIONS, AND METHODS OF USE", which is a 35 U.S.C. § 371 National Phase Application of International Application No. PCT/US2013/041234, filed May 15, 2013 and entitled "HIGH-TRANSDUCTION-EFFICIENCY RAAV VECTORS, COMPOSITIONS, AND METHODS OF USE" which a continuation-in-part of U.S. patent application Ser. No. 13/840,224, filed Mar. 15, 2013, now U.S. Pat. No. 9,725,485 and entitled "AAV VECTORS WITH HIGH TRANSDUCTION EFFICIENCY AND USES THEREOF FOR GENE THERAPY", and which claims the priority benefit under 35 U.S.C. § 119(e) of U.S. Provisional Application Ser. No. 61/647,318, filed May 15, 2012. U.S. patent application Ser. No. 13/840,224 claims the priority benefit under 35 U.S.C. § 119(e) of U.S. Provisional Application Ser. No. 61/647,318, filed May 15, 2012. The content of each of the aforementioned applications is hereby incorporated in its entirety by express reference thereto.

STATEMENT REGARDING FEDERALLY SPONSORED RESEARCH OR DEVELOPMENT

This invention was made with government support under grant number HL097088, awarded by the National Institutes of Health. The government has certain rights in the invention.

BACKGROUND OF THE INVENTION

The contents of the electronic sequence listing U120270045US06-SUBSEQ-COB.xml; Size: 20.625 bytes; and Date of Creation: Aug. 26, 2022) are herein incorporated by reference in their entirety.

FIELD OF THE INVENTION

Major advances in the field of gene therapy have been achieved by using viruses to deliver therapeutic genetic material. The adeno-associated virus (AAV) has attracted considerable attention as a highly effective viral vector for gene therapy due to its low immunogenicity and ability to effectively transduce non-dividing cells. AAV has been shown to infect a variety of cell and tissue types, and significant progress has been made over the last decade to adapt this viral system for use in human gene therapy.

In its normal "wild type" form, recombinant AAV (rAAV) DNA is packaged into the viral capsid as a single stranded molecule about 4600 nucleotides (nt) in length. Following infection of the cell by the virus, the molecular machinery of the cell converts the single DNA strand into a double-stranded form.

AAV has many properties that favor its use as a gene delivery vehicle: 1) the wild type virus is not associated with any pathologic human condition; 2) the recombinant form does not contain native viral coding sequences; and 3) persistent transgenic expression has been observed in many applications. One of the main obstacles of the gene therapy, the induction of immuno-competition in cellular immune responses against vector-derived and transgene-derived epitopes, can be overcome by replication-deficiency and lack of viral proteins expressed by recombinant AAV.

The transduction efficiency of recombinant adeno-associated virus vectors varies greatly in different cells and tissues in vitro and in vivo. Systematic studies have been performed to elucidate the fundamental steps in the life cycle of AAV. For example, it has been documented that a cellular protein, FKBP52, phosphorylated at tyrosine residues by epidermal growth factor receptor protein tyrosine kinase (EGFR-PTK), inhibits AAV second-strand DNA synthesis and consequently, transgene expression in vitro as well as in vivo. It has also been demonstrated that EGFR-PTK signaling modulates the ubiquitin/proteasome pathway-mediated intracellular trafficking as well as FKBP52-mediated second-strand DNA synthesis of AAV vectors. In those studies, inhibition of EGFR-PTK signaling led to decreased ubiquitination of AAV capsid proteins, which in turn, facilitated nuclear transport by limiting proteasome-mediated degradation of AAV vectors, implicating EGFR-PTK-mediated phosphorylation of tyrosine residues on AAV capsids.

BRIEF SUMMARY OF THE INVENTION

The present invention provides AAV capsid proteins comprising modification of one or a combination of the surface-exposed lysine, serine, threonine and/or tyrosine residues in the VP3 region. Also provided are rAAV virions that comprise the AAV capsid proteins of the present invention, as well as nucleic acid molecules and rAAV vectors encoding the AAV capsid proteins of the present invention. Advantageously, the rAAV vectors and virions of the present invention have improved efficiency in transduction of a variety of cells, tissues and organs of interest, when compared to wild-type rAAV vectors and virions.

In one embodiment, the present invention provides a nucleic acid molecule comprising a nucleotide sequence encoding an AAV capsid protein, wherein the VP3 region of the AAV capsid protein comprises a non-lysine residue at a position that corresponds to a lysine residue in the VP3 region of the capsid protein of the wild-type AAV [e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10; and in one embodiment, preferably the capsid protein of wild-type AAV2 (SEQ ID NO:2)], wherein the lysine residue in the VP3 region of the wild-type AAV protein is one or more of K258, K321, K459, K490, K507, K527, K572, K532, K544, K549, K556, K649, K655, K665, and K706, or any combination thereof.

In one embodiment, the surface-exposed lysine residue corresponding K532 of the wild-type AAV2 capsid sequence is modified. In one embodiment, the surface-exposed lysine residue of the AAV capsid is modified into glutamic acid (E) or arginine (R). In specific embodiments, the surface-exposed lysine residue corresponding K532 of the wild-type AAV2 capsid sequence is modified into arginine (K532R).

In certain embodiments, one or more surface-exposed lysine residues corresponding to K490, K544, K549, and K556 of the wild-type AAV2 capsid sequence are modified. In certain specific embodiments, one or more surface-exposed lysine residue corresponding K490, K544, K549, and K556 of the wild-type AAV2 capsid sequence are modified into glutamic acid (E).

In one embodiment, the present invention provides AAV2 vectors wherein surface-exposed lysine residues corresponding to K544 and K556 residues of the wild-type AAV2 capsid are modified into glutamic acid (E).

In certain embodiments, one or more surface-exposed lysine residues corresponding to K530, K547, and K569 of the wild-type AAV8 capsid sequence are modified. In certain specific embodiments, one or more surface-exposed lysine residue corresponding K530, K547, and K569 of the wild-type AAV2 capsid sequence are modified into glutamic acid (E).

In one embodiment, a combination of surface-exposed lysine, serine, threonine and/or tyrosine residues of the AAV capsid is modified, wherein the modification occurs at positions corresponding to
(Y444F+Y500F+Y730F+T491V)
(Y444F+Y500F+Y730F+T491V+T550V)
(Y444F+Y500F+Y730F+T491V+T659V)
(T491V+T550V+T659V)
(Y440F+Y500F+Y730F)
(Y444F+Y500F+Y730F+T491V+S662V), and/or
(Y444F+Y500F+Y730F+T491V+T550V+T659V)
of the wild-type AAV capsid sequence [e.g., one or more of SEQ ID NOs:1-10; and in a particular embodiment, of the capsid protein of wild-type AAV2 sequence (SEQ ID NO:2)].

In related embodiments, the invention provides methods for using the vectors and compositions disclosed herein, and further provides processes for the transduction of one or more cells, one or more tissues, and/or one or more organs of interest, and particularly those of a mammalian animal using the disclosed viral vector constructs. In an overall and general sense, such methods generally include at least the step of introducing into a suitable host cell of interest, at least a first composition that comprises, consists essentially of, or alternatively consists of, an effective amount of a rAAV vector and/or an infectious AAV viral particle, or recombinant AAV virion of present invention in an amount and for a time sufficient to transform at least a first cell or a first population of cells with the viral vector. In particular embodiments, the vectors, virions, or infectious viral particles of the present invention are preferably useful as vectors for introducing one or more nucleic acid segments to a selected host cell of interest. Preferably the host cell is a mammalian host cell, with human host cells being particularly preferred as targets for the recombinant vectors and virions described herein. In certain embodiments, such vectors will further comprise one or more isolated DNA segments encoding a selected therapeutic and/or diagnostic agent, including, for example one or more polynucleotides comprising one or more genes of interest that are capable of being expressed in a mammalian host cell that has been transformed by one or more of the vectors, viruses, or infectious virions described and provided herein.

In one aspect, the invention further provides compositions comprising recombinant adeno-associated viral (AAV) vectors, virions, viral particles, and pharmaceutical formulations thereof, useful in methods for delivering genetic material encoding one or more beneficial or therapeutic product(s) to mammalian cells and tissues. In particular, the compositions and methods of the invention provide a significant advancement in the art through their use in the treatment, prevention, and/or amelioration of symptoms of one or more mammalian diseases. It is contemplated that human gene therapy will particularly benefit from the present teachings by providing new and improved viral vector constructs for use in the treatment of a number of diverse diseases, disorders, and dysfunctions.

In another aspect, the invention concerns modified rAAV vector that encode one or more mammalian therapeutic agents for the prevention, treatment, and/or amelioration of one or more disorders in the mammal into which the vector construct is delivered. In particular, the invention provides rAAV-based expression constructs that encode one or more mammalian therapeutic agent(s) (including, but not limited to, for example, protein(s), polypeptide(s), peptide(s), enzyme(s), antibodies, antigen binding fragments, as well as variants, and/or active fragments thereof, for use in the treatment, prophylaxis, and/or amelioration of one or more symptoms of a mammalian disease, dysfunction, injury, and/or disorder.

In another embodiment, the invention concerns genetically modified rAAV vectors that comprise at least a first nucleic acid segment that encodes one or more therapeutic agents that alter, inhibit, reduce, prevent, eliminate, or impair the activity of one or more endogenous biological processes in the cell. In particular embodiments, such therapeutic agents may be those that selectively inhibit or reduce the effects of one or more metabolic processes, dysfunctions, disorders, or diseases. In certain embodiments, the defect may be caused by injury or trauma to the mammal for which treatment is desired. In other embodiments, the defect may be caused the over-expression of an endogenous biological compound, while in other embodiments still; the defect may be caused by the under-expression or even lack of one or more endogenous biological compounds.

When the use of such vectors is contemplated for introduction of one or more exogenous proteins, polypeptides, peptides, ribozymes, siRNAs, and/or antisense oligonucleotides, to a particular cell transfected with the vector, one may employ the modified AAV vectors disclosed herein by incorporating into the vector at least a first exogenous polynucleotide operably positioned downstream and under the control of at least a first heterologous promoter that expresses the polynucleotide in a cell comprising the vector to produce the encoded therapeutic agent, including for example, peptides, proteins, polypeptides, antibodies, ribozymes, siRNAs, and antisense oligo- or polynucleotides. Such constructs may employ one or more heterologous promoters to express the therapeutic agent of interest. Such promoters may be constitutive, inducible, or even cell- or tissue-specific. Exemplary promoters include, but are not limited to, a CMV promoter, a β-actin promoter, a hybrid CMV promoter, a hybrid β-actin promoter, an EF1 promoter, a U1a promoter, a U1b promoter, a Tet-inducible promoter, a VP16-LexA promoter, a joint-specific promoter and a human-specific promoter.

The genetically-modified rAAV vectors or expression systems of the invention may also further comprise a second nucleic acid segment that comprises, consists essentially of, or consists of, one or more enhancers, regulatory elements, transcriptional elements, to alter or effect transcription of the heterologous gene cloned in the rAAV vectors. For example, the rAAV vectors of the present invention may further comprise a second nucleic acid segment that comprises, consists essentially of, or consists of, at least a first CMV enhancer, a synthetic enhancer, or a cell- or tissue-specific enhancer. The second nucleic acid segment may also further comprise, consist essentially of, or consist of one or more intron sequences, post-transcriptional regulatory elements, or such like. The vectors and expression systems of the invention may also optionally further comprise a third nucleic acid segment that comprises, consists essentially of, or consists of, one or more polylinker or multiple restriction sites/cloning region(s) to facilitate insertion of one or more selected genetic elements, polynucleotides, and the like into the rAAV vectors at a convenient restriction site.

In aspects of the invention, the exogenous polynucleotides that are comprised within one or more of the improved rAAV vectors disclosed herein are preferably of mammalian origin, with polynucleotides encoding polypeptides and peptides of human, primate, murine, porcine, bovine, ovine, feline, canine, equine, epine, caprine, or lupine origin being particularly preferred.

As described above, the exogenous polynucleotide will preferably encode one or more proteins, polypeptides, peptides, enzymes, antibodies, siRNAs, ribozymes, or antisense polynucleotides, oligonucleotides, PNA molecules, or a combination of two or more of these therapeutic agents. In fact, the exogenous polynucleotide may encode two or more such molecules, or a plurality of such molecules as may be desired. When combinational gene therapies are desired, two or more different molecules may be produced from a single rAAV expression system, or alternatively, a selected host cell may be transfected with two or more unique rAAV expression systems, each of which may comprise one or more distinct polynucleotides that encode a therapeutic agent.

In other embodiments, the invention also provides genetically-modified rAAV vectors that are comprised within an infectious adeno-associated viral particle or a virion, or pluralities of such particles, which themselves may also be comprised within one or more diluents, buffers, physiological solutions or pharmaceutical vehicles, formulated for administration to a mammal such as a human for therapeutic, and/or prophylactic gene therapy regimens. Such vectors, virus particles, virions, and pluralities thereof may also be provided in excipient formulations that are acceptable for veterinary administration to selected livestock, exotic or domesticated animals, companion animals (including pets and such like), as well as non-human primates, zoological or otherwise captive specimens, and such like, wherein the use of such vectors and related gene therapy is indicated to produce a beneficial effect upon administration to such an animal.

The invention also concerns host cells that comprise at least one of the disclosed rAAV vectors, virus particles, or virions. Such host cells are particularly mammalian host cells, with human host cells being particularly highly preferred, and may be either isolated, in cell or tissue culture. In the case of genetically modified animal models, the transformed host cells may even be comprised within the body of a non-human animal itself.

In certain embodiments, the creation of recombinant non-human host cells, and/or isolated recombinant human host cells that comprise one or more of the disclosed rAAV vectors is also contemplated to be useful for a variety of diagnostic, and laboratory protocols, including, for example, means for the production of large-scale quantities of the rAAV vectors described herein. Such virus production methods are particularly contemplated to be an improvement over existing methodologies including in particular, those that require very high titers of the viral stocks in order to be useful as a gene therapy tool. The inventors contemplate that one very significant advantage of the present methods will be the ability to utilize lower titers of viral particles in mammalian transduction protocols, yet still retain transfection rates at a suitable level.

Compositions comprising one or more of the disclosed rAAV vectors, expression systems, infectious AAV particles, or host cells also form part of the present invention, and particularly those compositions that further comprise at least a first pharmaceutically-acceptable excipient for use in therapy, and for use in the manufacture of medicaments for the treatment of one or more mammalian diseases, disorders, dysfunctions, or trauma. Such pharmaceutical compositions may optionally further comprise one or more diluents, buffers, liposomes, a lipid, a lipid complex; or the tyrosine-modified rAAV vectors may be comprised within a microsphere or a nanoparticle. Pharmaceutical formulations suitable for intramuscular, intravenous, or direct injection into an organ or tissue or a plurality of cells or tissues of a human or other mammal are particularly preferred, however, the compositions disclosed herein may also find utility in administration to discreet areas of the mammalian body, including for example, formulations that are suitable for direct injection into one or more organs, tissues, or cell types in the body. Such injection sites include, but are not limited to, the brain, a joint or joint capsule, a synovium or sub-synovium tissue, tendons, ligaments, cartilages, bone, peri-articular muscle or an articular space of a mammalian joint, as well as direct administration to an organ such as the heart, liver, lung, pancreas, intestine, brain, bladder, kidney, or other site within the patient's body, including, for example, introduction of the viral vectors via intraabdominal, intrathoracic, intravascular, or intracerebroventricular delivery.

Other aspects of the invention concern recombinant adeno-associated virus virion particles, compositions, and host cells that comprise, consist essentially of, or consist of, one or more of the rAAV vectors disclosed herein, such as for example pharmaceutical formulations of the vectors intended for administration to a mammal through suitable means, such as, by intramuscular, intravenous, intra-articular, or direct injection to one or more cells, tissues, or organs of a selected mammal. Typically, such compositions may be formulated with pharmaceutically-acceptable excipients as described hereinbelow, and may comprise one or more liposomes, lipids, lipid complexes, microspheres or nanoparticle formulations to facilitate administration to the selected organs, tissues, and cells for which therapy is desired.

Kits comprising one or more of the disclosed rAAV vectors, virions, viral particles, transformed host cells or pharmaceutical compositions comprising such; and instructions for using the kit in a therapeutic, diagnostic, or clinical embodiment also represent preferred aspects of the present disclosure. Such kits may further comprise one or more reagents, restriction enzymes, peptides, therapeutics, pharmaceutical compounds, or means for delivery of the composition(s) to host cells, or to an animal (e.g., syringes, injectables, and the like). Such kits may be therapeutic kits for treating, preventing, or ameliorating the symptoms of a disease, deficiency, dysfunction, and/or injury, and may comprise one or more of the modified rAAV vector constructs, expression systems, virion particles, or a plurality of such particles, and instructions for using the kit in a therapeutic and/or diagnostic medical regimen. Such kits may also be used in large-scale production methodologies to produce large quantities of the viral vectors themselves (with or without a therapeutic agent encoded therein) for commercial sale, or for use by others, including e.g., virologists, medical professionals, and the like.

Another important aspect of the present invention concerns methods of use of the disclosed rAAV vectors, virions, expression systems, compositions, and host cells described herein in the preparation of medicaments for preventing, treating or ameliorating the symptoms of various diseases, dysfunctions, or deficiencies in an animal, such as a vertebrate mammal. Such methods generally involve administration to a mammal, or human in need thereof, one or more of the disclosed vectors, virions, viral particles, host cells, compositions, or pluralities thereof, in an amount and for a time sufficient to prevent, treat, or lessen the symptoms of such a disease, dysfunction, or deficiency in the affected animal. The methods may also encompass prophylactic treatment of animals suspected of having such conditions, or administration of such compositions to those animals at risk for developing such conditions either following diagnosis, or prior to the onset of symptoms.

As described above, the exogenous polynucleotide will preferably encode one or more proteins, polypeptides, peptides, ribozymes, or antisense oligonucleotides, or a combination of these. In fact, the exogenous polynucleotide may encode two or more such molecules, or a plurality of such molecules as may be desired. When combinational gene therapies are desired, two or more different molecules may be produced from a single rAAV expression system, or alternatively, a selected host cell may be transfected with two or more unique rAAV expression systems, each of which will provide unique heterologous polynucleotides encoding at least two different such molecules.

In other embodiment, the invention also concerns the disclosed rAAV vectors comprised within an infectious adeno-associated viral particle, comprised within one or more pharmaceutical vehicles, and may be formulated for administration to a mammal such as a human for therapeutic, and/or prophylactic gene therapy regimens. Such vectors may also be provided in pharmaceutical formulations that are acceptable for veterinary administration to selected livestock, domesticated animals, pets, and the like.

The invention also concerns host cells that comprise the disclosed rAAV vectors and expression systems, particularly mammalian host cells, with human host cells being particularly preferred.

Compositions comprising one or more of the disclosed rAAV vectors, expression systems, infectious AAV particles, host cells also form part of the present invention, and particularly those compositions that further comprise at least a first pharmaceutically-acceptable excipient for use in the manufacture of medicaments and methods involving therapeutic administration of such rAAV vectors. Such pharmaceutical compositions may optionally further comprise liposomes, a lipid, a lipid complex; or the rAAV vectors may be comprised within a microsphere or a nanoparticle. Pharmaceutical formulations suitable for intramuscular, intravenous, or direct injection into an organ or tissue of a human are particularly preferred.

Other aspects of the invention concern recombinant adeno-associated virus virion particles, compositions, and host cells that comprise one or more of the AAV vectors disclosed herein, such as for example pharmaceutical formulations of the vectors intended for administration to a mammal through suitable means, such as, by intramuscular, intravenous, or direct injection to cells, tissues, or organs of a selected mammal. Typically, such compositions may be formulated with pharmaceutically-acceptable excipients as described hereinbelow, and may comprise one or more liposomes, lipids, lipid complexes, microspheres or nanoparticle formulations to facilitate administration to the selected organs, tissues, and cells for which therapy is desired.

Kits comprising one or more of the disclosed vectors, virions, host cells, viral particles or compositions; and (ii) instructions for using the kit in therapeutic, diagnostic, or clinical embodiments also represent preferred aspects of the present disclosure. Such kits may further comprise one or more reagents, restriction enzymes, peptides, therapeutics, pharmaceutical compounds, or means for delivery of the compositions to host cells, or to an animal, such as syringes, injectables, and the like. Such kits may be therapeutic kits for treating or ameliorating the symptoms of particular diseases, and will typically comprise one or more of the modified AAV vector constructs, expression systems, virion particles, or therapeutic compositions described herein, and instructions for using the kit.

Another important aspect of the present invention concerns methods of use of the disclosed vectors, virions, expression systems, compositions, and host cells described herein in the preparation of medicaments for treating or ameliorating the symptoms of various polypeptide deficiencies in a mammal. Such methods generally involve administration to a mammal, or human in need thereof, one or more of the disclosed vectors, virions, host cells, or compositions, in an amount and for a time sufficient to treat or ameliorate the symptoms of such a deficiency in the affected mammal. The methods may also encompass prophylactic treatment of animals suspected of having such conditions, or administration of such compositions to those animals at risk for developing such conditions either following diagnosis, or prior to the onset of symptoms.

BRIEF DESCRIPTION OF THE SEQUENCES

SEQ ID NO:1 is an amino acid sequence of the capsid protein of the wild-type adeno-associated virus serotype 1 (AAV1);

SEQ ID NO:2 is an amino acid sequence of the capsid protein of the wild-type adeno-associated virus serotype 2 (AAV2);

SEQ ID NO:3 is an amino acid sequence of the capsid protein of the wild-type adeno-associated virus serotype 3 (AAV3);

SEQ ID NO:4 is an amino acid sequence of the capsid protein of the wild-type adeno-associated virus serotype 4 (AAV4);

SEQ ID NO:5 is an amino acid sequence of the capsid protein of the wild-type adeno-associated virus serotype 5 (AAV5);

SEQ ID NO:6 is an amino acid sequence of the capsid protein of the wild-type adeno-associated virus serotype 6 (AAV6);

SEQ ID NO:7 is an amino acid sequence of the capsid protein of the wild-type adeno-associated virus serotype 7 (AAV7);

SEQ ID NO:8 is an amino acid sequence of the capsid protein of the wild-type adeno-associated virus serotype 8 (AAV8);

SEQ ID NO:9 is an amino acid sequence of the capsid protein of the wild-type adeno-associated virus serotype 9 (AAV9);

SEQ ID NO:10 is an amino acid sequence of the capsid protein of the wild-type adeno-associated virus serotype 10 (AAV10);

SEQ ID NO:11 is an oligonucleotide primer sequence useful according to the present invention; and SEQ ID NO:12 is an oligonucleotide primer sequence useful according to the present invention.

BRIEF DESCRIPTION OF THE DRAWINGS

FIG. 2A-1, FIG. 2A-2, FIG. 2A-3, FIG. 2B-1, FIG. 2B-2, FIG. 2B-3, FIG. 2C-1, FIG. 2C-2, FIG. 23-3, FIG. 2D-1 FIG. 2D-2, and FIG. 2D-3 show amino acid alignment of the wild-type AAV1-10 capsids. FIG. 2A-1 and FIG. 2A-2 show amino acid alignment of the wild-type AAV1-10 serotype capsids (SEQ ID NO:1 through SEQ ID NO:10). FIG. 2B-1, FIG. 2B-2, and FIG. 2B-3 show conserved, surface-exposed lysine residues in the wild-type AAV1-12 capsids, as well as embodiments of amino acid modifications. The lysine residues conserved among AAV1-12 are shown in bold. FIG. 2C-1 to FIG. 2C-3 show amino acid alignment of the wild-type AAV1-10 serotype capsids, as well as surface-exposed tyrosine residues that are conserved among AAV1-10 capsids (conserved, surface-exposed residues are shown in bold). FIG. 2D-1 to FIG. 2D-3 show amino acid alignment of the wild-type AAV1-10 serotype capsids, as well as surface-exposed serine and threonine residues that are conserved in among AAV1-10 capsids (conserved, surface-exposed residues are shown in bold);

FIG. 3A: Transgene expression was detected by fluorescence microscopy 48 h post infection. FIG. 3B: Images from three visual fields were analyzed as described herein. *$P<0.005$, **$P<0.001$ vs. WT AAV2;

FIG. 4A: EGFP expression analysis at 48 h post-infection at an MOI of $1 \times 10^3$ vgs/cell. FIG. 4B: Quantitation of transduction efficiency of each of the serine-mutant AAV2 vectors. *$P<0.005$, **$P<0.001$ vs. WT AAV2;

FIG. 5 shows packaging and transduction efficiencies of various serine-valine mutant AAV2 vectors relative to wild-type (WT) AAV2 vectors. Briefly, vector packaging and infectivity assays were performed at least twice for each of the mutant-AAV vectors. The packaging efficiency was determined by quantitative PCR analyses. The transduction efficiency was estimated by fluorescence intensity. *No fluorescence was detected at the MOI tested;

FIG. 6A: EGFP expression analysis at 48-hr after infection of 293 cells at an MOT of $1 \times 10^3$ vgs/cell. FIG. 6B: Quantitation of the transduction efficiency of each of the serine-mutant AAV2 vectors. *$P<0.005$, **$P<0.001$ vs. WT AAV2;

FIG. 7 illustrates packaging and transduction efficiencies of exemplary serine-mutant vectors in accordance with one aspect of the present invention which have been replaced with various amino acids relative to wild-type (WT) AAV2 vector. The packaging and infectivity assays were performed as described herein. V=Valine; A=Alanine; D=Aspartic acid; F=Phenylalanine H=Histidine; N=Asparagine; L=Leucine; and I=Isoleucine;

FIG. 8A: Quantitation of the transduction efficiency of WT- and S662V-AAV2 vectors in 293, HeLa, NTH3T3, H2.35 and moDCs. FIG. 8B: Western blot analysis of lysates from different cell lines for p-p38 MAPK expression levels. Total p38 MAPK and GAPDH levels were measured and used as loading controls. *$P<0.005$, **$P<0.001$ vs. WT AAV2;

FIG. 9A shows the effect of JNK and p38 MAPK inhibitors, and site-directed substitution of the serine residue at position 662 on EGFP expression. FIG. 9B provides quantitation of the data in FIG. 9A at 48-hr after infection and initiation of maturation. FIG. 9C shows a representative analysis of expression of co-stimulatory markers such as CD80, CD83, CD86 in moDCs infected with one particular vector in accordance with the present invention—AAV2-S662V—at an MOI $5 \times 10^4$ vgs/cell. iDCs (immature dendritic cells), and mDCs (mature dendritic cells) stimulated with cytokines and generated as described herein were used as negative and positive controls, respectively. A representative example is shown. *$P<0.005$, **$P<0.001$ vs. WT AAV2.

FIG. 11A and FIG. 11B demonstrate that site-directed mutagenesis of surface-exposed serine residues increased transduction efficiency of 293 cells in exemplary scAAV vectors prepared in accordance with one aspect of the present invention;

FIG. 12A and FIG. 12B reveal that site-directed mutagenesis of surface-exposed threonine residues increased transduction efficiency of 293 cells in exemplary scAAV vectors prepared in accordance with one aspect of the present invention;

FIG. 13A and FIG. 13B illustrate that site-directed mutagenesis of exemplary combinations of surface-exposed serine, threonine and/or tyrosine residues also significantly increased the transduction efficiency of H2.35 cells when particularly exemplary scAAV vectors were prepared and used in accordance with the methods described herein;

FIG. 14A shows gene expression profiling of innate immune mediators was performed, and data for fold changes in gene expression at the 2-hr time point comparing AAV vectors with Bay11 (hatched or open bars) with AAV vectors without Bay11 (black or grey bars) are shown. The minimal threshold fold-increase (horizontal black line) was 2.5. FIG. 14B shows a western blot analysis of liver homogenates from mice at 9-hrs following mock-injections, or injections with scAAV vectors, with and without prior administration of Bay11. Samples were analyzed by using anti-p52 antibody for detection of NF-KB signaling in response to AAV exposure. Anti-β-actin antibody was used as a loading control. FIG. 14C shows the humoral response to exemplary AAV vectors in the absence or presence of NF-KB inhibitor. Anti-AAV2 IgG2a levels were determined in peripheral blood from mice at Day 15 following injections with scAAV vectors, with and without prior administration of Bay11 (n=4 each). FIG. 14D shows the transgene expression in murine hepatocytes 10 days' post-injection of $1\times10^{11}$ vgs each of WT-scAAV-EGFP or TM-scAAV-EFGP vectors/animal via the tail-vein. FIG. 14E illustrates the quantitative analyses of representative data from the study depicted in FIG. 141);

FIG. 15A: Equivalent numbers of T47D and T47D+hHGFR cells were infected with various indicated multiplicity-of-infection of scAAV3-CBAp-EGFP vectors under identical conditions. Transgene expression was determined by fluorescence microscopy 72 hrs post-infection. FIG. 15B: T47D+hHGFR cells were transduced with 2,000 vgs/cell of scAAV3 vectors—either in the absence or presence of 5 μg/mL of hHGF. Transgene expression was determined as above. FIG. 15C: The effect of HGFR kinase-specific inhibitor, BMS-777607 (BMS), on AAV3-mediated transgene expression is shown. T47D and T47D+hHGFR cells were mock-treated or pretreated with BMS for 2 hs. Whole-cell lysates were prepared and analyzed on Western blots using various indicated primary antibodies. β-actin was used as a loading control. FIG. 15D: Transduction efficiency of WT and single, double, and triple tyrosine-mutant AAV3 vectors is shown. Huh7 cells were transduced with WT or various indicated Y-F mutant scAAV3-CBAp-EGFP vectors under identical conditions;

FIG. 19A and FIG. 19B shows the transduction efficiency of WT- and lysine-mutant scAAV2 vectors in primary hepatocytes in vivo (C57BL/6 mice; $1\times10^{10}$ scAAV-2-CBAp-EGFP vectors; tail-vein injections; 2-weeks);

FIG. 21A, FIG. 21B, FIG. 21C, FIG. 21D, FIG. 21E, FIG. 21F, FIG. 21G, FIG. 21H, and FIG. 21I show the transduction efficiency of WT- and exemplary lysine-mutated capsid-containing scAAV2 vectors in HeLa cells in vitro (2,000 vgs/cell; 48 hrs) in accordance with one aspect of the present invention;

FIG. 22A, FIG. 22B, FIG. 22C, FIG. 22D, FIG. 22E, FIG. 22F, FIG. 22G, FIG. 22H, and FIG. 22I show that site-directed mutagenesis of a combination of surface-exposed serine, threonine and/or tyrosine residues increase transduction efficiency of monocyte-derived dendritic cells by scAAV vectors in accordance with one aspect of the present invention;

DESCRIPTION OF ILLUSTRATIVE EMBODIMENTS

Figure 1:
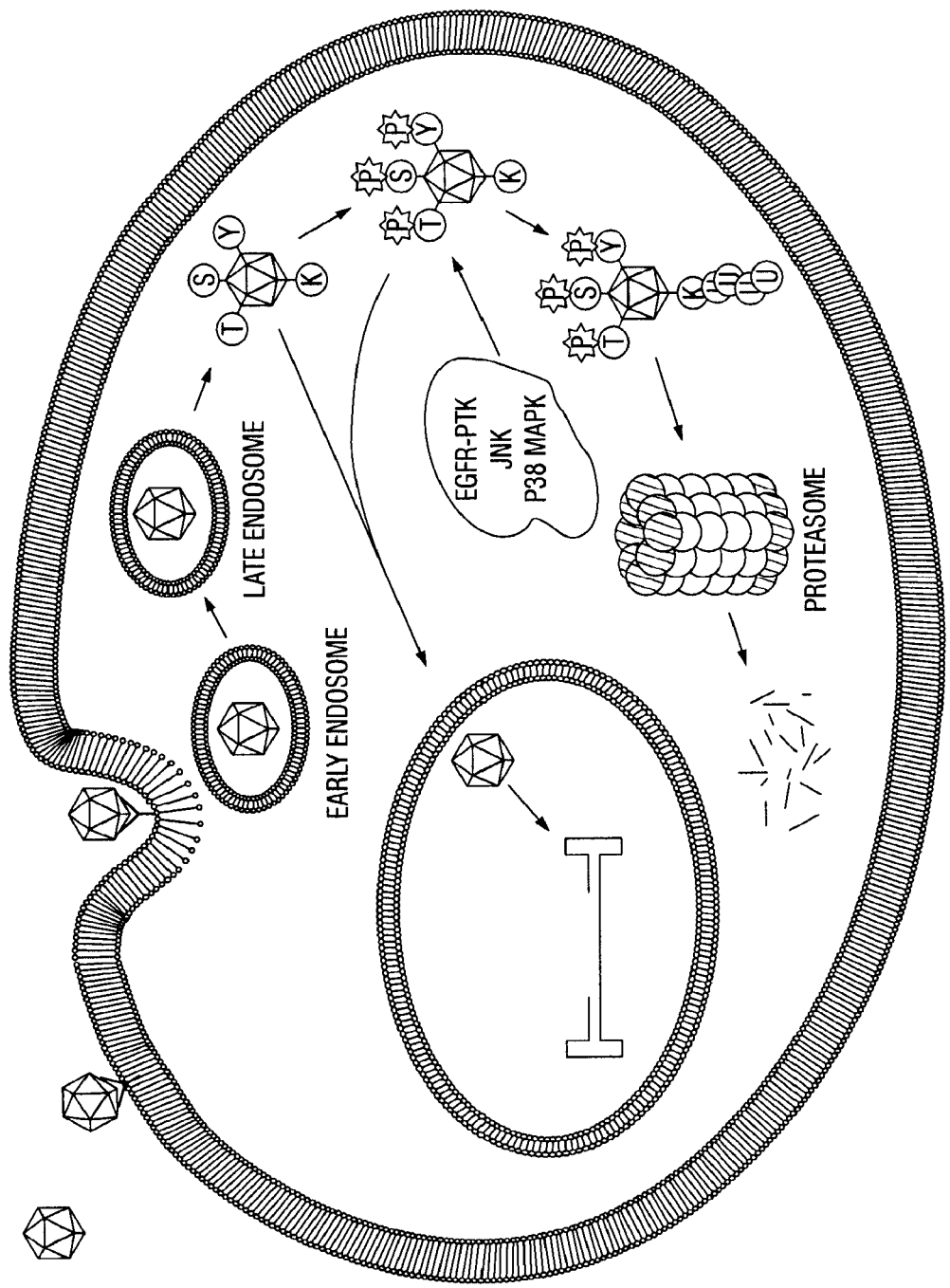
FIG. 1 shows an exemplary schematic model for AAV2 trafficking inside a mammalian host cell.

The present invention provides AAV capsid proteins comprising modification of one or a combination of the surface-exposed lysine, serine, threonine and/or tyrosine residues in the VP3 region. Also provided are rAAV virions that include one or more of the AAV capsid protein mutations disclosed herein, as well as nucleic acid molecules and rAAV vectors encoding the AAV capsid proteins of the present invention. Advantageously, the rAAV vectors and virions of the present invention have improved efficiency in transduction of a variety of cells, tissues and organs of interest and/or reduces host immune responses to the vectors, when compared to wild-type rAAV vectors and virions.

In one embodiment, the present invention provides a nucleic acid molecule comprising a nucleotide sequence encoding an AAV capsid protein, wherein the VP3 region of the AAV capsid protein comprises a non-lysine residue at one or more positions that correspond to one or more lysine residues in the VP3 region of the capsid protein of the wild-type AAV [e.g., SEQ ID NO:1, SEQ ID NO:2, SEQ ID NO:3, SEQ ID NO:4, SEQ ID NO:5, SEQ ID NO:6, SEQ TD NO:7, SEQ ID NO:8, SEQ ID NO:9, or SEQ ID NO:10; and in one particularly exemplary embodiment, the capsid protein of wild-type AAV2 (SEQ ID NO:2)], wherein one or more of the lysine residue(s) in the VP3 region of the wild-type AAV is selected from the one or more lysine residues as illustrated in FIG. 2A and FIG. 2B.

In a specific embodiment, one or more surface-exposed lysine residue corresponding to one or more lysine residues selected from the group consisting of K258, K321, K459, K490, K507, K527, K572, K532, K544, K549, K556, K649, K655, K665, and K706 of the wild-type AAV capsid protein [e.g., SEQ ID NOs:1-10; in one embodiment, the capsid protein of wild-type AAV2 (SEQ ID NO:2)] are modified.

In one embodiment, the surface-exposed lysine residue corresponding to K532 of the wild-type AAV2 capsid sequence is modified. In one embodiment, the surface-exposed lysine residue of the AAV capsid is modified into glutamic acid (E) or arginine (R). In one specific embodiment, the surface-exposed lysine residue corresponding to K532 of the wild-type AAV2 capsid sequence is modified into arginine (K532R).

In certain embodiments, one or more surface-exposed lysine residues corresponding to K490, K544, K549, and K556 of the wild-type AAV2 capsid sequence are modified. In certain specific embodiments, one or more surface-exposed lysine residue corresponding K490, K544, K549, and K556 of the wild-type AAV2 capsid sequence are modified into glutamic acid (E).

In one embodiment, the present invention provides AAV2 vectors wherein surface-exposed lysine residues corresponding to K544 and K556 residues of the wild-type AAV2 capsid are modified into glutamic acid (E).

In certain embodiments, one or more surface-exposed lysine residues corresponding to K530, K547, and K569 of the wild-type AAV8 capsid sequence are modified. In certain specific embodiments, one or more surface-exposed lysine residue corresponding K530, K547, and K569 of the wild-type AAV2 capsid sequence are modified into glutamic acid (E) or arginine (R).

In addition, the present invention provides a method for transduction of cells, tissues, and/or organs of interest, comprising introducing into a cell, a composition comprising an effective amount of a rAAV vector and/or virion of the present invention.

Phosphorylation of surface-exposed lysine, serine, threonine and/or tyrosine residues on the AAV capsids can result in the ubiquitination/proteasomal degradation of the vectors. Serine/threonine protein kinases are involved in a wide variety of cellular processes including cell differentiation, transcription regulation, and development. Phosphorylation of the surface-exposed serine and/or threonine residues on the viral capsid induces proteasome-mediated degradation of the vectors and reduces vector transduction efficiency. Cellular epidermal growth factor receptor protein tyrosine kinase (EGFR-PTK) also phosphorylates capsids at surface tyrosine residues, and, thus negatively impacts nuclear transport and subsequent transgene expression by recombinant AAV2 vectors.

Surface-exposed lysine, serine, threonine and/or tyrosine residues on the AAV capsids are identified (FIG. 2A, FIG. 2B, FIG. 2C, and FIG. 21)). For instance, the VP3 region of the capsid protein of the wild-type AAV2 contains various surface-exposed lysine (K) residues (K258, K321, K459, K490, K507, K527, K572, K532, K544, K549, K556, K649, K655, K665, K706), surface-exposed serine (S) residues (S261, S264, S267, S276, S384, S458, S468, S492, S498, S578, S658, S662, S668, S707, S721), surface-exposed threonine (T) residues (T251, T329, T330, T454, 1455, T503, T550, T592, T581, T597, T491, T671, T659, T660, T701, T713, T716), and surface-exposed tyrosine residues (Y252, Y272, Y444, Y500, Y700, Y704, Y730). As shown in FIG. 2A, FIG. 2B, FIG. 2C, and FIG. 2D, these surface-exposed lysine, serine, threonine and/or tyrosine residues of the capsids are highly conserved among AAV1-12.

Site-directed mutagenesis of the surface-exposed lysine, serine, threonine, and/or tyrosine residues was performed and the results show that modification or substitution of one or a combination of the surface-exposed residues can enable the AAV vector to bypass the ubiquitination and proteasome-mediated degradation steps, thereby yielding novel AAV vectors with high-efficiency transduction. Substitution of surface exposed tyrosine residues on AAV capsids permits the vectors to escape ubiquitination, and thus, inhibits proteasome-mediated degradation. Although phosphorylated AAV vectors could enter cells as efficiently as their unphosphorylated counterparts, their transduction efficiency was significantly reduced. This reduction was not due to impaired viral second-strand DNA synthesis since transduction efficiency of both single-stranded AAV (ssAAV) and self-complementary AAV (rAAV) vectors was decreased.

Recombinant AAV vectors containing point mutations in surface exposed tyrosine residues confer higher transduction efficiency at lower doses, when compared to the wild-type (WT) AAV vectors.

In addition, in accordance of the present invention, (i) site-directed mutagenesis of the 15 surface-exposed serine (S) residues on the AAV2 capsid with valine (V) residues leads to improved transduction efficiency of S458V, S492V, and S662V mutant vectors compared with the WT AAV2 vector; (ii) the S662V mutant vector efficiently transduces primary human monocyte-derived dendritic cells (moDCs), a cell type not readily amenable to transduction by the conventional AAV vectors; (iii) high-efficiency transduction of moDCs by S662V mutant does not induce any phenotypic changes in these cells; and (iv) recombinant S662V-rAAV vectors carrying a truncated human telomerase (hTERT) gene transduced DCs result in rapid, specific T-cell clone proliferation and generation of robust CTLs, which lead to specific cell lysis of K562 cells. The results demonstrate that the serine-modified rAAV2 vectors of the present invention result in high-efficiency transduction of moDCs.

In the setting of tumor immunotherapy, the time of T-cell activation and the potency and longevity of CD8 T cell responses are crucial factors in determining the therapeutic outcome. In accordance with the present invention, increased transduction efficiency of moDC by the serine-mutant AAV2 vectors resulted in superior priming of T-cells. Human telomerase was used as a specific target since clinical studies have shown that human telomerase is an attractive candidate for a broadly expressed rejection antigen for many cancer patients. In addition, transduction efficiency of the S662V mutant vector was further augmented by pre-treatment of cells with specific inhibitors of JNK and p38 MAPK, indicating that one or more surface-exposed threonine (T) residues on AAV2 capsids are most likely phosphorylated by these kinases.

Recombinant AAV Vectors and Virions

One aspect of the invention provides AAV capsid proteins comprising modification of one or a combination of the surface-exposed lysine, serine, threonine and/or tyrosine residues in the VP3 region. Also provided are rAAV virions comprising the AAV capsid proteins of the present invention, as well as nucleic acid molecules and rAAV vectors encoding the AAV capsid proteins of the present invention. Advantageously, the rAAV vectors and virions of the present invention have improved efficiency in transduction of a variety of cells, tissues and organs of interest, when compared to wild-type rAAV vectors and virions.

In one embodiment, the present invention provides a nucleic acid molecule comprising a nucleotide sequence encoding an AAV capsid protein, wherein the AAV capsid protein comprises modification of one or a combination of the surface-exposed lysine, serine, threonine and/or tyrosine residues in the VP3 region. Advantageously, modification of the surface-exposed lysine, serine, threonine and/or tyrosine residues prevents or reduces the level of ubiquitination of the AAV vectors, and, thereby, prevents or reduces the level of proteasome-mediated degradation. In addition, modification of the surface-exposed lysine, serine, threonine and/or tyrosine residues in accordance with the present invention improves transduction efficiency.

In one embodiment, the nucleic acid molecule comprising a nucleotide sequence encoding an AAV capsid protein, wherein the VP3 region of the AAV capsid protein comprises one or a combination of the following characteristics:

(a)
- (i) a non-lysine residue at one or more positions that correspond to a lysine residue in the VP3 region of the capsid protein of the wild-type AAV (e.g., SEQ ID NOs:1-10; in one embodiment, the capsid protein of wild-type AAV2 (SEQ ID NO:2)), wherein said lysine residue in the VP3 region of the wild-type AAV is selected from the group consisting of K258, K321, K459, K490, K507, K527, K572, K532, K544, K549, K556, K649, K655, K665, and K706, wherein said non-lysine residue does not result in phosphorylation and/or ubiquitination of an AAV vector; and/or
- (ii) a chemically-modified lysine residue at one or more positions that correspond to a lysine residue in the VP3 region of the capsid protein of the wild-type AAV (e.g., SEQ ID NOs:1-10; in one embodiment, the capsid protein of wild-type AAV2 (SEQ ID NO:2)), wherein said lysine residue in the VP3 region of the wild-type AAV is selected from the group consisting of K258, K321, K459, K490, K507, K527, K572, K532, K544, K549, K556, K665, K649, K655, and K706, wherein said chemically-modified lysine residue docs not result in phosphorylation and/or ubiquitination of an AAV vector,
- (iii) a non-lysine residue at one or more positions that correspond to a lysine residue in the VP3 region of the capsid protein of the wild-type AAV (e.g., SEQ ID NOs:1-10; in one embodiment, the capsid protein of wild-type AAV8 (SEQ ID NO:8)), wherein said lysine residue in the VP3 region of the wild-type AAV is selected from the group consisting of K530, K547, and K569, wherein said non-lysine residue does not result in phosphorylation and/or ubiquitination of an AAV vector; and/or
- (iv) a chemically-modified lysine residue at one or more positions that correspond to a lysine residue in the VP3 region of the capsid protein of the wild-type AAV (e.g., SEQ ID NOs:1-10; in one embodiment, the capsid protein of wild-type AAV8 (SEQ ID NO:8)), wherein said lysine residue in the VP3 region of the wild-type AAV is selected from the group consisting of K530, K547, and K569, wherein said chemically-modified lysine residue does not result in phosphorylation and/or ubiquitination of an AAV vector;

(b)
- (i) a non-serine residue at one or more positions that correspond to a serine residue in the VP3 region of the capsid protein of the wild-type AAV (e.g., SEQ 1D NOs:1-10; in one embodiment, the capsid protein of wild-type AAV2 (SEQ ID NO:2)), wherein said serine residue in the VP3 region of the wild-type AAV is selected from the group consisting of S261, S264, S267, S276, S384, S458, S468, S492, S498, 5578, S658, S662, S668, S707, and S721, wherein said non-serine residue does not result in phosphorylation and/or ubiquitination of an AAV vector; and/or
- (ii) a chemically-modified serine residue at one or more positions that correspond to a serine residue in the VP3 region of the capsid protein of the wild-type AAV (e.g., SEQ ID NOs:1-10; in one embodiment, the capsid protein of wild-type AAV2 (SEQ ID NO:2)), wherein said serine residue in the VP3 region of the wild-type AAV is selected from the group consisting of S261, S264, S267, S276, S384, S458, S468, S492, S498, S578, S658, S662, S668, S707, and S721, wherein said chemically-modified serine residue does not result in phosphorylation and/or ubiquitination of an AAV vector;

(c)
- (i) a non-threonine residue at one or more positions that correspond to a threonine residue in the VP3 region of the capsid protein of the wild-type AAV (e.g., SEQ ID NOs:1-10; in one embodiment, the capsid protein of wild-type AAV2 (SEQ ID NO:2)), wherein said threonine residue in the VP3 region of the wild-type AAV is selected from the group consisting of T251, T329, T330, T454, T455, T503, T550, T592, T581, T597, T491, T671, T659, T660, T701, T713, and T716, wherein said non-threonine residue does not result in phosphorylation and/or ubiquitination of an AAV vector; and/or
- (ii) a chemically-modified threonine residue at one or more positions that correspond to a threonine residue in the VP3 region of the capsid protein of the wild-type AAV (e.g., SEQ ID NOs:1-10; in one embodiment, the capsid protein of wild-type AAV2 (SEQ ID NO:2)), wherein said threonine residue in the VP3 region of the wild-type AAV is selected from the group consisting of T251, T329, T330, T454, T455, T503, T550, T592, T581, T597, T491, T671, T659, T660, T701, T713, and T716, wherein said chemically-modified threonine residue does not result in phosphorylation and/or ubiquitination of an AAV vector; and/or (d)
- (i) a non-tyrosine residue at one or more positions that correspond to a tyrosine residue in the VP3 region of the capsid protein of the wild-type AAV (e.g., SEQ ID NOs:1-10; in one embodiment, the capsid protein of wild-type AAV2 (SEQ ID NO:2)), wherein said tyrosine residue in the VP3 region of the wild-type AAV is selected from the group consisting of Y252, Y272, Y444, Y500, Y700, Y704, and Y730, wherein said non-tyrosine residue does not result in phosphorylation and/or ubiquitination of an AAV vector, and/or
- (ii) a chemically-modified tyrosine residue at one or more positions that correspond to a tyrosine residue in the VP3 region of the capsid protein of the wild-type AAV (e.g., SEQ ID NOs:1-10; in one embodiment, the capsid protein of wild-type AAV2 (SEQ ID NO:2)), wherein said tyrosine residue in the VP3 region of the wild-type AAV is selected from the group consisting of Y252, Y272, Y444, Y500, Y700, Y704, and Y730, wherein said chemically-modified tyrosine residue does not result in phosphorylation and/or ubiquitination of an AAV vector.

In another embodiment, the present invention provides a nucleic acid molecule comprising a nucleotide sequence encoding an AAV capsid protein, wherein one or more of surface-exposed lysine, serine, threonine and/or tyrosine residues in the VP3 region are modified as follows:

(a)
- (i) at least one lysine residue in the VP3 region is chemically modified or is modified into a non-lysine residue, wherein the modified residue corresponds to K258, K321, K459, K490, K507, K527, K572, K532, K544, K549, K556, K649, K655, or K706 of the wild-type AAV capsid sequence (e.g., SEQ ID NOs:1-10; in one embodiment, the capsid protein of wild-type AAV2 (SEQ ID NO:2)), wherein said non-lysine residue or said chemically-modified lysine residue does not result in phosphorylation and/or ubiquitination of an AAV vector; and/or (ii)
at least one lysine residue in the VP3 region is chemically modified or is modified into a non-lysine residue, wherein the modified residue corresponds to K530, K547, or K569 of the wild-type AAV capsid sequence (e.g., SEQ ID NOs:1-10; in one embodiment, the capsid protein of wild-type AAV8 (SEQ ID NO:8)), wherein said non-lysine residue or said chemically-modified lysine residue does not result in phosphorylation and/or ubiquitination of an AAV vector, (b) at least one serine residue in the VP3 region is chemically modified or is modified into a non-serine residue, wherein the modified residue corresponds to S261, S264, S267, S276, S384, S458, S468, S492, S498, S578, S658, S662, S668, S707, or S721 of the wild-type AAV capsid sequence (e.g., SEQ ID NOs:1-10; in one embodiment, the capsid protein of wild-type AAV2 (SEQ ID NO:2)), wherein said non-serine residue or said chemically-modified serine residue does not result in phosphorylation and/or ubiquitination of an AAV vector;

(c) at least one threonine residue in the VP3 region is chemically modified or is modified into a non-threonine residue, wherein the modified residue corresponds to T251, T329, T330, T454, T455, T503, T550, T592, T581, T597, T491, T671, T659, T660, T701, T713, or T716 of the wild-type AAV capsid sequence (e.g., SEQ ID NOs:1-10; in one embodiment, the capsid protein of wild-type AAV2 (SEQ ID NO:2)), wherein said non-threonine residue or said chemically-modified threonine residue does not result in phosphorylation and/or ubiquitination of an AAV vector, and (d) at least one tyrosine residue in the VP3 region is chemically modified or is modified into a non-tyrosine residue, wherein the modified residue corresponds to Y252, Y272, Y444, Y500, Y700, Y704, or Y730 the wild-type AAV capsid sequence (e.g., SEQ ID NOs:1-10; in one embodiment, the capsid protein of wild-type AAV2 (SEQ ID NO:2)), wherein said non-tyrosine residue or said chemically-modified tyrosine residue does not result in phosphorylation and/or ubiquitination of an AAV vector.

The present invention also provides AAV VP3 capsid proteins having modification of one or more surface-exposed lysine, serine, threonine and/or tyrosine residues. In one embodiment, the present invention provides an AAV VP3 capsid protein comprising one or a combination of the following characteristics:

(a)
(i) a non-lysine residue at one or more positions that correspond to a lysine residue in the VP3 region of the capsid protein of the wild-type AAV (e.g., SEQ ID NOs:1-10; in one embodiment, the capsid protein of wild-type AAV2 (SEQ ID NO:2)), wherein said lysine residue in the VP3 region of the wild-type AAV is selected from the group consisting of K258, K321, K459, K490, K507, K527, K572, K532, K544, K549, K556, K649, K655, K665, and K706, wherein said non-lysine residue does not result in phosphorylation and/or ubiquitination of an AAV vector; and/or (ii) a chemically-modified lysine residue at one or more positions that correspond to a lysine residue in the VP3 region of the capsid protein of the wild-type AAV (e.g., SEQ ID NOs:1-10; in one embodiment, the capsid protein of wild-type AAV2 (SEQ ID NO:2)), wherein said lysine residue in the VP3 region of the wild-type AAV is selected from the group consisting of K258, K321, K459, K490, K507, K527, K572, K532, K544, K549, K556, K649, K655, K665, and K706, wherein said chemically-modified lysine residue does not result in phosphorylation and/or ubiquitination of an AAV vector;

(iii) a non-lysine residue at one or more positions that correspond to a lysine residue in the VP3 region of the capsid protein of the wild-type AAV (e.g., SEQ ID NOs:1-10; in one embodiment, the capsid protein of wild-type AAV8 (SEQ ID NO:8)), wherein said lysine residue in the VP3 region of the wild-type AAV is selected from the group consisting of K530, K547, and K569, wherein said non-lysine residue does not result in phosphorylation and/or ubiquitination of an AAV vector; and/or (iv) a chemically-modified lysine residue at one or more positions that correspond to a lysine residue in the VP3 region of the capsid protein of the wild-type AAV (e.g., SEQ ID NOs:1-10; in one embodiment, the capsid protein of wild-type AAV8 (SEQ ID NO:8)), wherein said lysine residue in the VP3 region of the wild-type AAV is selected from the group consisting of K530, K547, and K569, wherein said chemically-modified lysine residue does not result in phosphorylation and/or ubiquitination of an AAV vector;

(b)
(i) a non-serine residue at one or more positions that correspond to a serine residue in the VP3 region of the capsid protein of the wild-type AAV (e.g., SEQ ID NOs:1-10; in one embodiment, the capsid protein of wild-type AAV2 (SEQ ID NO:2)), wherein said serine residue in the VP3 region of the wild-type AAV is selected from the group consisting of S261, S264, S267, S276, S384, S458, S468, S492, S498, S578, S658, S662, S668, S707, and S721, wherein said non-serine residue does not result in phosphorylation and/or ubiquitination of an AAV vector; and/or (ii) a chemically-modified serine residue at one or more positions that correspond to a serine residue in the VP3 region of the capsid protein of the wild-type AAV (e.g., SEQ ID NOs:1-10; in one embodiment, the capsid protein of wild-type AAV2 (SEQ ID NO:2)), wherein said serine residue in the VP3 region of the wild-type AAV is selected from the group consisting of S261, S264, S267, S276, S384, S458, S468, S492, S498, S578, S658, S662, S668, S707, and S721, wherein said chemically-modified serine residue does not result in phosphorylation and/or ubiquitination of an AAV vector;

(c)
(i) a non-threonine residue at one or more positions that correspond to a threonine residue in the VP3 region of the capsid protein of the wild-type AAV (e.g., SEQ ID NOs:1-10; in one embodiment, the capsid protein of wild-type AAV2 (SEQ ID NO:2)), wherein said threonine residue in the VP3 region of the wild-type AAV is selected from the group consisting of T251, T329, T330, T454, T455, T503, T550, T592, T581, T597, T491, T671, T659, T660, T701, T713, and T716, wherein said non-threonine residue does not result in phosphorylation and/or ubiquitination of an AAV vector; and/or (ii) a chemically-modified threonine residue at one or more positions that correspond to a threonine residue in the VP3 region of the capsid protein of the wild-type AAV (e.g., SEQ ID NOs:1-10; in one embodiment, the capsid protein of wild-type AAV2 (SEQ ID NO:2)), wherein said threonine residue in the VP3 region of the wild-type AAV is selected from the group consisting of T251, T329, T330, T454, T455, T503, T550, T592, T581, T597, T491, T671, T659, T660, T701, T713, and T716, wherein said chemically-modified threonine residue does not result in phosphorylation and/or ubiquitination of an AAV vector; and/or (d)

(i) a non-tyrosine residue at one or more positions that correspond to a tyrosine residue in the VP3 region of the capsid protein of the wild-type AAV (e.g., SEQ ID NOs:1-10; in one embodiment, the capsid protein of wild-type AAV2 (SEQ ID NO:2)), wherein said tyrosine residue in the VP3 region of the wild-type AAV is selected from the group consisting of Y252, Y272, Y444, Y500, Y700, Y704, and Y730, wherein said non-tyrosine residue does not result in phosphorylation and/or ubiquitination of an AAV vector; and/or (ii) a chemically-modified tyrosine residue at one or more positions that correspond to a tyrosine residue in the VP3 region of the capsid protein of the wild-type AAV (e.g., SEQ ID NOs:1-10; in one embodiment, capsid protein of wild-type AAV2 (SEQ ID NO:2)), wherein said tyrosine residue in the VP3 region of the wild-type AAV is selected from the group consisting of Y252, Y272, Y444, Y500, Y700, Y704, and Y730, wherein said chemically-modified tyrosine residue does not result in phosphorylation and/or ubiquitination of an AAV vector.

In another embodiment, the present invention provides an AAV capsid protein, wherein one or more of surface-exposed lysine, serine, threonine and/or tyrosine residues in the VP3 region are modified as follows:

(a)

(i) at least one lysine residue in the VP3 region is chemically modified or is modified into a non-lysine residue, wherein the modified residue corresponds to K258, K321, K459, K490, K507, K527, K572, K532, K544, K549, K556, K649, K655, K665, or K706 of the wild-type AAV capsid sequence (e.g., SEQ ID NOs:1-10; in one embodiment, the capsid protein of wild-type AAV2 (SEQ ID NO:2)), wherein said non-lysine residue or said chemically-modified lysine residue does not result in phosphorylation and/or ubiquitination of an AAV vector; and/or (ii) at least one lysine residue in the VP3 region is chemically modified or is modified into a non-lysine residue, wherein the modified residue correspond to K530, K547, or K569 of the wild-type AAV capsid sequence (e.g., SEQ ID NOs:1-10; in one embodiment, the capsid protein of wild-type AAV8 (SEQ ID NO:8)), wherein said non-lysine residue or said chemically-modified lysine residue does not result in phosphorylation and/or ubiquitination of an AAV vector, (b) at least one serine residue in the VP3 region is chemically modified or is modified into a non-serine residue, wherein the modified residue correspond to S261, S264, S267, S276, S384, S458, S468, S492, S498, S578, S658, S662, S668, S707, or S721 of the wild-type AAV capsid sequence (e.g., SEQ ID NOs:1-10; in one embodiment, the capsid protein of wild-type AAV2 (SEQ ID NO:2)), wherein said non-serine residue or said chemically-modified serine residue does not result in phosphorylation and/or ubiquitination of an AAV vector;

(c) at least one threonine residue in the VP3 region is chemically modified or is modified into a non-threonine residue, wherein the modified residue correspond to T251, T329, T330, T454, T455, T503, T550, T592, T581, T597, T491, T671, T659, T660, T701, T713, or T716 of the wild-type AAV capsid sequence (e.g., SEQ ID NOs:1-10; in one embodiment, the capsid protein of wild-type AAV2 (SEQ ID NO:2)), wherein said non-threonine residue or said chemically-modified threonine residue does not result in phosphorylation and/or ubiquitination of an AAV vector; and (d) at least one tyrosine residue in the VP3 region is chemically modified or is modified into a non-tyrosine residue, wherein the modified residue correspond to Y252, Y272, Y444, Y500, Y700, Y704, or Y730 the wild-type AAV capsid sequence (e.g., SEQ ID NOs:1-10; in one embodiment, the capsid protein of wild-type AAV2 (SEQ ID NO:2)), wherein said non-tyrosine residue or said chemically-modified tyrosine residue does not result in phosphorylation and/or ubiquitination of an AAV vector. As shown in FIG. 2A, FIG. 2B. FIG. 2C, and FIG. 2D, surface-exposed lysine, serine, threonine and/or tyrosine residues located in the VP3 region of the capsid protein are highly conserved among various AAV serotypes (AAV1 to 12). In one embodiment, the nucleic acid molecule comprising a nucleotide sequence encoding an AAV capsid protein, wherein the AAV serotype is selected from AAV1 to 12. In certain embodiments, the wild-type AAV capsid protein has an amino acid sequence selected from SEQ ID NOs: 1-10.

In one specific embodiment, the nucleic acid molecule comprises a nucleotide sequence encoding an AAV2 capsid protein. The adeno-associated virus 2 (AAV2) is a non-pathogenic human parvovirus. Recombinant AAV2 vectors have been shown to transduce a wide variety of cells and tissues in vitro and in vivo, and are currently in use in Phase I/II clinical trials for gene therapy of a number of diseases such as cystic fibrosis, alpha-1 antitrypsin deficiency, Parkinson's disease, Batten's disease, and muscular dystrophy.

In one embodiment, the present invention provides an AAV capsid protein, wherein the AAV capsid protein comprises the amino acid sequence of the capsid protein of the wild-type AAV2 (SEQ ID NO:2) except that one or more of the amino acid residues of the wild-type AAV2 capsid are modified as follows:

(a) at least one lysine residue of the wild-type AAV2 capsid sequence selected from the group consisting of K258, K321, K459, K490, K507, K527, K572, K532, K544, K549, K556, K649, K655, K665, and K706 is modified into a non-lysine residue, or said lysine residue is chemically modified so that said non-lysine residue or said chemically-modified lysine residue does not result in phosphorylation and/or ubiquitination of an AAV vector;

(b) at least one serine residue of the wild-type AAV2 capsid sequence selected from the group consisting of S261, S264, 5267, 5276, 5384, S458, S468, S492, S498, 5578, S658, 5662, 5668, 5707, and S721 is modified into a non-serine residue, or said serine residue is chemically modified so that said non-serine residue or said chemically-modified serine residue does not result in phosphorylation and/or ubiquitination of an AAV vector;

(c) at least one threonine residue of the wild-type AAV2 capsid sequence selected from the group consisting of T251, T329, T330, T454, T455, T503, T550, T592, T581, T597, T491, T671, T659, T660, T701, T713, and 1716 is modified into a non-threonine residue, or said threonine residue is chemically modified so that said non-threonine residue or said chemically-modified threonine residue does not result in phosphorylation and/or ubiquitination of an AAV vector; and/or (d) at least one tyrosine residue of the wild-type AAV2 capsid sequence selected from the group consisting of Y252, Y272, Y444, Y500, Y700, Y704, and Y730 is modified into a non-threonine residue is modified into a non-tyrosine residue, or said tyrosine residue is chemically modified so that said non-tyrosine residue or said chemically-modified tyrosine residue docs not result in phosphorylation and/or ubiquitination of an AAV vector. In one embodiment, a surface-exposed lysine residue corresponding to a lysine residue selected from K532, K459, K490, K544, K549, K556, K527, K490, K143, or K137 of the wild-type AAV capsid sequence (e.g., SEQ ID NOs:1-10; in one embodiment, the capsid protein of wild-type AAV2 (SEQ ID NO:2)) is modified into a non-lysine residue and/or is chemically modified so that said non-lysine residue or said modified lysine residue does not result in phosphorylation and/or ubiquitination of an AAV vector.

In another embodiment, the present invention provides an AAV capsid protein, wherein the AAV capsid protein comprises the amino acid sequence of the capsid protein of the wild-type AAV8 (SEQ ID NO:8) except that one or more surface-exposed lysine residues corresponding to K530, K547, and K569 of the wild-type AAV8 capsid are modified into a non-lysine residue (such as, glutamic acid (E), arginine (R)) and/or are modified chemically modified, wherein said non-lysine residue or said modified lysine residue does not result in phosphorylation and/or ubiquitination of an AAV vector. In certain embodiments, the surface-exposed lysine residues of AAV sequence are modified into glutamic acid (E), arginine (R), serine (S), or isoleucine (I) to avoid in phosphorylation and/or ubiquitination of the AAV vector.

The present invention also provides a nucleic acid molecule comprises a nucleotide sequence encoding an AAV capsid protein (e.g., VP3) of the present invention.

In one specific embodiment, the surface-exposed lysine residue corresponding to K532 of the wild-type AAV2 capsid sequence is modified. In one embodiment, the surface-exposed lysine residue of the AAV capsid is modified into glutamic acid (E) or arginine (R). In one specific embodiment, the surface-exposed lysine residue corresponding to K532 of the wild-type AAV2 capsid sequence is modified into arginine (K532R).

In one embodiment, at least one surface-exposed lysine residue of an AAV capsid corresponding to a lysine position of a wild-type AAV2 capsid sequence is modified as indicated in FIG. 2B.

In one embodiment, at least one surface-exposed serine residue corresponding to a serine residue selected from S662, S261, 5468, S458, S276, 5658, S384, or S492 of the wild-type AAV capsid sequence (e.g., SEQ ID NOs:1-10; in one embodiment, the capsid protein of wild-type AAV2 (SEQ ID NO:2)) is modified into a non-serine residue and/or is chemically modified so that said non-serine residue or said modified serine residue does not result in phosphorylation and/or ubiquitination of an AAV vector.

In one specific embodiment, the surface-exposed serine residue corresponding S662 of the wild-type AAV2 capsid sequence is modified. In one embodiment, the surface-exposed serine residue of the AAV capsid is modified into valine (V), aspartic acid (D), or histidine (H). In one specific embodiment, the surface-exposed serine residue corresponding to 5662 of the wild-type AAV2 capsid sequence is modified into valine (S662V).

In one embodiment, a surface-exposed threonine residue corresponding to a threonine residue selected from T455, T491, T550, T659, or T671 of the wild-type AAV capsid sequence [e.g., SEQ ID NOs:1-10; and in a particular embodiment, the capsid protein of wild-type AAV2 (SEQ ID NO:2)] is modified into a non-threonine residue and/or is chemically modified so that said non-threonine residue or said modified threonine residue does not result in phosphorylation and/or ubiquitination of an AAV vector.

In one specific embodiment, the surface-exposed threonine residue corresponding to T491 of the wild-type AAV2 capsid sequence is modified. In one embodiment, the surface-exposed threonine residue of the AAV capsid is modified into valine (V). In one specific embodiment, the surface-exposed threonine residue corresponding to T491 of the wild-type AAV2 capsid sequence is modified into valine (T491V).

In one embodiment, the AAV vector comprises a modification of surface-exposed threonine residues at positions corresponding to (T550V+T659V+T491V) of the wild-type AAV capsid sequence [e.g., SEQ ID NOs:1-10; and in a particular embodiment, the capsid protein of wild-type AAV2 (SEQ ID NO:2)]. In one embodiment, a surface-exposed tyrosine residue corresponding to a tyrosine residue selected from Y252, Y272, Y444, Y500, Y704, Y720, Y730, or Y673 of the wild-type AAV capsid sequence (e.g., SEQ ID NOs:1-10; in one embodiment, the capsid protein of wild-type AAV2 (SEQ ID NO:2)) is modified into a non-tyrosine residue and/or is chemically modified so that said non-tyrosine residue or said modified tyrosine residue does not result in phosphorylation and/or ubiquitination of an AAV vector.

In one embodiment, the surface-exposed tyrosine residue of the AAV capsid is modified into phenylalanine (F). In one embodiment, the AAV vector comprises a modification of surface-exposed tyrosine residues at positions corresponding to (Y730F+Y500F+Y444F) of the wild-type AAV capsid sequence [e.g., SEQ ID NO:1 through SEQ ID NO:10; and in a particular embodiment, the capsid protein of wild-type AAV2 (SEQ ID NO:2)].

In one embodiment, a combination of surface-exposed lysine, serine, threonine and/or tyrosine residues of the AAV capsid is modified, wherein the modification occurs at positions corresponding to (Y444F+Y500F+Y730F+T491V), (Y444F+Y500F+Y730F+T491V+T550V), (Y444F+Y500F+Y730F+T491V+T659V), (T491V+T550V+T659V), (Y440F+Y500F+Y730F), (Y444F+Y500F+Y730F+T491V+S662V), and/or (Y444F+Y500F+Y730F+T491V+T550V+T659V) of the wild-type AAV capsid sequence [e.g., SEQ ID NO:1 through SEQ ID NO:10; in one embodiment, the capsid protein of wild-type AAV2 (SEQ m NO:2)]. Also provided are AAV capsid proteins encoded by the nucleic acid molecules of the present invention.

In one embodiment, the present invention provides a recombinant adeno-associated viral (rAAV) vector comprising a nucleic acid sequence that encodes an AAV capsid protein of the invention. In another embodiment, the present invention provides a rAAV virion comprising an AAV capsid protein of the invention. In one embodiment, the rAAV vector and virion has enhanced transduction efficiency, when compared to the wild-type rAAV vector and virion. In another embodiment, the rAAV vector and virion is capable of efficient transduction of cells, tissues, and/or organs of interest.

In one embodiment, the rAAV vector further comprises a transgene (also referred to as a heterologous nucleic acid molecule) operably linked to a promoter and optionally, other regulatory elements. In one embodiment, the transgene encodes a therapeutic agent of interest.

Exemplary promoters include one or more heterologous, tissue-specific, constitutive or inducible promoters, including, but not limited to, a promoter selected from the group consisting of cytomegalovirus (CMV) promoters, desmin (DES), beta-actin promoters, insulin promoters, enolase promoters, BDNF promoters, NGF promoters, EGF promoters, growth factor promoters, axon-specific promoters, dendrite-specific promoters, brain-specific promoters, hippocampal-specific promoters, kidney-specific promoters, elafin promoters, cytokine promoters, interferon promoters, growth factor promoters, alpha-1 antitrypsin promoters, brain-specific promoters, neural cell-specific promoters, central nervous system cell-specific promoters, peripheral nervous system cell-specific promoters, interleukin promoters, serpin promoters, hybrid CMV promoters, hybrid .beta.-actin promoters, EF1 promoters, U1a promoters, U1b promoters, Tet-inducible promoters and VP16-LexA promoters. In exemplary embodiments, the promoter is a mammalian or avian beta-actin promoter.

Exemplary enhancer sequences include, but are not limited to, one or more selected from the group consisting of CMV enhancers, synthetic enhancers, liver-specific enhancers, vascular-specific enhancers, brain-specific enhancers, neural cell-specific enhancers, lung-specific enhancers, muscle-specific enhancers, kidney-specific enhancers, pancreas-specific enhancers, and islet cell-specific enhancers.

Exemplary therapeutic agents include, but are not limited to, an agent selected from the group consisting of polypeptides, peptides, antibodies, antigen binding fragments, ribozymes, peptide nucleic acids, siRNA, RNAi, antisense oligonucleotides and antisense polynucleotides.

In exemplary embodiments, the rAAV vectors of the invention will encode a therapeutic protein or polypeptide selected from the group consisting of adrenergic agonists, anti-apoptosis factors, apoptosis inhibitors, cytokine receptors, cytokines, cytotoxins, erythropoietic agents, glutamic acid decarboxylases, glycoproteins, growth factors, growth factor receptors, hormones, hormone receptors, interferons, interleukins, interleukin receptors, kinases, kinase inhibitors, nerve growth factors, netrins, neuroactive peptides, neuroactive peptide receptors, neurogenic factors, neurogenic factor receptors, neuropilins, neurotrophic factors, neurotrophins, neurotrophin receptors, N-methyl-D-aspartate antagonists, plexins, proteases, protease inhibitors, protein decarboxylases, protein kinases, protein kinase inhibitors, proteolytic proteins, proteolytic protein inhibitors, semaphorin a semaphorin receptors, serotonin transport proteins, serotonin uptake inhibitors, serotonin receptors, serpins, serpin receptors, and tumor suppressors.

In certain applications, the modified high-transduction efficiency vectors may comprise a nucleic acid segment that encodes a polypeptide selected from the group consisting of BDNF, CNTF, CSF, EGF, FGF, G-SCF, GM-CSF, gonadotropin, IFN, IFG-1, M-CSF, NGF, PDGF, PEDF, TGF, TGF-B2, TNF, VEGF, prolactin, somatotropin, XIAP1, IL-1, IL-2, IL-3, IL-4, IL-5, IL-6, IL-7, IL-8, IL-9, IL-10, IL-10(187A), viral IL-10, IL-11, IL-12, IL-13, IL-14, IL-15, IL-16, IL-17, and IL-18. Such therapeutic agents may be of human, murine, avian, porcine, bovine, ovine, feline, canine, equine, epine, caprine, lupine or primate origin.

Recombinant AAV vectors useful according to the invention include single-stranded (ss) or self-complementary (sc) AAV vectors.

The rAAV vectors of the present invention may also be within an isolated mammalian host cell, including for example, human, primate, murine, feline, canine, porcine, ovine, bovine, equine, epine, caprine and lupine host cells. The rAAV vectors may be within an isolated mammalian host cell such as a human endothelial, epithelial, vascular, liver, lung, heart, pancreas, intestinal, kidney, cardiac, cancer or tumor, muscle, bone, neural, blood, or brain cell.

Therapeutic Uses

Another aspect of the invention pertains to uses of the rAAV vectors and virions of the invention for efficient transduction of cells, tissues, and/or organs of interest, and/or for use in gene therapy.

In one embodiment, the present invention provides a method for transduction of cells, tissues, and/or organs of interest, comprising introducing into a cell, a composition comprising an effective amount of a rAAV vector and/or virion of present invention.

In certain embodiments, rAAV vectors and virions of the invention are used for transduction of mammalian host cells, including for example, human, primate, murine, feline, canine, porcine, ovine, bovine, equine, epine, caprine and lupine host cells. In certain embodiments, the rAAV vectors and virions of the invention are used for transduction of endothelial, epithelial, vascular, liver, lung, heart, pancreas, intestinal, kidney, muscle, bone, dendritic, cardiac, neural, blood, brain, fibroblast or cancer cells.

In one embodiment, cells, tissues, and/or organs of a subject are transduced using the rAAV vectors and/or virions of the present invention.

The term "subject," as used herein, describes an organism, including mammals such as primates, to which treatment with the compositions according to the present invention can be provided. Mammalian species that can benefit from the disclosed methods of treatment include, but are not limited to, apes; chimpanzees; orangutans; humans; monkeys; domesticated animals such as dogs and cats; livestock such as horses, cattle, pigs, sheep, goats, and chickens; and other animals such as mice, rats, guinea pigs, and hamsters.

In addition, the present invention provides a method for treatment of a disease, wherein the method comprises administering, to a subject in need of such treatment, an effective amount of a composition comprising the rAAV vector and/or virion of the invention.

The term "treatment" or any grammatical variation thereof (e.g., treat, treating, and treatment etc.), as used herein, includes but is not limited to, alleviating a symptom of a disease or condition; and/or reducing, suppressing, inhibiting, lessening, ameliorating or affecting the progression, severity, and/or scope of a disease or condition.

The term "effective amount," as used herein, refers to an amount that is capable of treating or ameliorating a disease or condition or otherwise capable of producing an intended therapeutic effect.

The invention also provides for the use of a composition disclosed herein in the manufacture of a medicament for treating, preventing or ameliorating the symptoms of a disease, disorder, dysfunction, injury or trauma, including, but not limited to, the treatment, prevention, and/or prophylaxis of a disease, disorder or dysfunction, and/or the amelioration of one or more symptoms of such a disease, disorder or dysfunction.

Exemplary conditions for which rAAV viral based gene therapy may find particular utility include, but are not limited to, cancer, diabetes, autoimmune disease, kidney disease, cardiovascular disease, pancreatic disease, intestinal disease, liver disease, neurological disease, neuromuscular disorder, neuromotor deficit, neuroskeletal impairment, neurological disability, neurosensory dysfunction, stroke, .alpha..sub.1-antitrypsin (AAT) deficiency, Batten's disease, ischemia, an eating disorder, Alzheimer's disease, Huntington's disease, Parkinson's disease, skeletal disease and pulmonary disease.

The invention also provides a method for treating or ameliorating the symptoms of such a disease, injury, disorder, or dysfunction in a mammal. Such methods generally involve at least the step of administering to a mammal in need thereof, one or more of the rAAV vectors and virions of the present invention, in an amount and for a time sufficient to treat or ameliorate the symptoms of such a disease, injury, disorder, or dysfunction in the mammal.

Such treatment regimens are particularly contemplated in human therapy, via administration of one or more compositions either intramuscularly, intravenously, subcutaneously, intrathecally, intraperitoneally, or by direct injection into an organ or a tissue of the subject under care.

The invention also provides a method for providing to a mammal in need thereof, a therapeutically-effective amount of the rAAV compositions of the present invention, in an amount, and for a time effective to provide the patient with a therapeutically-effective amount of the desired therapeutic agent(s) encoded by one or more nucleic acid segments comprised within the rAAV vector. Preferably, the therapeutic agent is selected from the group consisting of a polypeptide, a peptide, an antibody, an antigen binding fragment, a ribozyme, a peptide nucleic acid, a siRNA, an RNAi, an antisense oligonucleotide and an antisense polynucleotide.

Pharmaceutical Compositions

The present invention also provides therapeutic or pharmaceutical compositions comprising the active ingredient in a form that can be combined with a therapeutically or pharmaceutically acceptable carrier. The genetic constructs of the present invention may be prepared in a variety of compositions, and may also be formulated in appropriate pharmaceutical vehicles for administration to human or animal subjects.

The rAAV molecules of the present invention and compositions comprising them provide new and useful therapeutics for the treatment, control, and amelioration of symptoms of a variety of disorders, and in particular, articular diseases, disorders, and dysfunctions, including for example osteoarthritis, rheumatoid arthritis, and related disorders.

The invention also provides compositions comprising one or more of the disclosed rAAV vectors, expression systems, virions, viral particles; or mammalian cells. As described hereinbelow, such compositions may further comprise a pharmaceutical excipient, buffer, or diluent, and may be formulated for administration to an animal, and particularly a human being. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Such compositions may be formulated for use in a variety of therapies, such as example, in the amelioration, prevention, and/or treatment of conditions such as peptide deficiency, polypeptide deficiency, peptide overexpression, polypeptide overexpression, including for example, conditions which result in diseases or disorders such as cancers, tumors, or other malignant growths, neurological deficit dysfunction, autoimmune diseases, articular diseases, cardiac or pulmonary diseases, ischemia, stroke, cerebrovascular accidents, transient ischemic attacks (TIA); diabetes and/or other diseases of the pancreas; cardiocirculatory disease or dysfunction (including, e.g., hypotension, hypertension, atherosclerosis, hypercholesterolemia, vascular damage or disease; neural diseases (including, e.g., Alzheimer's, Huntington's, Tay-Sach's and Parkinson's disease, memory loss, trauma, motor impairment, neuropathy, and related disorders); biliary, renal or hepatic disease or dysfunction; musculoskeletal or neuromuscular diseases (including, e.g., arthritis, palsy, cystic fibrosis (CF), amyotrophic lateral sclerosis (ALS), multiple sclerosis (MS), muscular dystrophy (MD), and such like).

In one embodiment, the number of rAAV vector and/or virion particles administered to a mammal may be on the order ranging from $10^3$ to $10^{13}$ particles/ml, or any values therebetween, such as for example, about $10^7$, $10^8$, $10^9$, $10^{10}$, $10^{11}$, $10^{12}$, or $10^{13}$ particles/ml. In one embodiment, rAAV vector and/or virion particles of higher than $10^{13}$ particles/ml are be administered. The rAAV vectors and/or virions can be administered as a single dose, or divided into two or more administrations as may be required to achieve therapy of the particular disease or disorder being treated. In most rAAV-based gene therapy regimens, the inventors believe that a lower titer of infectious particles will be required when using the modified-capsid rAAV vectors, than compared to conventional gene therapy protocols.

In certain embodiments, the present invention concerns formulation of one or more rAAV-based compositions disclosed herein in pharmaceutically acceptable solutions for administration to a cell or an animal, either alone or in combination with one or more other modalities of therapy, and in particular, for therapy of human cells, tissues, and diseases affecting man.

If desired, nucleic acid segments, RNA, DNA or PNA compositions that express one or more of therapeutic gene products may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV-based genetic compositions may thus be delivered along with various other agents as required in the particular instance. Such compositions may be purified from host cells or other biological sources, or alternatively may be chemically synthesized as described herein. Likewise, such compositions may further comprise substituted or derivatized RNA, DNA, siRNA, mRNA, tRNA, ribozyme, catalytic RNA molecules, or PNA compositions and such like.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intra-articular, intramuscular administration and formulation.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound(s) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the AAV vector-based therapeutic constructs in suitably formulated pharmaceutical compositions disclosed herein either subcutaneously, intraocularly, intravitreally, parenterally, subcutaneously, intravenously, intracerebro-ventricularly, intramuscularly, intrathecally, orally, intraperitoneally, by oral or nasal inhalation, or by direct injection to one or more cells, tissues, or organs by direct injection. The methods of administration may also include those modalities as described in U.S. Pat. Nos. 5,543,158, 5,641,515 and/or 5,399,363 (each of which is specifically incorporated herein in its entirety by express reference thereto). Solutions of the active compounds as freebase or pharmacologically acceptable salts may be prepared in sterile water and may also suitably mixed with one or more surfactants, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms of the AAV-based viral compositions suitable for injectable use include sterile aqueous solutions or dispersions and sterile powders for the extemporaneous preparation of sterile injectable solutions or dispersions (U.S. Pat. No. 5,466,468, specifically incorporated herein in its entirety by express reference thereto). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers.

The compositions of the present invention can be administered to the subject being treated by standard routes including, but not limited to, pulmonary, intranasal, oral, inhalation, parenteral such as intravenous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection. In preferred embodiments, the composition is administered via intranasal, pulmonary, or oral route.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active AAV vector-delivered therapeutic polypeptide-encoding DNA fragments in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The AAV vector compositions disclosed herein may also be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

The amount of AAV compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the AAV vector compositions, either over a relatively short, or a relatively prolonged period of time, as may be determined by the medical practitioner overseeing the administration of such compositions.

Expression Vectors

The present invention contemplates a variety of AAV-based expression systems, and vectors. In one embodiment the preferred AAV expression vectors comprise at least a first nucleic acid segment that encodes a therapeutic peptide, protein, or polypeptide. In another embodiment, the preferred AAV expression vectors disclosed herein comprise at least a first nucleic acid segment that encodes an antisense molecule. In another embodiment, a promoter is operatively linked to a sequence region that encodes a functional mRNA, a tRNA, a ribozyme or an antisense RNA.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the functional RNA to which it is operatively linked.

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

To express a therapeutic agent in accordance with the present invention one may prepare a tyrosine-modified rAAV expression vector that comprises a therapeutic agent-encoding nucleic acid segment under the control of one or more promoters. To bring a sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded polypeptide. This is the meaning of "recombinant expression" in this context. Particularly preferred recombinant vector constructs are those that comprise a rAAV vector. Such vectors are described in detail herein.

When the use of such vectors is contemplated for introduction of one or more exogenous proteins, polypeptides, peptides, ribozymes, and/or antisense oligonucleotides, to a particular cell transfected with the vector, one may employ the rAAV vectors or the tyrosine-modified rAAV vectors disclosed herein by genetically modifying the vectors to further comprise at least a first exogenous polynucleotide operably positioned downstream and under the control of at least a first heterologous promoter that expresses the polynucleotide in a cell comprising the vector to produce the encoded peptide, protein, polypeptide, ribozyme, siRNA, RNAi or antisense oligonucleotide. Such constructs may employ heterologous promoters that are constitutive, inducible, or even cell-specific promoters. Exemplary such promoters include, but are not limited to, viral, mammalian, and avian promoters, including for example a CMV promoter, a .beta.-actin promoter, a hybrid CMV promoter, a hybrid .beta.-actin promoter, an EF1 promoter, a U1a promoter, a U1b promoter, a Tet-inducible promoter, a VP16-LexA promoter, and such like.

The vectors or expression systems may also further comprise one or more enhancers, regulatory elements, transcriptional elements, to alter or effect transcription of the heterologous gene cloned in the rAAV vectors. For example, the rAAV vectors of the present invention may further comprise at least a first CMV enhancer, a synthetic enhancer, or a cell- or tissue-specific enhancer. The exogenous polynucleotide may also further comprise one or more intron sequences.

Therapeutic Kits

The invention also encompasses one or more of the genetically-modified rAAV vector compositions described herein together with one or more pharmaceutically-acceptable excipients, carriers, diluents, adjuvants, and/or other components, as may be employed in the formulation of particular rAAV-polynucleotide delivery formulations, and in the preparation of therapeutic agents for administration to a subject, and in particularly, to a human. In particular, such kits may comprise one or more of the disclosed rAAV compositions in combination with instructions for using the viral vector in the treatment of such disorders in a subject, and may typically further include containers prepared for convenient commercial packaging.

As such, preferred animals for administration of the pharmaceutical compositions disclosed herein include mammals, and particularly humans. Other preferred animals include murines, bovines, equines, poreines, canines, and felines. The composition may include partially or significantly purified rAAV compositions, either alone, or in combination with one or more additional active ingredients, which may be obtained from natural or recombinant sources, or which may be obtainable naturally or either chemically synthesized, or alternatively produced in vitro from recombinant host cells expressing DNA segments encoding such additional active ingredients.

Therapeutic kits may also be prepared that comprise at least one of the compositions disclosed herein and instructions for using the composition as a therapeutic agent. The container means for such kits may typically comprise at least one vial, test tube, flask, bottle, syringe or other container means, into which the disclosed rAAV composition(s) may be placed, and preferably suitably aliquoted. Where a second therapeutic polypeptide composition is also provided, the kit may also contain a second distinct container means into which this second composition may be placed. Alternatively, the plurality of therapeutic biologically active compositions may be prepared in a single pharmaceutical composition, and may be packaged in a single container means, such as a vial, flask, syringe, bottle, or other suitable single container means. The kits of the present invention will also typically include a means for containing the vial(s) in close confinement for commercial sale, such as, e.g., injection or blow-molded plastic containers into which the desired vial(s) are retained.

AAV Capsid Proteins

Supramolecular assembly of 60 individual capsid protein subunits into a non-enveloped, T-1 icosahedral lattice capable of protecting a 4.7-kb single-stranded DNA genome is a critical step in the life-cycle of the helper-dependent human parvovirus, adeno-associated virus2 (AAV2). The mature 20-nm diameter AAV2 particle is composed of three structural proteins designated VP1, VP2, and VP3 (molecular masses of 87, 73, and 62 kDa respectively) in a ratio of 1:1:18. Based on its symmetry and these molecular weight estimates, of the 60 capsid proteins comprising the particle, three are VP1 proteins, three are VP2 proteins, and fifty-four are VP3 proteins.

Biological Functional Equivalents

Modification and changes to the structure of the polynucleotides and polypeptides of wild-type rAAV vectors to provide the improved rAAV virions as described in the present invention to obtain functional viral vectors that possess desirable characteristics, particularly with respect to improved delivery of therapeutic gene constructs to selected mammalian cell, tissues, and organs for the treatment, prevention, and prophylaxis of various diseases and disorders, as well as means for the amelioration of symptoms of such diseases, and to facilitate the expression of exogenous therapeutic and/or prophylactic polypeptides of interest via rAAV vector-mediated gene therapy. As mentioned above, one of the key aspects of the present invention is the creation of one or more mutations into specific polynucleotide sequences that encode one or more of the therapeutic agents encoded by the disclosed rAAV constructs. In certain circumstances, the resulting polypeptide sequence is altered by these mutations, or in other cases, the sequence of the polypeptide is unchanged by one or more mutations in the encoding polynucleotide to produce modified vectors with improved properties for effecting gene therapy in mammalian systems.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the polynucleotide sequences disclosed herein, without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Exemplary Definitions

In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

The term "promoter," as used herein refers to a region or regions of a nucleic acid sequence that regulates transcription.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "vector," as used herein, refers to a nucleic acid molecule (typically comprised of DNA) capable of replication in a host cell and/or to which another nucleic acid segment can be operatively linked so as to bring about replication of the attached segment. A plasmid, cosmid, or a virus is an exemplary vector.

The term "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

Desirably, which highly homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (Proc. Natl. Acad. Sci. USA, 85(8): 2444-8, April 1988).

The term "operably linked," as used herein, refers to that the nucleic acid sequences being linked are typically contiguous, or substantially contiguous, and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

EXAMPLES

Following are examples that illustrate procedures and embodiments for practicing the invention. The examples should not be construed as limiting.

Materials and Methods:

Cells and antibodies: HEK293, HeLa, NIH3T3 cells were obtained from the American Type Culture Collection (Manassas, VA, USA) and maintained as monolayer cultures in DMEM (Invitrogen) supplemented with 10% FBS (Sigma-Aldrich, St. Louis, MO, USA) and antibiotics (Lonza). Leukapheresis-derived peripheral blood mononuclear cells (PBMCs) (AllCells) were purified on Ficoll-Paque (GE-HeathCare), re-suspended in serum-free AIM-V medium (Lonza), and semi-adherent cell fractions were incubated for 7 days with recombinant human IL-4 (500 U/mL) and GM-CSF (800 U/mL) (R&D Systems). Cell maturation was initiated with cytokine mixture including 10 ng/mL TNF-α, ng/mL IL-1, 10 ng/mL IL-6, and 1 mg/mL PGE2 (R&D Systems) for 48 hrs. Prior to EGFP expression, cells were characterized for co-stimulatory molecules expression to ensure that they met the typical phenotype of mature dendritic cells (mDC) (CD80, RPE, murine IgG1; CD83, RPE, murine IgG1; CD86, FITC, murine IgG1; Invitrogen).

Site-directed mutagenesis: A two-stage PCR was performed with plasmid pACG2 as described previously (Wang et al., 1999) using Turbo® Pfu Polymerase (Stratagene). Briefly, in stage one, two PCR extension reactions were performed in separate tubes for the forward and reverse PCR primer for 3 cycles. In stage two, the two reactions were mixed and a PCR reaction was performed for an additional 15 cycles, followed by DpnI digestion for one hr. Primers were designed to introduce changes from serine (TCA or AGC) to valine (GTA or GTC) for each of the residues mutated.

Production of recombinant AAV vectors: Recombinant AAV2 vectors containing the EGFP gene driven by the Chicken®-actin promoter were generated as described previously (Zolotukhin, 2002). Briefly, HEK293 cells were transfected using Polyethelenimine (PEI, linear, MW 25,000, Polysciences, Inc.). Seventy-two hrs' post transfection, cells were harvested and vectors were purified by iodixanol (Sigma-Aldrich) gradient centrifugation and ion exchange column chromatography (HiTrap Sp Hp 5 mL, GE Healthcare). Virus was then concentrated and the buffer was exchanged in three cycles to lactated Ringer's using centrifugal spin concentrators (Apollo, 150-kDa cut-off 20-mL capacity, CLP) (Cheng et al., 2011). Ten L of purified virus was treated with DNAse I (Invitrogen) for 2 hrs at 37° C., then additional 2 hrs with proteinase K (Invitrogen) at 56° C. The reaction mixture was purified by phenol/chloroform, followed by chloroform treatment. Packaged DNA was precipitated with ethanol in the presence of 20 μg glycogen (Invitrogen). DNAse I-resistant AAV particle titers were determined by RT-PCR with the following primers-pair, specific for the CBA promoter:

forward 5'-TCCCATAGTAACGCCAATAGG-3' (SEQ ID NO: 11)
reverse 5'-CTTGGCATATGATACACTTGATG-3' (SEQ ID NO:12) and SYBR Green PCR Master Mix (Invitrogen).

Recombinant AAV vector transduction assays in vitro: HEK293 or monocyte-derived dendritic cells (moDCs), were transduced with AAV2 vectors with 1,000 vgs/cell or 2,000 vgs/cell respectively, and incubated for 48 hrs. Alternatively, cells were pretreated with 50 μM of selective serine/threonine kinases inhibitors 2-(2-hydroxyethylamino)-6-aminohexylcarbamic acid tert-butyl ester-9-isopropylpurine (for CaMK-II), anthra[1,9-cd]pyrazol-6(2H)-one, 1,9-pyrazoloanthrone (for JNK), and 4-(4-fluorophenyl)-2-(4-methylsulfinylphenyl)-5-(4-pyridyl)1H-imidazole (for MAPK) (CK59, JNK inhibitor 2, PD 98059, Calbiochem), 1 hr before transduction. Transgene expression was assessed as the total area of green fluorescence (pixel$^2$) per visual field (mean±SD) or by flow cytometry as described previously (Markusic et al., 2011; Jayandharan et al., 2011). Analysis of variance was used to compare test results and the control, which were determined to be statistically significant.

Western blot analysis: Western blot analysis was performed as described previously (Aslanidi et al., 2007). Cells were harvested by centrifugation, washed with PBS, and resuspended in lysis buffer containing 50 mM Tris_HCl, pH 7.5, 120 mM NaCl, 1% Nonidet P-40, 10% glycerol, 10 mM Na$_4$P$_2$O$_7$, 1 mM phenylmethylsulfonyl fluoride (PMSF), 1 mM EDTA, and 1 mM EGTA supplemented with protease and phosphatase inhibitors mixture (Set 2 and 3, Calbiochem). The suspension was incubated on ice for 1 hr and clarified by centrifugation for 30 min at 14,000 rpm at 4° C. Following normalization for protein concentration, samples were separated using 12% polyacrylamide/SDS electrophoresis, transferred to a nitrocellulose membrane, and probed with primary antibodies, anti p-p38 MAPK (Thr180/Tyr182) rabbit mAb, total p38 MAPK rabbit mAb and GAPDH rabbit mAb (1:1000, CellSignaling), follow by secondary horseradish peroxidase-linked linked antibodies (1:1000, CellSignaling).

Specific cytotoxic T-lymphocytes generation and cytotoxicity assay: Monocytes-derived dendritic cells (moDCs) were generated as described above. Immature DCs were infected with AAV2-S662V vectors encoding human telomerase cDNA (Dr. Karina Krotova, University of Florida), separated into two overlapping ORF-hTERT$_{838-2229}$ and hTERT$_{2042-3454}$ at MOI 2,000 vgs/cell of each. Cells were then allowed to undergo stimulation with supplements to induce maturation. After 48 hr, the mature DCs expressing hTERT were harvested and mixed with the PBMCs at a ratio of 20:1. CTLs were cultured in AIM-V medium containing recombinant human IL-15 (20 IU/ml) and IL-7 (20 ng/mL) at 20×10$^6$ cells in 25 cm$^2$ flasks. Fresh cytokines were added every 2 days. After 7 days post-priming, the cells were harvested and used for killing assays (Heiser et al., 2002). A killing curve was generated and specific cell lysis was determined by FACS analysis of live/dead cell ratios as described previously (Mattis et al., 1997). Human immortalized myelogenous leukemia cell line, K562, was used as a target.

Statistical analysis: Results were presented as mean±S.D. Differences between groups were identified using a grouped-unpaired two-tailed distribution of Student's 1-test. P-values<0.05 were considered statistically significant.

Example 1—Inhibition of Specific Cellular Serine/Threonine Kinase Increases Transduction Efficiency of RAAV2 Vectors Inhibition of cellular epidermal growth factor receptor protein tyrosine kinase (EGFR-PTK) activity, as well as site-directed mutagenesis of the seven surface-exposed tyrosine residues significantly increased the transduction efficiency of AAV2 vectors by preventing phosphorylation of these residues, thereby circumventing ubiquitination and subsequent proteasome-mediated degradation of the vectors. AAV2 capsids also contain fifteen surface-exposed serine residues, which can potentially be phosphorylated by cellular serine/threonine kinases widely expressed in various cell types and tissues.

To examine whether inhibition of such kinase activity can prevent phosphorylation of surface-exposed serine residues, and thus, improve intracellular trafficking and nuclear transport of AAV2 vectors, several commercially available specific inhibitors of cellular serine/threonine kinases, such as calmodulin-dependent protein kinase II (CamK-II), c-Jun N-terminal kinase (JNK), and mitogen-activated protein kinase (p38 MAPK), were used. HEK293 cells were pretreated with specific inhibitors, such as 2-(2-hydroxyethylamino)-6-aminohexylcarbamic acid tert-butyl ester-9-isopropylpurine (for CaMK-II), anthra[1,9-cd]pyrazol-6(2H)-one, 1,9-pyrazoloanthrone (for JNK), and 4-(4-fluorophenyl)-2-(4-methylsulfinylphenyl)-5-(4-pyridyl)1H-imidazole (for p38 MAPK) for 1 hr at various concentrations. Cells were subsequently transduced with either single-stranded (ss) or self-complementary (sc) AAV2 vectors at 1,000 vector genomes (vgs) per cell.

Figure 3A:
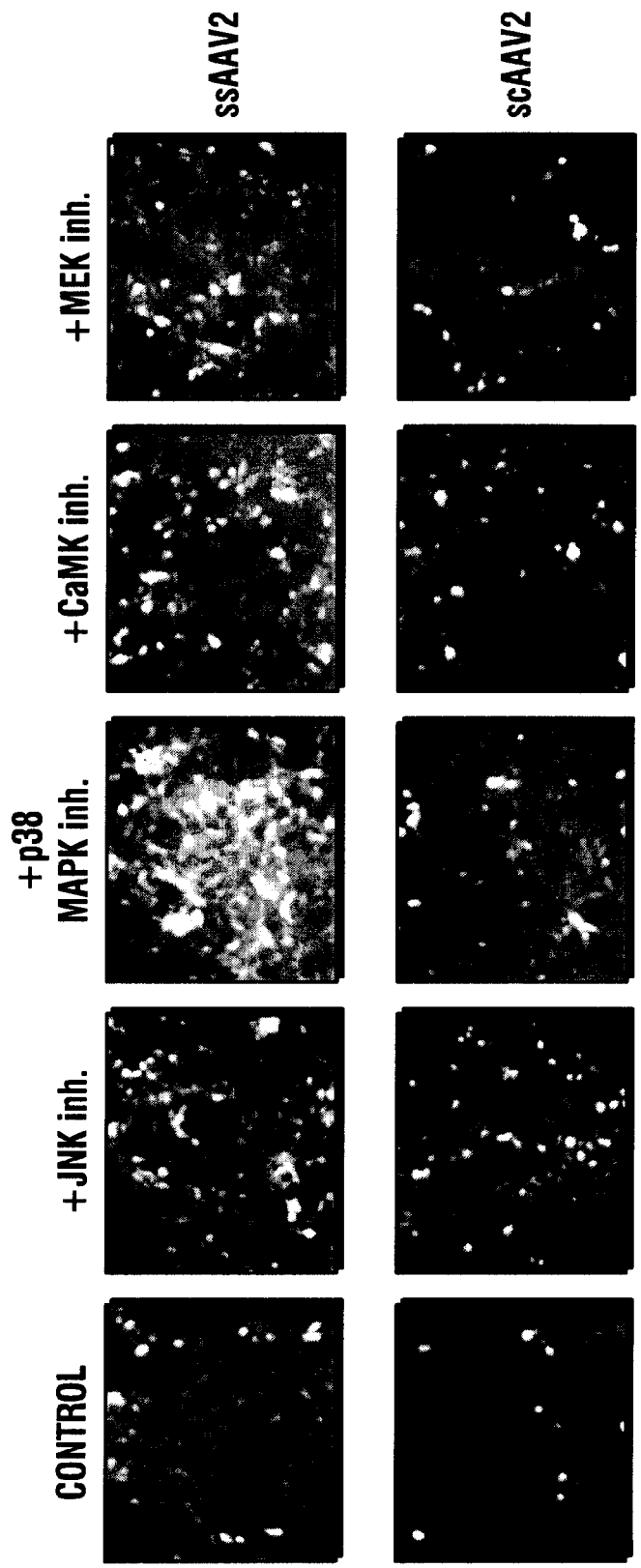
FIG. 3A and FIG. 3B show the effect of various kinase inhibitors on ssAAV and scAAV mediated EGFP expression in HEK293 cells. Cells were pretreated with inhibitors for 1 hr before infection and then transduced with $1 \times 10^3$ vgs/cell.
Figure 3B:
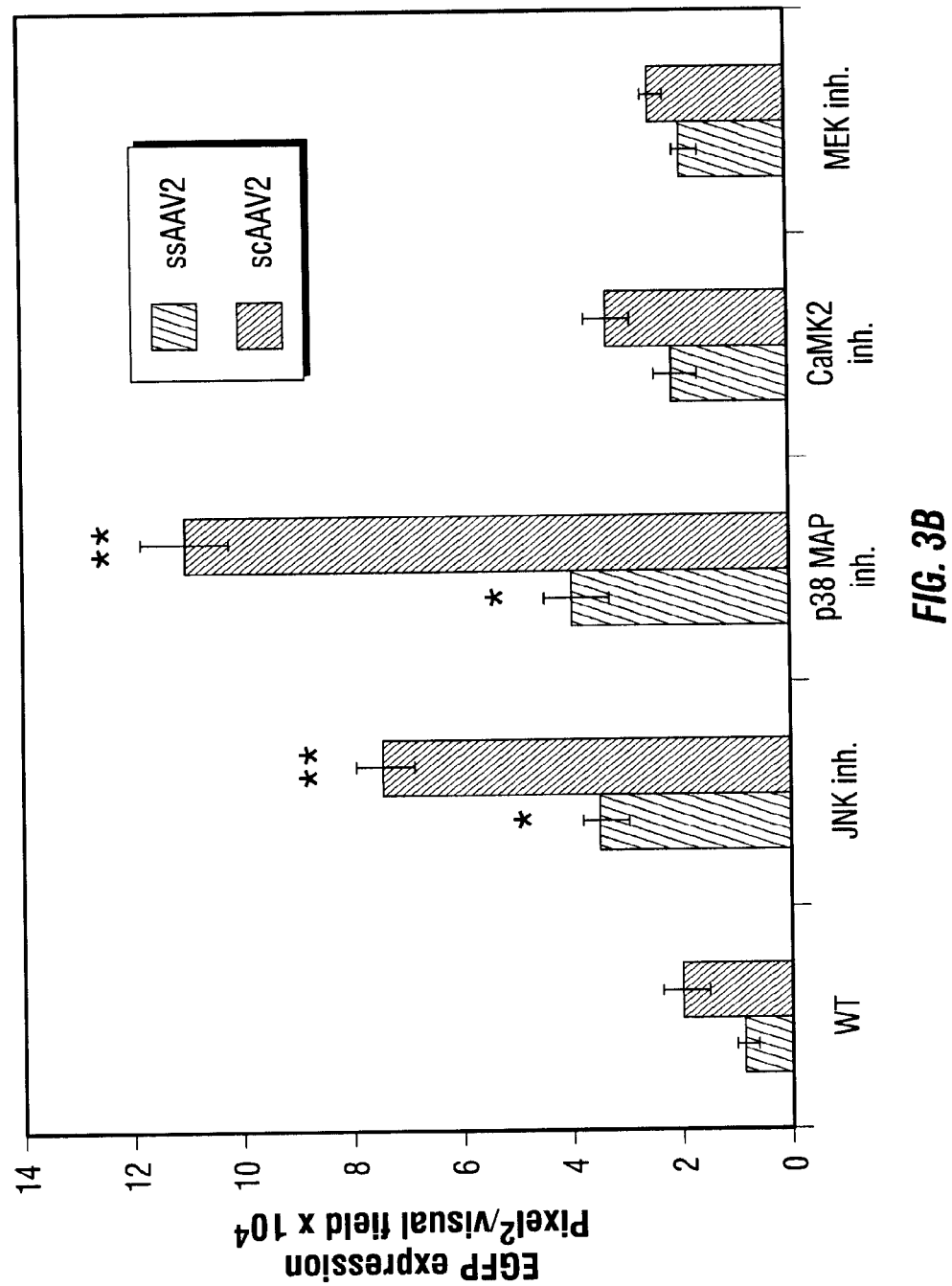

These results show that all inhibitors at a concentration of 50 µM significantly increased the transduction efficiency of ssAAV2 and scAAV2 vectors, the p38 MAPK inhibitor being the most effective (FIG. 3A and FIG. 3B). The results indicate that the increase in the transduction efficiency was due to prevention of phosphorylation of vector capsids rather than improved viral second-strand DNA synthesis.

Example 2—Site-Directed Mutagenesis of Surface-Exposed Serine Residues Improves Vector-Mediated Transgene Expression The AAV2 capsid contains 50 serine (S) residues in the viral protein 3 (VP3) common region of the three capsid VPs, of which 15 residues (S261, S264, S267, S276, S384, S458, S468, S492, S498, S578, S658, S662, S668, S707, S721) are surface-exposed. Each of the 15 S residues was substituted with valine (V) residues by site-directed mutagenesis as described previously. Most mutants could be generated at titers similar to the WT AAV2 vectors, with the exception of S261V, S276V, and S658V, which were produced at ~10 times lower titers, and S267V and S668V, which produced no detectable levels of DNAse I-resistant vector particles. The titers of S468V and S384V mutants were ~3-5 times higher than the WT AAV2 vectors. Each of the S-V mutant vectors was evaluated for transduction efficiency in 293 cells.

Figure 4A:
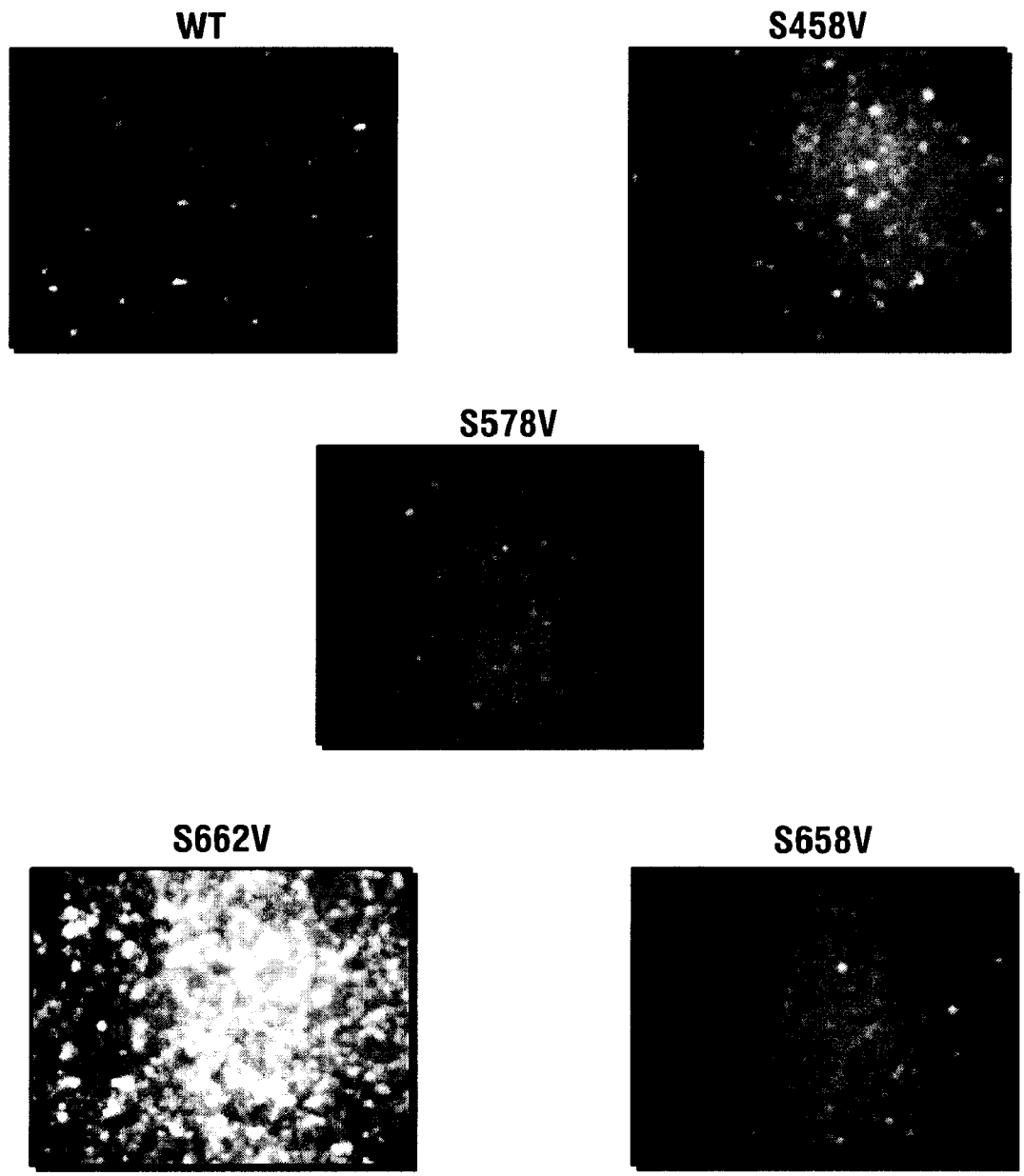
FIG. 4A and FIG. 4B show an analysis of EGFP expression after transduction of 293 cells with individual site-directed AAV2 capsid mutants. Each of the 15 surface-exposed serines (S) in AAV2 capsid was substituted with valine (V) and evaluated for its efficiency to mediate transgene expression.
Figure 4B:
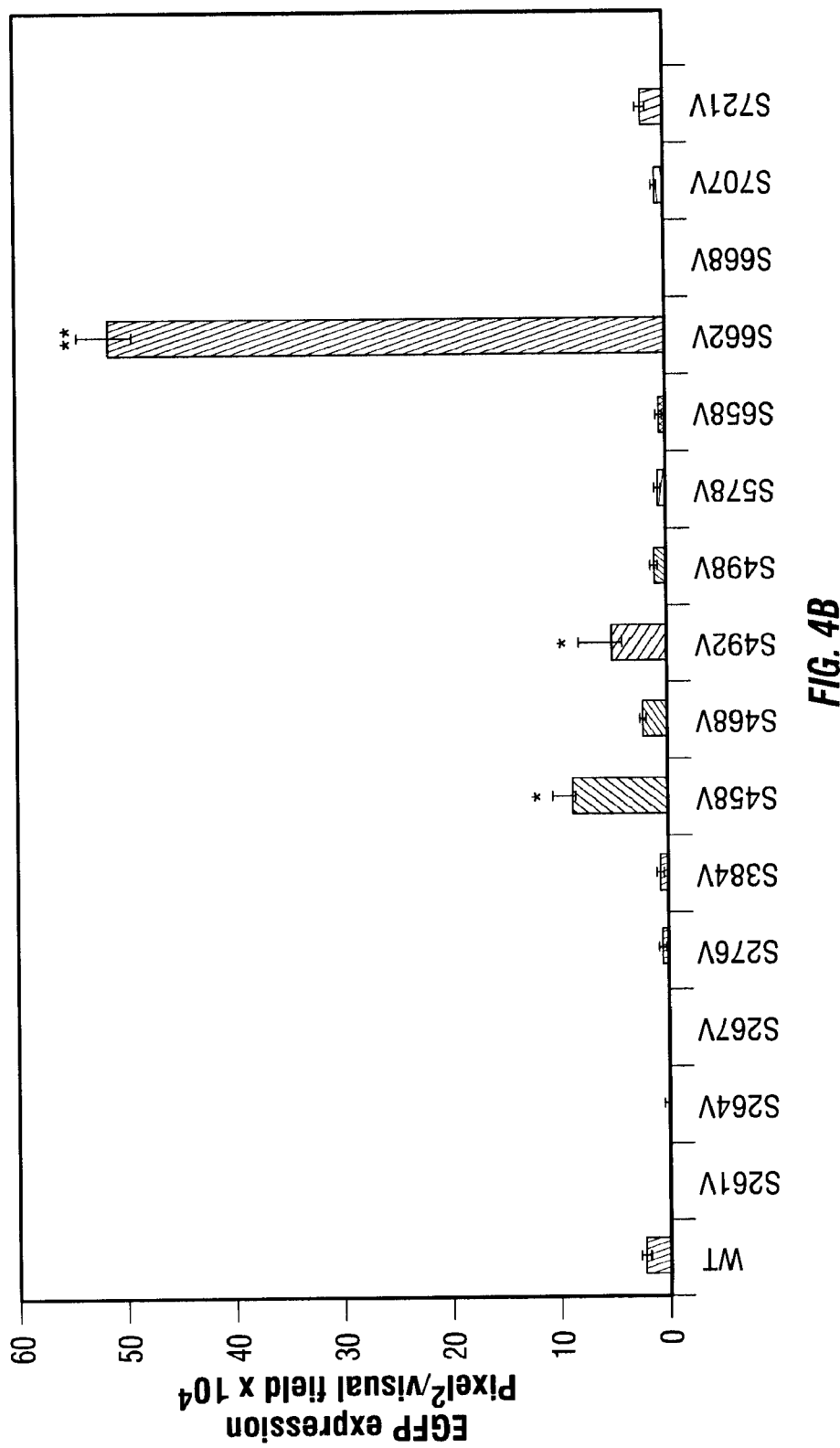

These results, shown in FIG. 4A and FIG. 4B, indicated that of the 15 mutants, the S662V mutant transduced 293 cells ~20-fold more efficiently than its WT counterpart. The transduction efficiency of the S458V and the S492V mutant vectors was increased by ~4- and 2-fold, respectively. The transduction efficiency of the S468V and the S384V mutants, which were produced at titers higher than the WT AAV2 vectors, either remained unchanged (S468V), or reduced ~10-fold (S384V) at the same multiplicity of infection (MOI). The transduction efficiency of various serine-to-valine mutated AAV2 vectors is summarized in FIG. 5. Surprisingly, no further increase in transduction efficiency was observed in vectors containing either of the double-mutants (S458V+S662V and S492V+S662V), or in a vector that contained the triple-mutant (S458V+S492V+S662V).

Example 3—Substitution of S662 with Various Amino Acids

In addition to the S-to-V substitution at position 662, the following seven mutants were also generated with different amino acid substitutions: S662→Alanine (A), S662→Asparagine (N), S662→Aspartic acid (D), S662→Histidine (H), S662→Isoleucine (I), S662→Leucine (L), and S662→Phenylalanine (F). The transduction efficiency of each of these mutant vectors was also evaluated in 293 cells similar to that as described above.

Figure 6A:
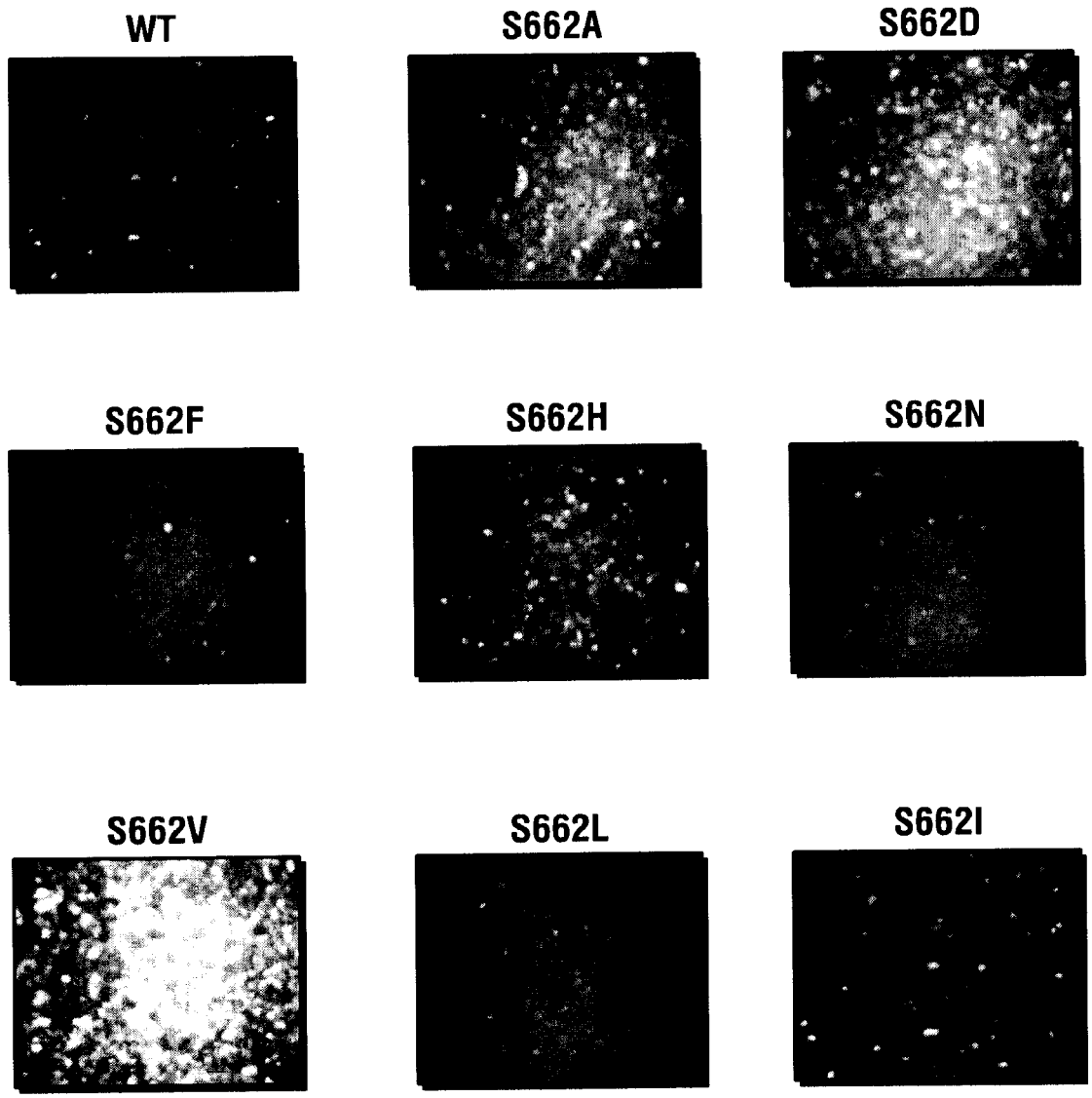
FIG. 6A and FIG. 6B show an evaluation of the effect of serine substitution at position 662 in the AAV2 capsid with different amino acids in mediating transgene expression. The following 8 serine mutants were generated with different amino acids: S662→Valine (V), S662→Alanine (A), S662→Asparagine (N), S662→Aspartic acid (D), S662→Histidine (H), S662→Isoleucine (T), S662→Leucine (L), and S662→Phenylalanine (F), and their transduction efficiency in 293 cells was analyzed.
Figure 6B:
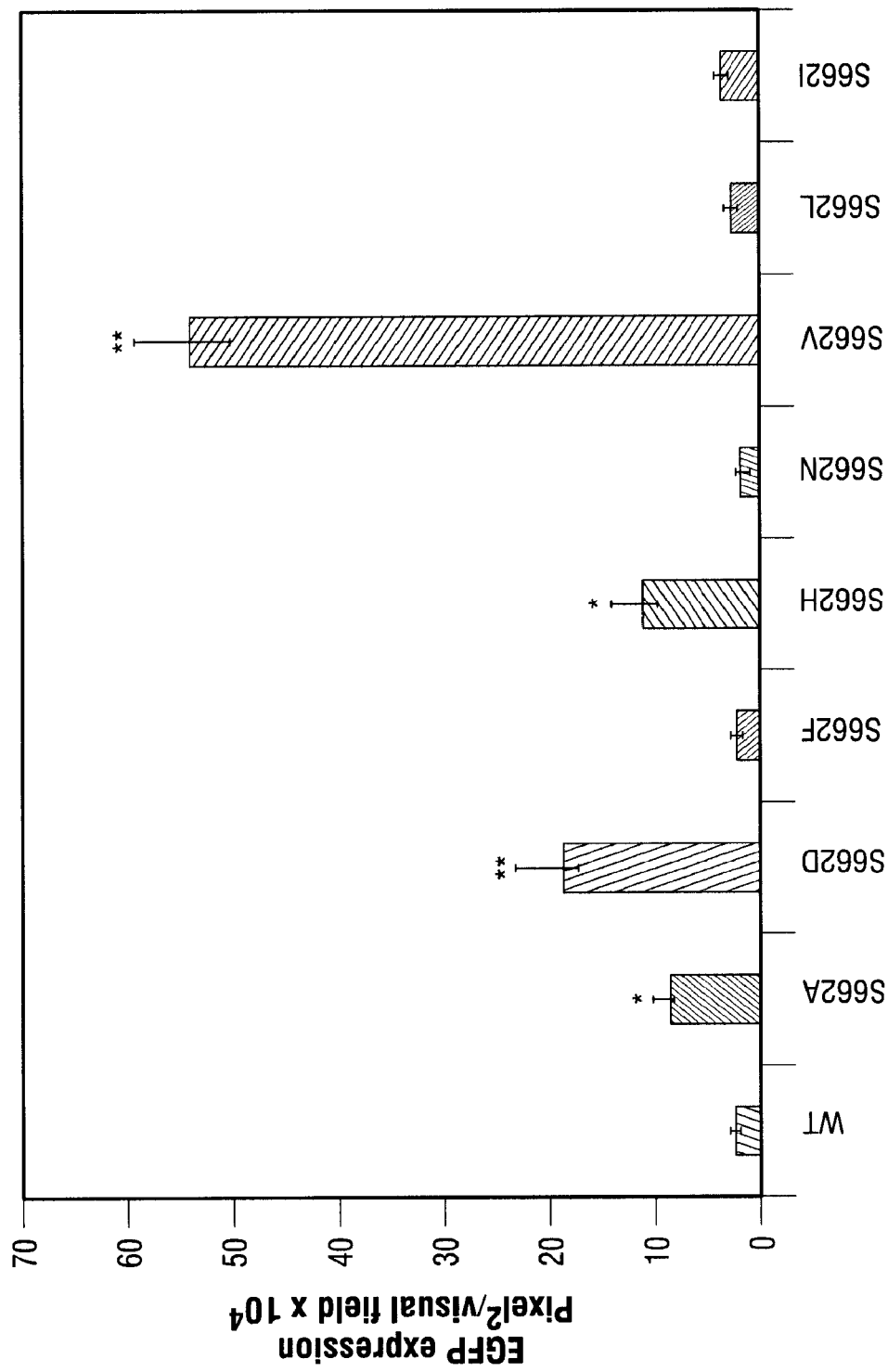

The results, as shown in FIG. 6A and FIG. 6B, and summarized in FIG. 7, demonstrate that the substitution of S with V led to production of the most efficient mutant without any change in vector titers, when compared to other mutants. Replacement of S with N, 1, L, or F decreased the packaging efficiency ~10-fold with no significant effect on the transduction efficiency, whereas substitution with D or H increased the transduction efficiency ~8-fold and ~4-fold, respectively, with no effect on vector titers. Substitution of S to A increased the viral titer up to ~5-fold, and enhanced the transgene expression ~3-fold compared with the WT AAV2 vector. The observed variability in titers and infectivity of the serine-mutants at position 662 suggests the critical role each of the amino acids plays in modulating both the AAV2 packaging efficiency and its biological activity.

Example 4—Transduction Efficiency of S662V Vectors Correlated with P38 MAPK Activity in Various Cell Types The S662V vector-mediated transgene expression is examined using the following cells types: (i) NIH3T3 (mouse embryonic fibroblasts), (ii) H2.35 (mouse fetal hepatocytes), (iii) Hela (human cervical cancer cells), and (iv) primary human monocyte-derived dendritic cells (moDCs). These cell types were transduced with WT scAAV2-EGFP or S662V scAAV2-EGFP vectors at an MOI of 2,000 vgs per cell under identical conditions. EGFP gene expression was evaluated 48 hrs post-infection (p.i.) for HeLa, 293 and moDCs, and 5 days p.i. for H2.35 and NIH3T3 cells.

Figure 8A:
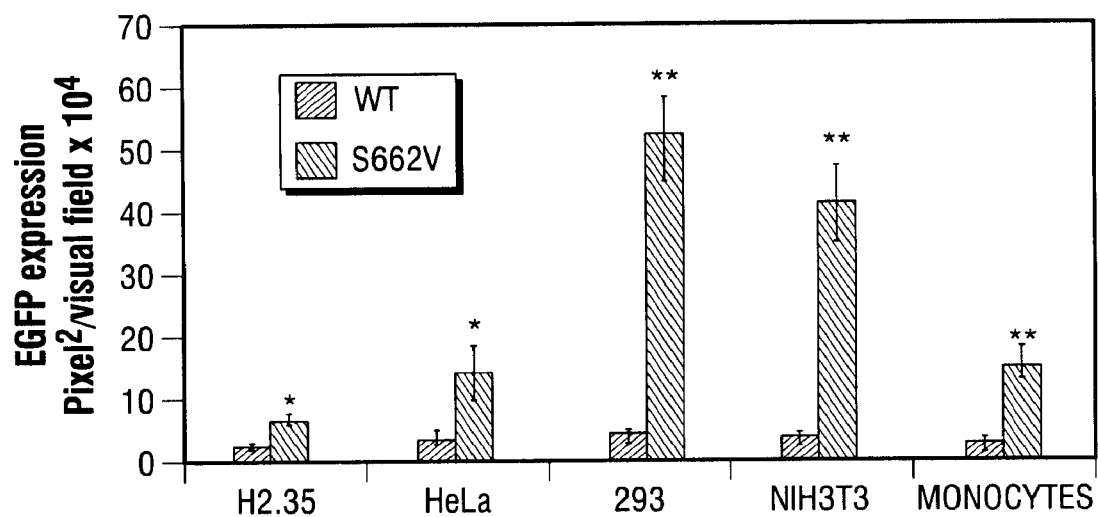
FIG. 8A and FIG. 8B show an analysis of correlation of transduction efficiency of AAV2-S662V vectors with p38 MAPK activity in various cell types.

The results, as shown in FIG. 8A, show that although the absolute differences in the transduction efficiency between WT and S662V mutant vectors ranged from ~3-fold (in H2.35 cells) to ~20-fold (in 293 cells), the mutant vector was consistently more efficient in each cell type tested.

To examine whether the observed differences in the transduction efficiency of the WT and the mutant vectors is due to variations in the levels of expression and/or activity of the cellular p38 MAPK, cell lysates prepared from each cell type were analyzed on Western blots probed with specific antibodies to detect both total p38 MAPK and phospho-p38 MAPK levels. GAPDH was used as a loading control.

Figure 8B:
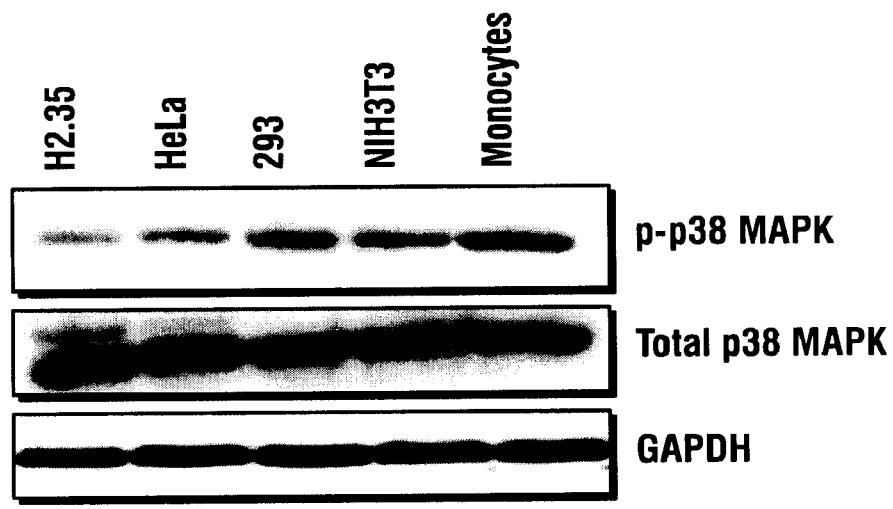

The results, as shown in FIG. 8B, indicate that while the p38 MAPK protein levels were similar, the kinase activity, as determined by the level of phosphorylation, varied significantly among different cell types, and the transduction efficiency of the S662V mutant vector correlated roughly with the p38 MAPK activity. The results show p38 MAPK-mediated phosphorylation of AAV2 vectors. In addition, transduction by the WT-AAV2 vectors did not lead to up-regulation of phosphorylation of p38 MAPK in either 293 cells or in moDCs; this indicates that AAV does not induce robust phenotypic changes in moDCs.

Example 5—S662V Mutant Vector-Mediated Transduction of moDCs Did not Lead to Phenotypic Alterations MAPK family members play important roles in the development and maturation of APCs. In this Example, moDCs, isolated from healthy donor leukapheresis, were treated with 50 µM selective kinase inhibitors as described above and then transduced with WT scAAV2-EGFP vectors. Two hrs p.i., cells were treated with supplements (TNF-α, IL-1β, Il-6, PGE2) to induce maturation. EGFP transgene expression was evaluated 48 hrs p.i. by fluorescence microscopy.

Figure 9A:
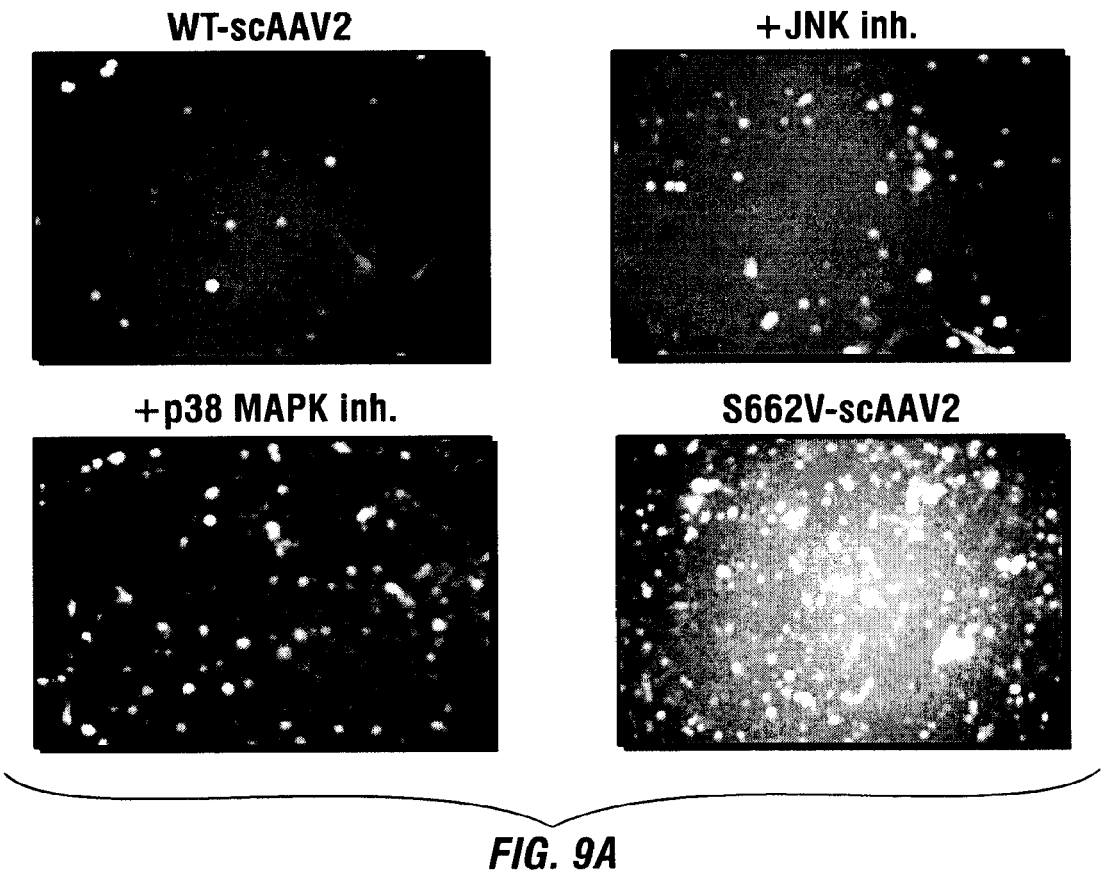
FIG. 9A, FIG. 9B, and FIG. 9C demonstrate AAV vector-mediated transgene expression in monocytes-derived dendritic cells (moDCs) in accordance with one aspect of the present invention.
Figure 9B:
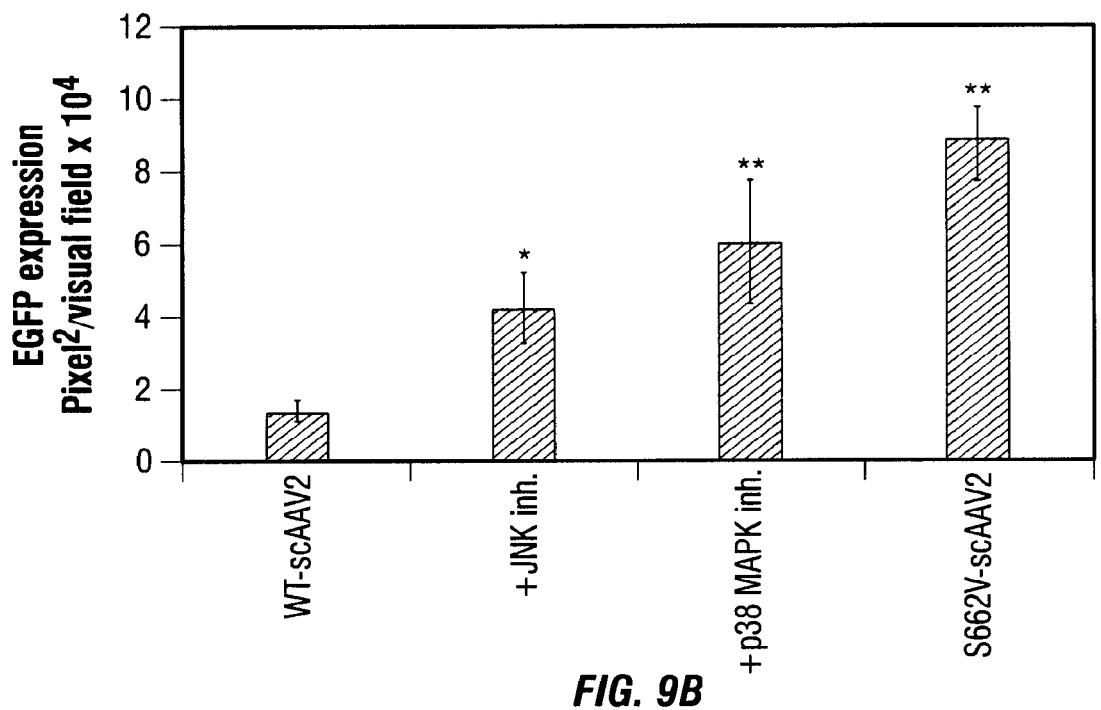
Figure 9C:
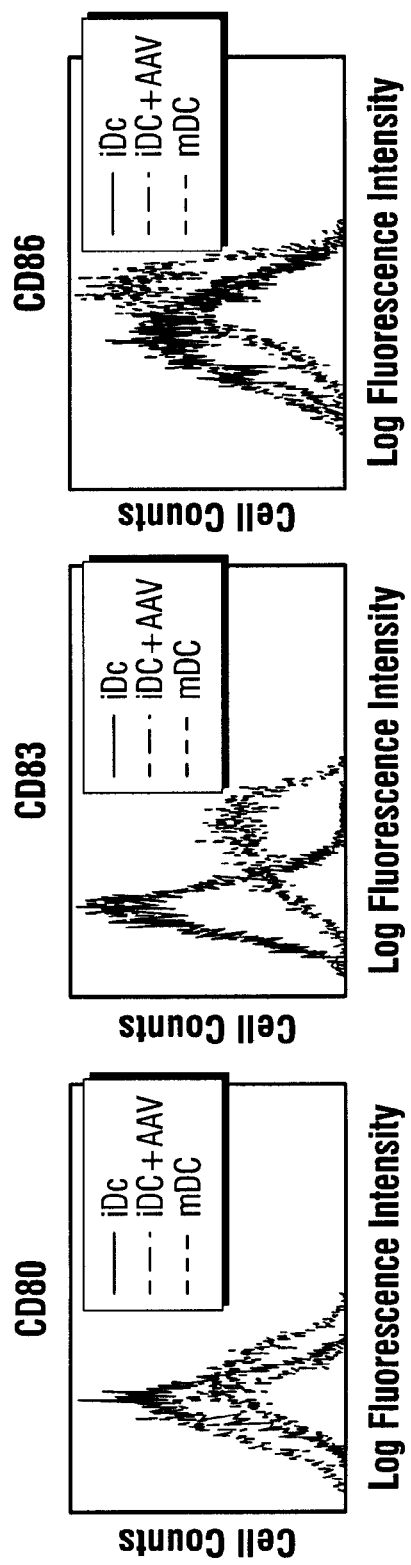

The results show that pre-treatment of moDCs with specific inhibitors of JNK and p38 MAPK increased EGFP expression levels ~2-fold and ~3-fold, respectively, and the transduction efficiency was enhanced by ~5-fold with the S662V mutant vectors (FIG. 9A, FIG. 9B, and FIG. 9C).

Since inhibition of these kinases has previously been reported to prevent maturation of dendritic cells, the capability of S662V mutant to induce phenotypic changes in DCs was also examined. Briefly, moDC were infected with increasingly higher MOI of up to 50,000 vgs per cell, harvested at 48 hrs p.i., and analyzed by fluorescence-activated cell sorting (FACS) for up regulation of surface co-stimulatory molecules. Flow cytometric analyses of DC maturation markers such as CD80, CD83 and CD86 indicated that, similar to WT AAV2 vectors, the S662V mutant vectors also did not induce the maturation of moDCs (FIG. 9C). The results showed that the capsid-mutated AAV vectors prepared in accordance with the present invention demonstrated low immunogenicity.

Example 6—Generation of hTERT-Specific CTL by moDC Transduced with AAV2-S662V Vectors As the serine-mutant AAV2 vector-mediated transgene expression in moDC was significantly improved compared with the WT-AAV2 vectors, this study demonstrates the ability of S662V-loaded moDCs to stimulate the generation of cytotoxic T-lymphocytes and effective specific killing of target cells. Given that human telomerase is recognized as a unique anti-cancer target commonly expressed in most cancer cells, a truncated human telomerase (hTERT) gene under the control of the chicken β-actin promoter was cloned and the DNA was packaged into the AAV2 S662V mutant. Non-adherent peripheral blood mononuclear cells (PBMC) containing up to 25% of CD8 positive cells were stimulated once with moDC/hTERT delivered by the S662V vector. An immortalized myelogenous leukemia cell line, K562, was used for a two-color fluorescence assay of cell-mediated cytotoxicity to generate a killing curve with subsequently reduced effector to target cell ratio.

Figure 10:
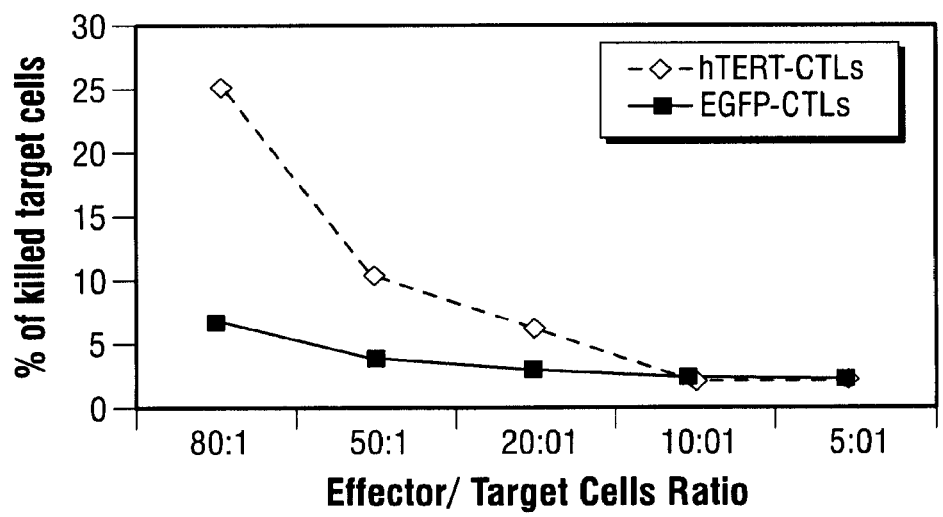
FIG. 10 illustrates an analysis of hTERT-specific cytotoxic T-lymphocytes (CTLs) killing activity on K562 cells. CTLs were generated after transduction of moDCs by AAV2-S662V vectors encoding the truncated human telomerase (hTERT). AAV2-S662V-EGFP vector-transduced moDCs were used to generate non-specific CTLs. Prestained with 3,3-dioctadecyloxacarbocyanine (DiOC18(3)), a green fluorescent membrane stain, $1 \times 10^5$ target K562 cells were co-cultured overnight with different ratios of CTLs (in this illustrative example 80:1, 50:1, 20:1, 10:1, and 5:1). Membrane-permeable nucleic acid counter-stain, propidium iodide, was added to label the cells with compromised plasma membranes. Percentages of killed, double stain-positive cells were analyzed by flow cytometry.
Figure 11B:
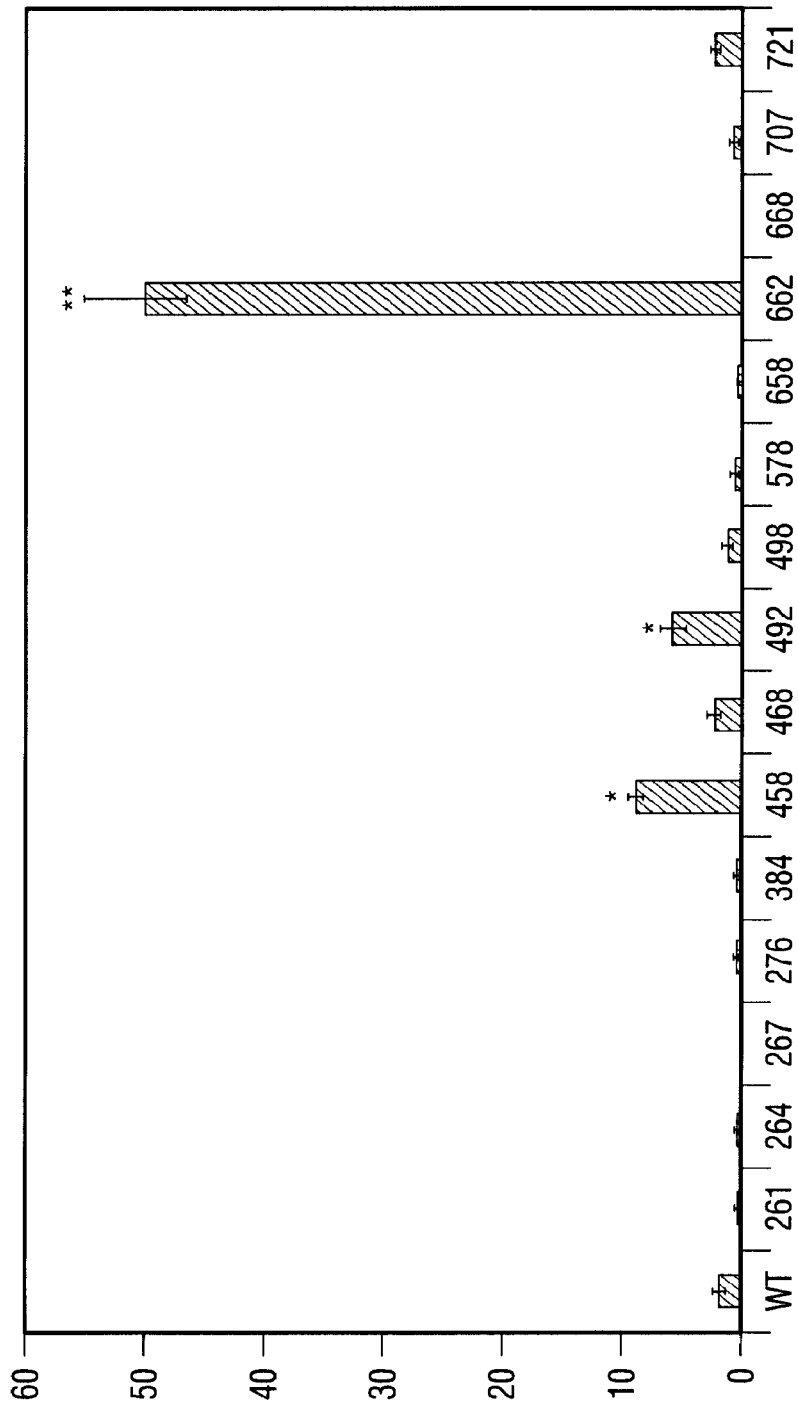
Figure 12B:
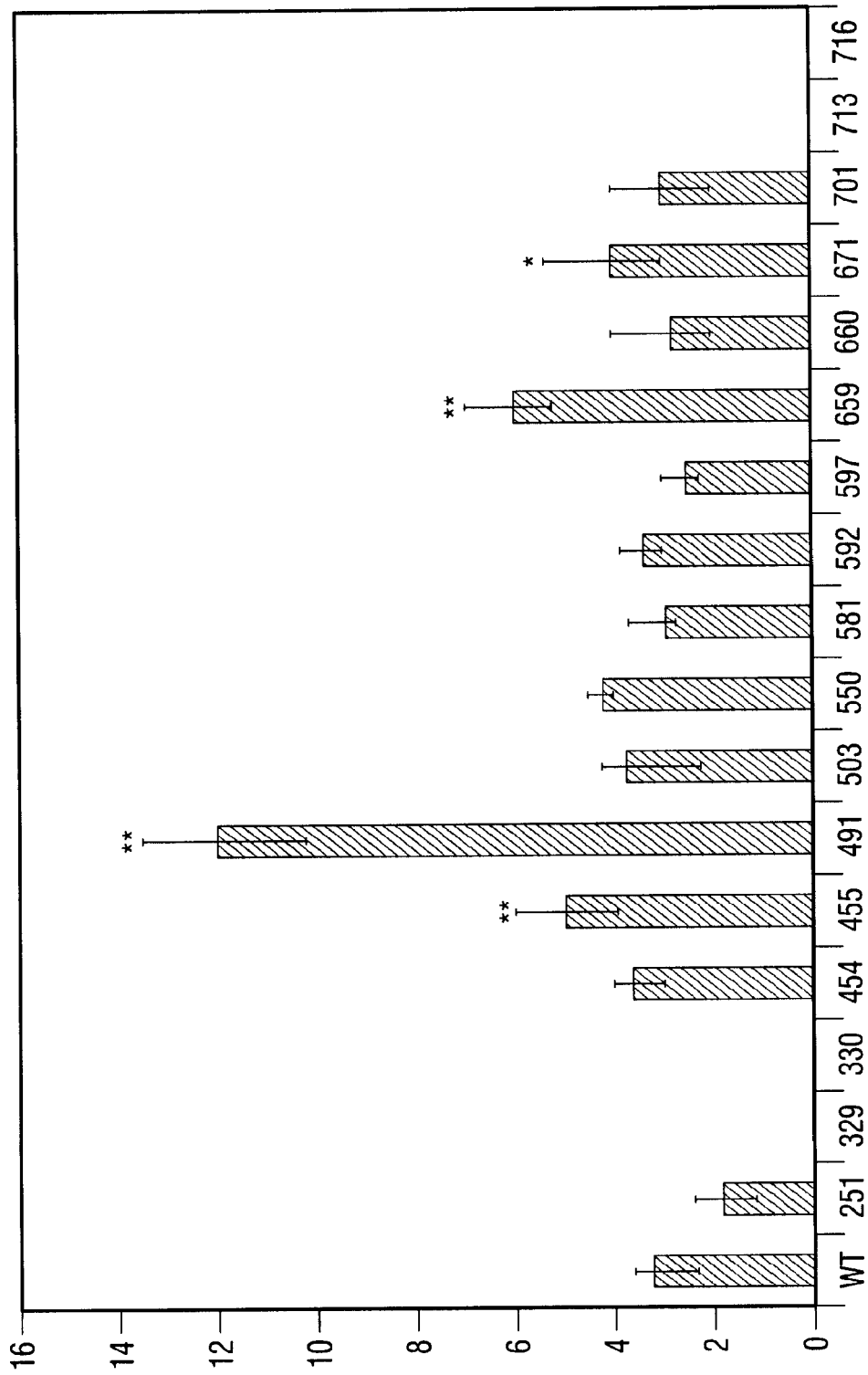

The results, shown in FIG. 10, indicated that moDC loaded with hTERT could effectively stimulate specific T cell clone proliferation and killing activity compared with moDC expressing GFP. These results also indicated that capsid-mutated rAAV-vector based delivery methods could also be used in a variety of mammalian vaccination methodologies.

Example 7—High-Efficiency rAAV2 Vectors Obtained by Site-Directed Mutagenesis of Surface-Exposed Tyrosine, Serine, and/or Threonine Residues AAV vectors are currently in use in a number of clinical trials as a delivery vehicle to target a variety of tissues to achieve sustained expression of therapeutic genes. However, large vector doses are needed to observe therapeutic benefits. Production of sufficient amounts of the vector also poses a challenge, as well as the risk of initiating an immune response to the vector. Thus, it is critical to develop novel AAV vectors with high transduction efficiency at lower doses.

The cellular epidermal growth factor receptor protein tyrosine kinase (EGFR-PTK) negatively impacts transgene expression from recombinant AAV2 vectors primarily due to phosphorylation of AAV2 capsids at tyrosine residues. Tyrosine-phosphorylated capsids are subsequently degraded by the host proteasome machinery, which negatively impacts the transduction efficiency of AAV vectors. Selective inhibitors of JNK and p38 MAPK serine/threonine kinases improve the transduction efficiency, indicating that phosphorylation of certain surface-exposed serine or/and threonine residues decreases the transduction efficiency of AAV vectors.

Site-directed mutagenesis to the capsid protein of the wild-type AAV2 was performed. As shown in FIG. 11A, FIG. 11B, FIG. 12A, and FIG. 12B, the serine (S662V) and threonine (T491V) mutants of the wild-type AAV2 capsid protein substantially increase the transduction efficiency of AAV vectors.

The serine (S662V) and threonine (T491V) mutations were combined with the best-performing single (Y730F) and triple (Y730F+500+444F) tyrosine-mutants to generate the following vectors: (i) three double (S662V+T491V; Y730F+ S662V; Y730F+T491V); (ii) one triple (S662V+Y730F+ T491V); (iii) two quadruple (Y730+500+444F+S662V; Y730+500+44F+T491V); and (iv) one quintuple (Y730+ 500+4440F+S662V+T491V). The transduction efficiency of each of the mutant vector was evaluated using a primary murine hepatocyte cell line H3.25.

Figure 13B:
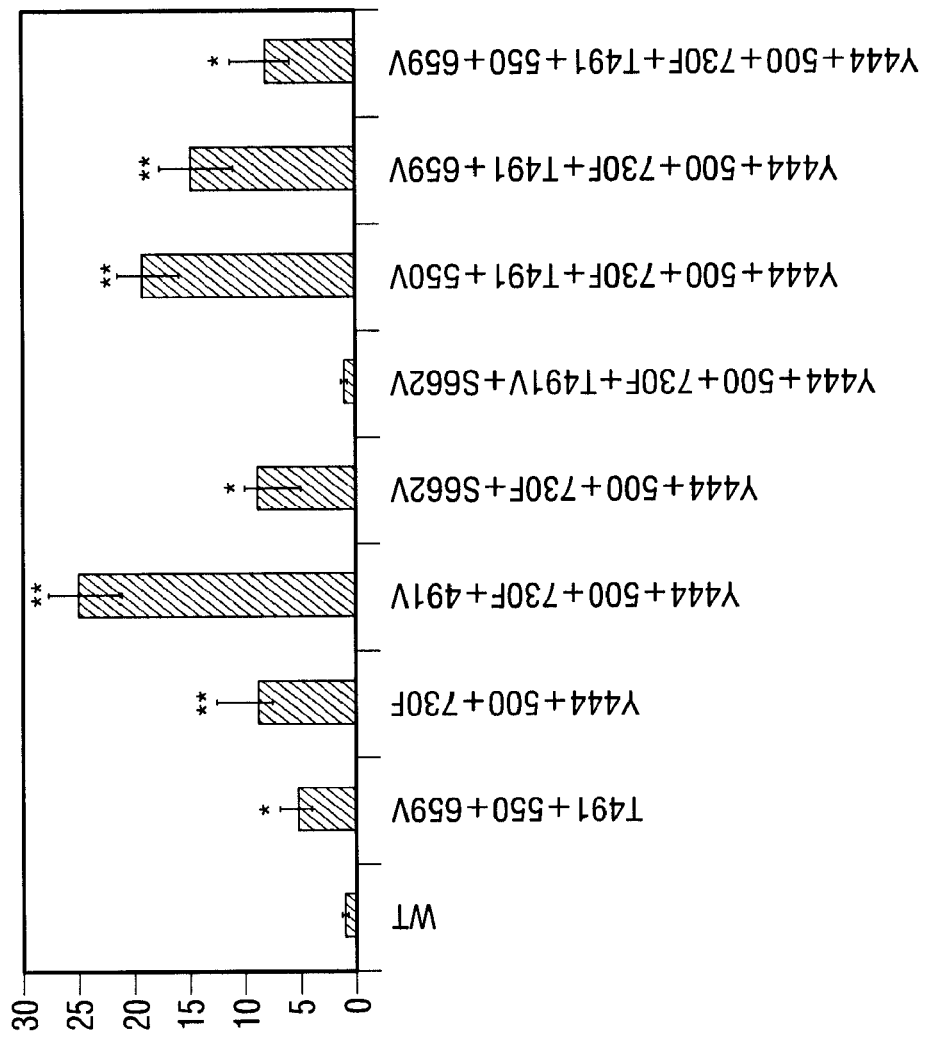

As shown in FIG. 13A and FIG. 13B, the AAV2 quadruple mutant (Y730+500+730F+T491V)-based vector increased the transduction efficiency by approximately 30-fold over that of the corresponding, unmodified wild-type (WT) AAV2 vector, and approximately 3-fold over that produced by the AAV2 triple mutant (Y730+500+444F)-based vector. Combining the S662V mutation with either the single (Y730F)- or the triple-tyrosine mutant (Y730F+500+444F) vector, negatively affected the transduction efficiency.

Genetically modified dendritic cells (DCs) have been extensively studied, and numerous Phase I and II clinical trials evaluating their efficacy in patients with cancer have been initiated. However, current methods for DC loading are inadequate in terms of cell viability, uncertainty regarding the longevity of antigen presentation, and the restriction by the patient's haplotype. Successful transduction of different subsets of DCs by different commonly used serotypes of AAV vectors has been demonstrated and the potential advantage of an AAV-based antitumor vaccine discussed. However, further improvements in gene transfer by recombinant AAV vectors to DCs in terms of specificity and transduction efficiency are warranted to achieve a significant impact when used as an anti-tumor vaccine.

Serine/threonine protein kinases can negatively regulate the efficiency of recombinant AAV vector-mediated transgene expression by phosphorylating the surface-exposed serine and/or threonine residues on the viral capsid and target the vectors for proteasome-mediated degradation. Prevention of phosphorylation of the surface-exposed serine and threonine residues could allow the vectors to evade phosphorylation and subsequent ubiquitination and, thus, prevent proteasomal degradation.

Site-directed mutagenesis was performed to the wild-type AAV vector of each of the 15 surface-exposed serine (S) residues. The results show that substitution of S662 to valine (V) increased the transduction efficiency of the S662V mutant up to 6-fold, when compared to the wild-type AAV2 vector. In addition, site-directed mutagenesis was performed to substitute each of the 17 surface-exposed threonine (T) residues of the wild-type AAV2 vector with V (T251V, T329V, T330V, T454V, T455V, T503V, T550V, T592V, T581V, T597V, T491V, T671V, T659V, T660V, T701V, T713V, T716V). The transduction efficiency of each of the T-V mutant vectors was evaluated using primary human monocyte-derived dendritic cells (moDCs) at an MOI of 2,000 vgs/cell. Following maturation with a cytokine mixture including 10 ng/ml, TNF-α, 10 ng/mL IL-1, 10 ng/mL IL-6, and 1 mg/mL PGE2, EGFP expression was analyzed 48-hrs' post-infection under a fluorescent microscope. Cells were characterized for expression of co-stimulatory molecules (CD80, CD83, and CD86) to ensure that they met the typical phenotype of mature dendritic cells (mDCs).

Figure 14A:
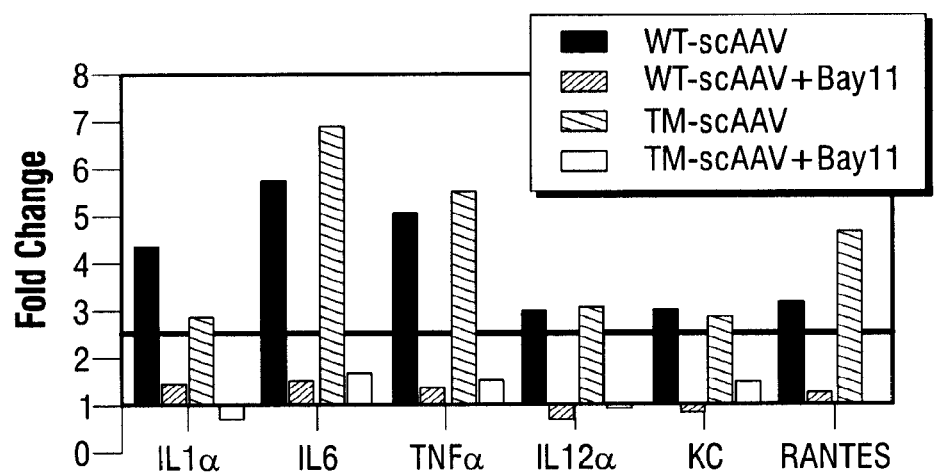
FIG. 14A, FIG. 14B, FIG. 14C, FIG. 14D, and FIG. 14E demonstrate AAV vector-induced innate immune response in mice in vivo.
Figure 14B:
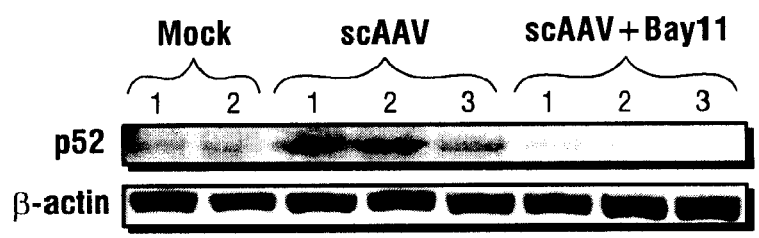

As shown in FIG. 14A and FIG. 14B, mutations of the following T residues (T455V, T491V, T550V, T659V, T671V) increased the transduction efficiency of moDCs up to 5-fold, with the T491V mutant demonstrating the highest transduction efficiency among those tested in this study.

To examine whether multiple mutations of T residues could further enhance the transduction efficiency, the following AAV2 mutants were also generated: (i) four AAV2 vectors with double mutations with respect to the wild-type AAV2 vector (T455V+T491V; T550V+T491V; T659V+T491V; T671V+T491V); (ii) two triple-mutated AAV2 vectors (T455V+T491V+T550V and T550V+T659V+T491V); and (iii) one quadruple mutated AAV2 vector (T455V+T550V+T659V+T491V). The results demonstrated that several of these multiple-mutant vectors increased the transduction efficiency of dendritic cells, and the triple-mutant (T550V+T659V+T491V) in particular was shown to possess optimal transduction efficiency (approximately ten-fold greater than that of the corresponding unmodified, wild-type AAV2 vector!) These results were further enhanced by making various combinatorial mutants in "mix-and-match" fashion to generate a number of suitable capsid-mutated vectors/One such combination—combining the best performing serine substitution (S662V) mutant with the best-performing threonine substitution (T491V) further enhanced the transduction efficiency by approximately 8-fold as compared to either of the individual single mutations.

Example 8—Targeted Mutagenesis of Ubiquitin-Binding Lysine Residues on the AAV2 Capsid Improves its Transduction Efficiency It is now well recognized that hepatic gene transfer of high doses of AAV vectors predispose to a robust adaptive immune response, from the data available from hemophilia clinical trials. Thus, there is a need to develop novel strategies which will allow lower doses of vectors to be used to achieve sustained phenotypic correction and limit vector related immune-toxicities.

This Example shows that surface-exposed lysine residues of the VP3 region of the VVA2 capsid protein are direct targets for host ubiquitin ligases, and mutagenesis of these lysine residues improves transduction efficiency of the AAV vectors.

In silico analysis using a ubiquitination prediction software (UbPred) identified seven lysine residues (K39, K137, K143, K161, K490, K527 and K532) of the wild-type AAV2 capsid could be ubiquitinated. Lysine to Arginine mutations in AAV2 Rep/Cap coding plasmid was carried out and highly purified stocks of a recombinant self-complementary AAV2 vectors expressing EGFP [scAAV-CBa-EGFP] were generated in each of the seven lysine mutant plasmids. The physical particle titres of lysine mutant vectors was comparable to wild-type (WT) scAAV vectors (~0.5-1×10$^{12}$ vgs/mL), suggesting that these mutations did not affect the structure or packaging ability of mutant capsids.

scAAV vectors containing WT or each of the seven lysine mutant capsids were then evaluated for their transduction potential in vitro. Approximately 8×10$^4$ HeLa or HEK293 cells were mock-infected or infected with AAV at different multiplicities of infection (MOI) including 500, 2000 or 5000 vgs/cell. Forty-eight hours post-infection, transgene (EGFP) expression was measured by fluorescence microscopy and by flow-cytometry.

The results presented in FIG. 15) demonstrated that the K532R mutant vector significantly increased gene expression in both HeLa (18X) and HEK 293 (9X) cells in vitro, when compared to the WT-AAV2 vector. The increased transduction efficacy of the K532R vector was consistent across three different MOIs tested, with an average increase of 10-fold over the WT vector.

Example 9—AAV Vector-Mediated Activation of Canonical and Alternative NF-KB Pathways In Vivo Infection of HeLa cells with adeno-associated viral (AAV) vectors in vitro results in activation of the alternative pathway of NF-KB, a central regulator of cellular immune and inflammatory responses. In addition, activation of the alternative, but not the canonical pathway, regulates AAV-mediated transgene expression in these cells.

This example defines a role for NF-KB in liver-directed AAV-mediated gene transfer in mice. In vivo, AAV-mediated gene transfer results in consecutive activation of the canonical and the alternative NF-KB pathways. These pathways are thought to drive primarily inflammation (canonical) or adaptive responses (alternative pathway). AAV2 vectors with the wild-type (WT) or the tyrosine triple-mutant (TM) capsids activated the canonical NF-KB pathway within 2 hrs, resulting in expression of pro-inflammatory cytokines and chemokines (FIG. 14A). This transient process is Toll-like receptor 9 (TLR9)-dependent and likely reflects the initial sensing of the vector genome by antigen-presenting cells. Western blot analyses (FIG. 14B) of liver homogenates prepared 9 hrs post-vector delivery, showed abundance of the nuclear p52 protein component of the alternative NF-KB pathway, likely resulting from gene transfer to hepatocytes.

Figure 14C:
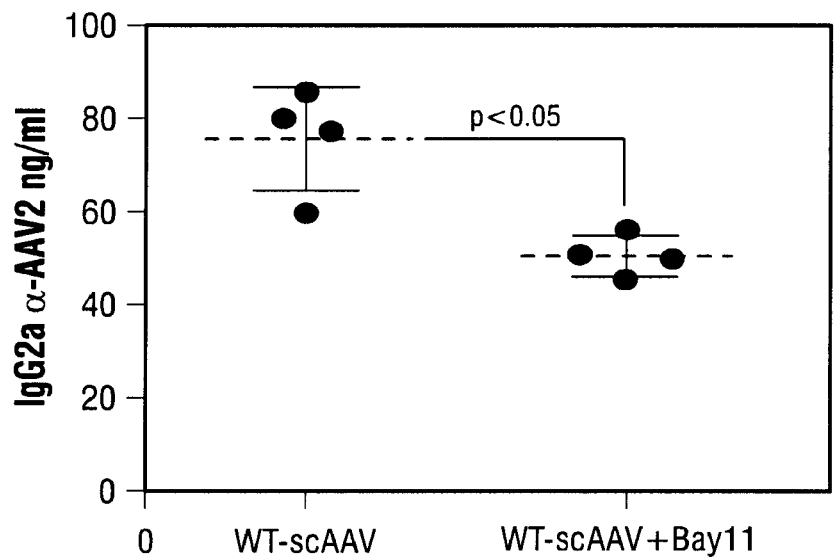
Figure 14D:
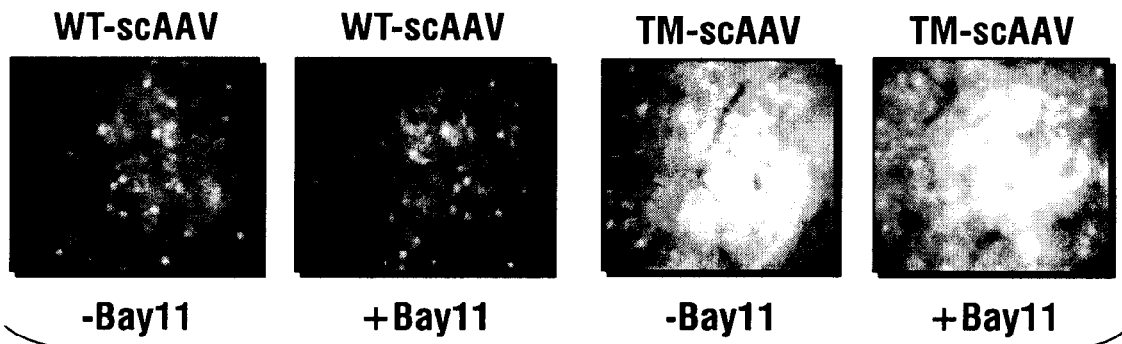
Figure 14E:
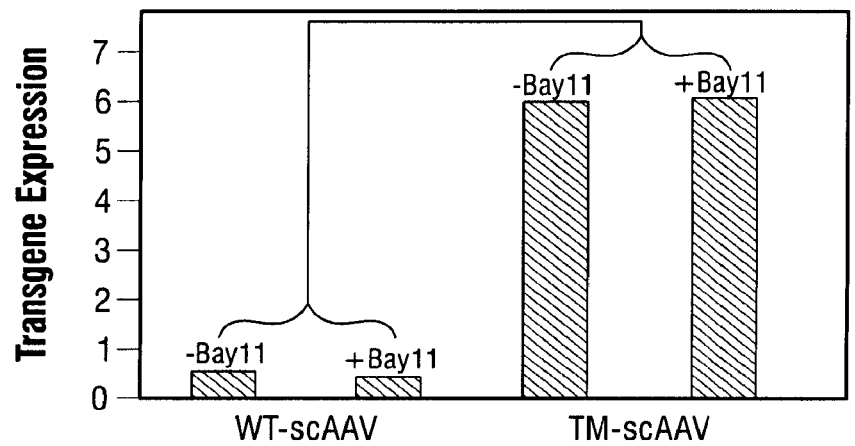

Administration of the NF-KB inhibitor Bay11 prior to gene transfer effectively blocked activation of both pathways. This prevented pro-inflammatory innate immune responses and also dampened anti-AAV capsid antibody formation (FIG. 14C). Importantly, Bay11 did not interfere with long-term transgene expression mediated by both the WT and the TM AAV2 vectors (FIG. 14D). These results demonstrated that transient immuno-suppression with NF-KB inhibitor prior to vector administration eliminated inflammation (caused by innate responses), and also limited adaptive responses.

Example 10—Development of Optimized rAAV3 Vectors: Mechanism of High-Efficiency Transduction of Human Liver Cancer Cells Of the 10 commonly used AAV serotypes, AAV3 has been reported to transduce cells and tissues poorly. However, the present inventors discovered that AAV3 vectors transduce established human hepatoblastoma (HB) and human hepatocellular carcinoma (HCC) cell lines as well as primary human hepatocytes extremely efficiently. AAV3 utilizes human HGFR as a cellular receptor/co-receptor for viral entry.

Figure 15A:
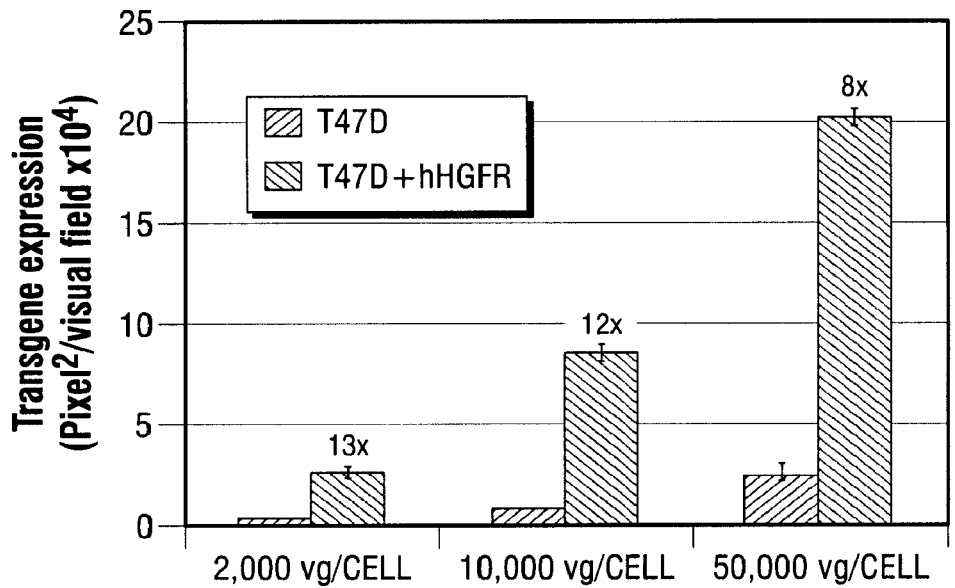
FIG. 15A, FIG. 15B, FIG. 15C, and FIG. 15D illustrate AAV3-mediated transgene expression in T47D and T47D+hHGFR cells.
Figure 15B:
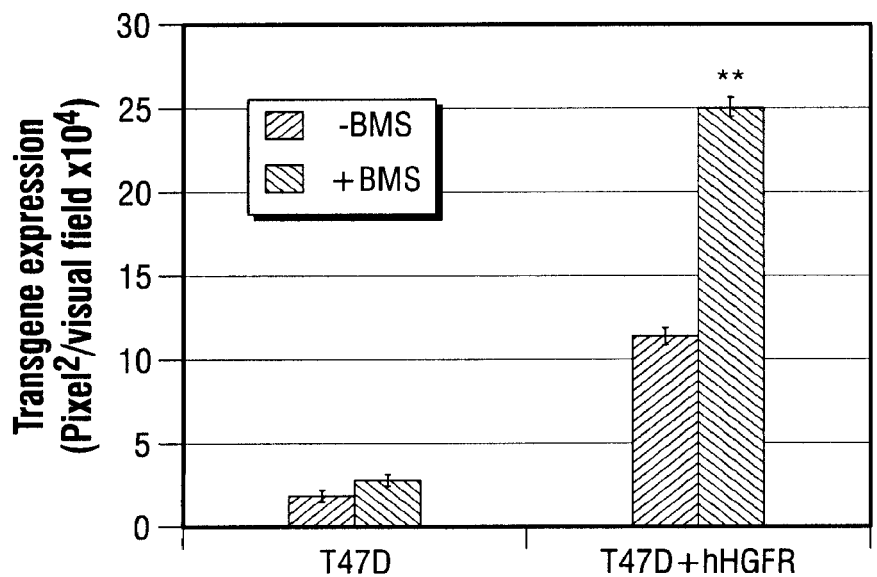
Figure 15C:
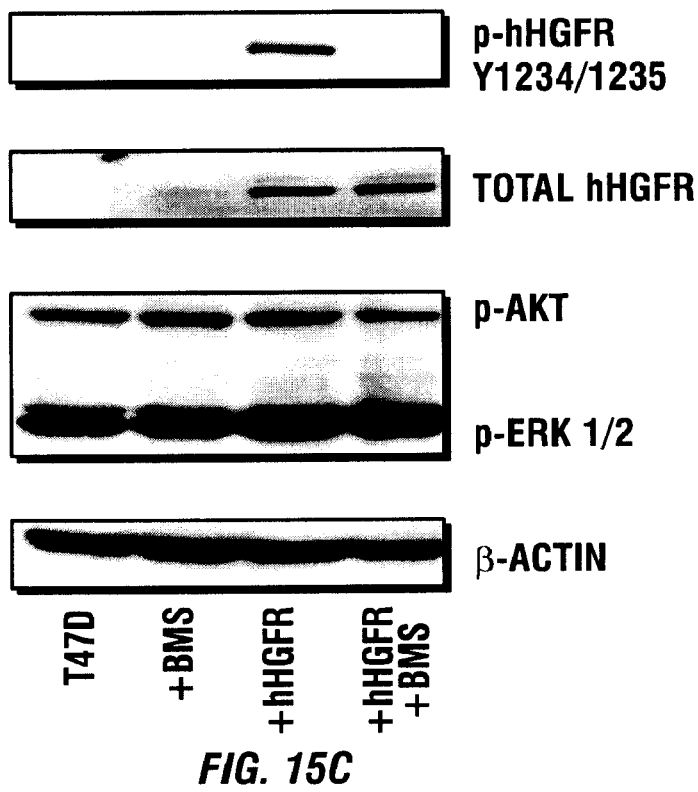
Figure 15D:
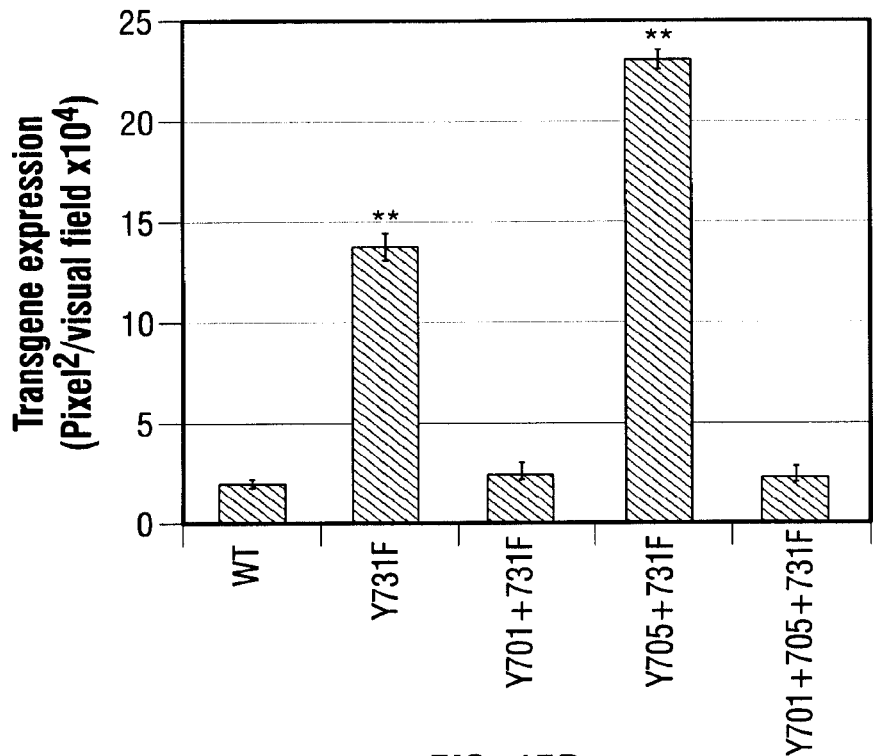

This Example shows that both extracellular as well as intracellular kinase domains of hHGFR are involved in AAV3 vector entry and AAV3-mediated transgene expression. The results show that (i) AAV3 vector-mediated transduction is significantly increased in T47D cells, a human breast cancer cell line that expresses undetectable levels of the endogenous hHGFR, following stable transfection and over-expression of hHGFR (FIG. 15A); (ii) the tyrosine kinase activity associated with hHGFR negatively affects the transduction efficiency of AAV3 vectors (FIG. 15B, FIG. 15C); (iii) the use of proteasome inhibitors significantly improves AAV3 vector-mediated transduction; (iv) site-directed mutagenesis of specific surface-exposed tyrosine residues on the AAV3 capsid leads to improved transduction efficiency; and (v) a specific combination of two tyrosine-mutations further improves the extent of transgene expression (FIG. 15D). These AAV3 vectors can be useful for the gene therapy of liver cancer in humans.

Example 11—Site-Directed Mutagenesis of Surface-Exposed Lysine Residues Leads to Improved Transduction by rAAV2 and rAAV8 Vectors in Murine Hepatocytes In Vivo The ubiquitin-proteasome pathway plays a critical role in the intracellular trafficking of recombinant AAV2 vectors, which negatively impacts the transduction efficiency of these vectors. The primary signal for ubiquitination is phosphorylation of specific surface-exposed tyrosine (Y), serine (S), and threonine (T) residues on the AAV2 capsids; the removal of some of these residues significantly increases the transduction efficiency of the wild-type (WT) AAV2 vectors.

This Example illustrates that site-directed mutagenesis of surface-exposed lysine residues prevented ubiquitination of AAV2 capsids, which in turn, prevented vector degradation by cellular proteasomal machinery, thereby producing improved vectors for delivering therapeutic or diagnostic polynucleotides to selected mammalian cells.

Figure 16:
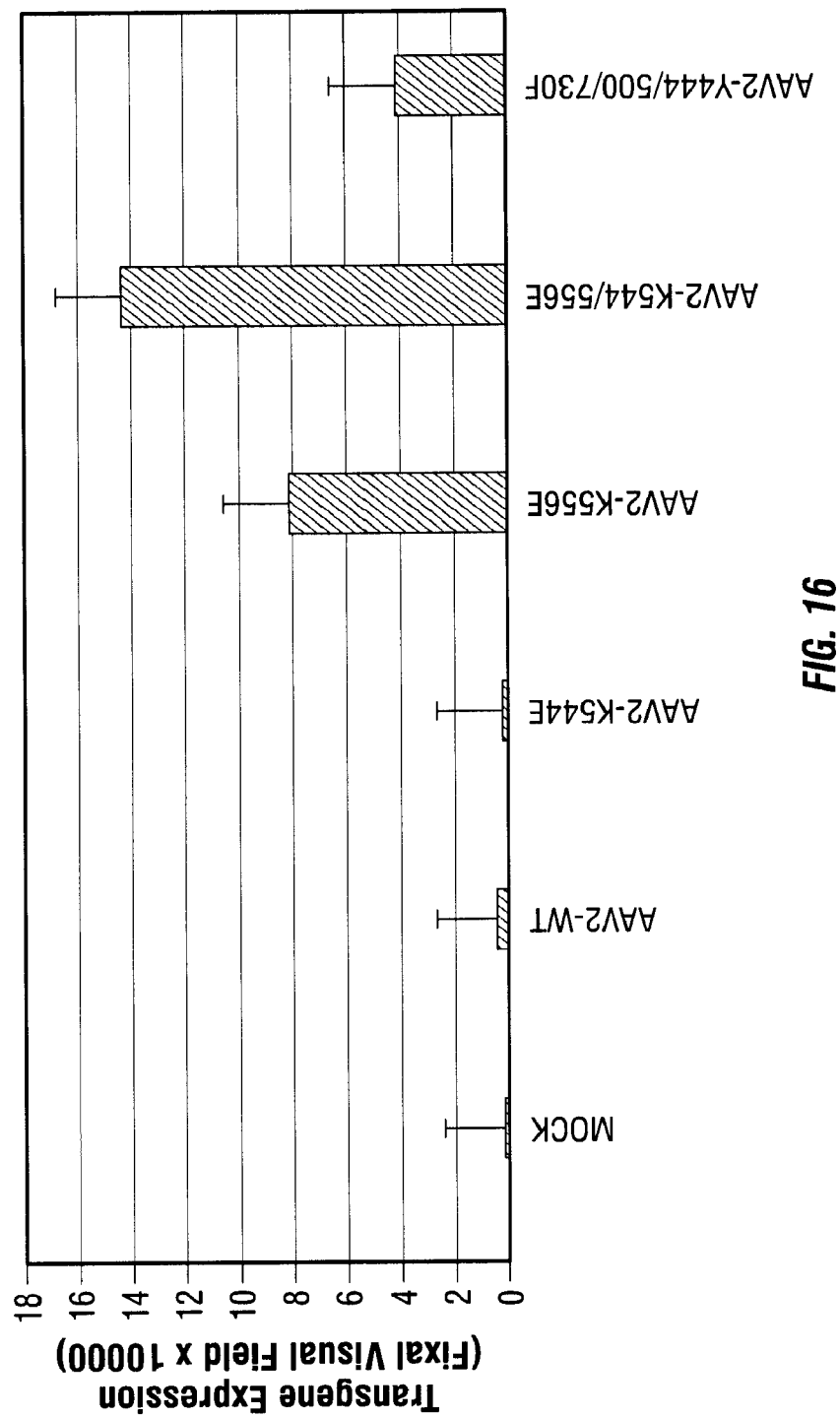
FIG. 16 shows the quantification of transgene expression by AAV2-K544F, AAV2-K556E, AAV2-K544/566E, and AAV2-Y444/500/730F.
Figure 17A:
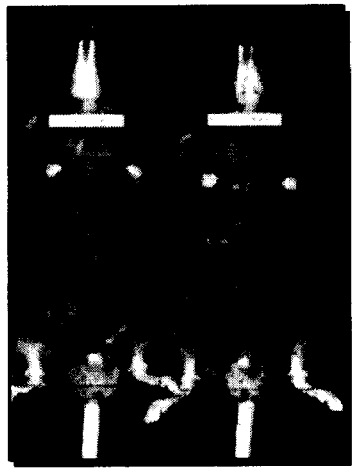
FIG. 17A, FIG. 17B, FIG. 17C, FIG. 17D and FIG. 17E illustrate the transduction efficiency of WT- and lysine-mutant scAAV8 vectors in primary hepatocytes in vivo (C57BL/6 mice; $1\times10^{10}$ scAAV-2-CBAp-Fluc vectors; tail-vein injections; 2-weeks) (experiment 2)
Figure 17B:
Figure 17C:
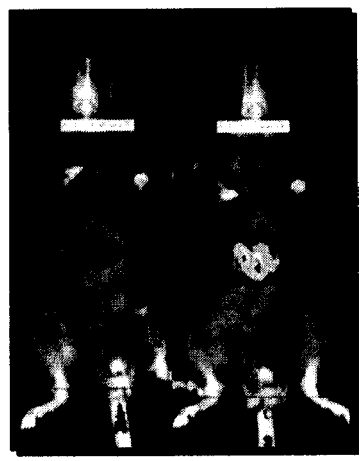
Figure 17D:
Figure 17E:
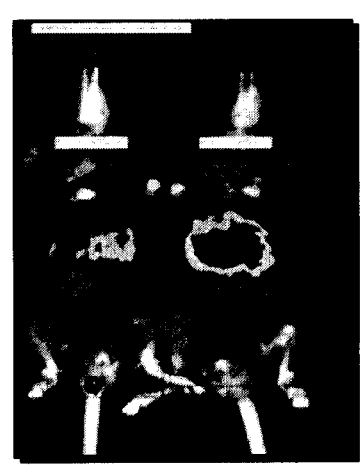
Figure 18:
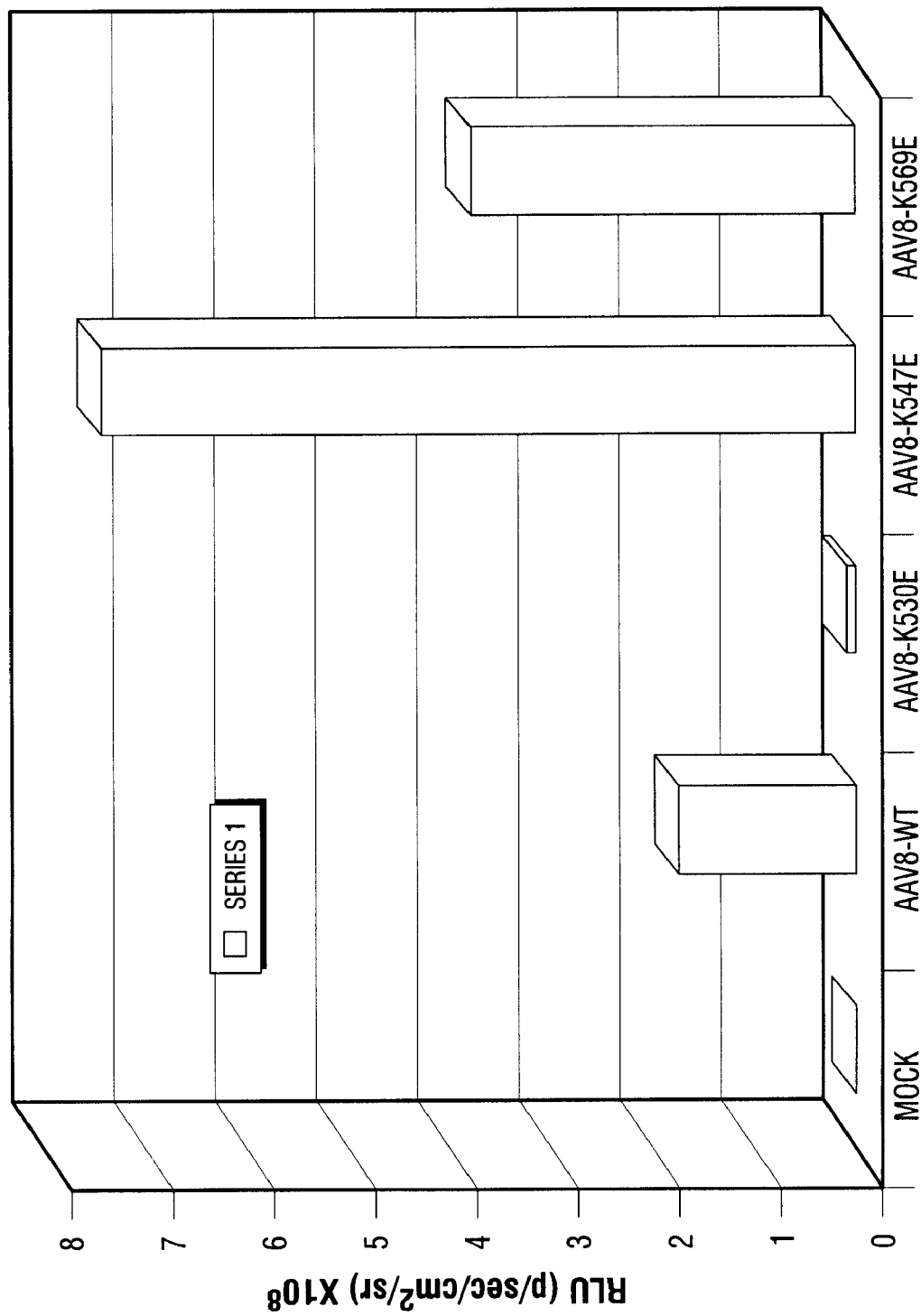
FIG. 18 demonstrates the quantification of transgene expression by AAV8-K530E, AAV8-K547E, and AAV8-K569E in accordance with one aspect of the present invention.
Figure 19B:
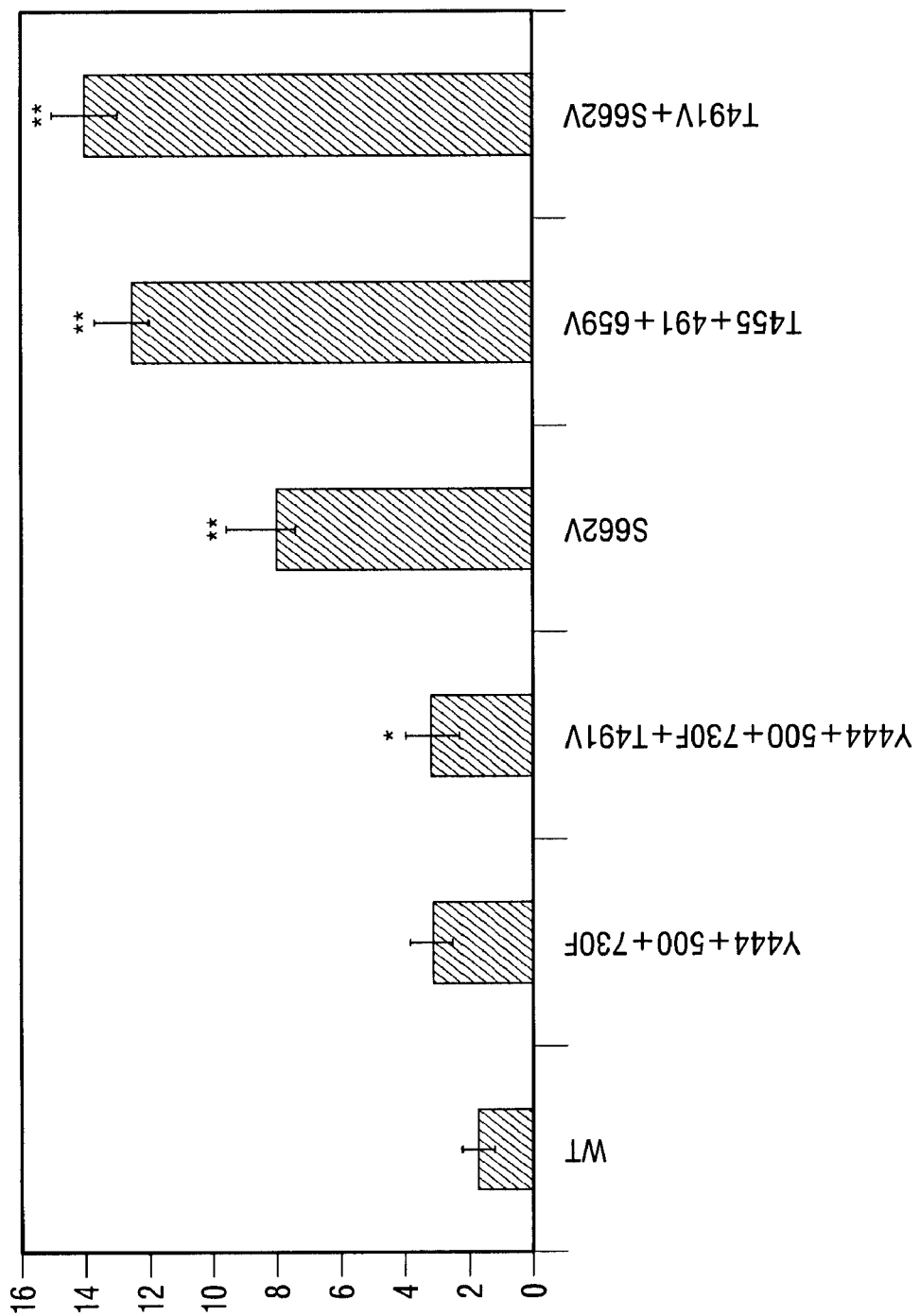
Figure 20A:
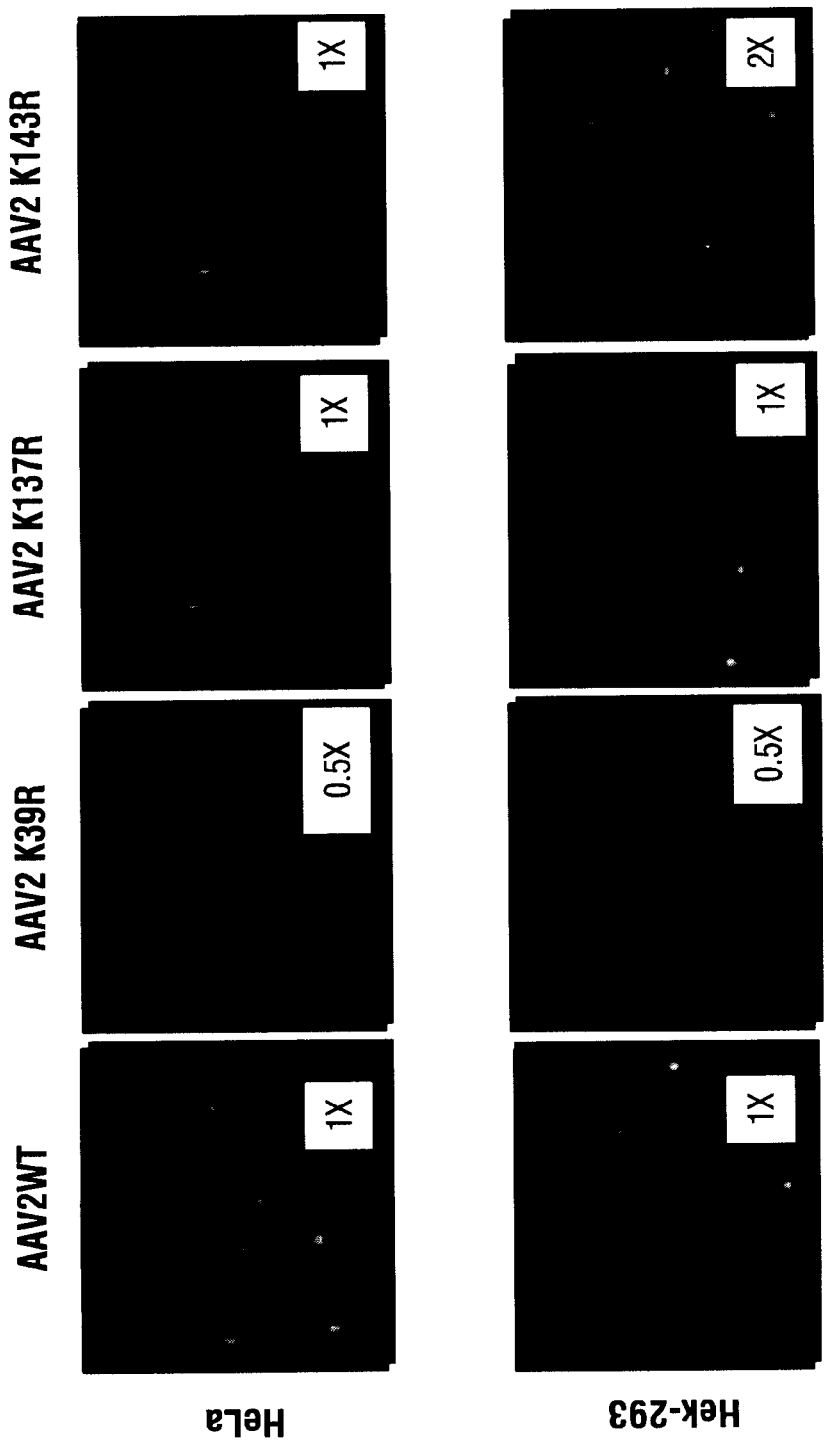
FIG. 20A and FIG. 20B show the transduction efficiency of WT- and exemplary lysine- or tyrosine-substituted mutant scAAV2 vectors in accordance with one aspect of the present invention in a study involving primary hepatocytes in vivo (C57BL/6 mice; $1\times10^{10}$ scAAV-2-CBAp-Fluc vectors; tail-vein injections; 2-weeks)
Figure 20B:
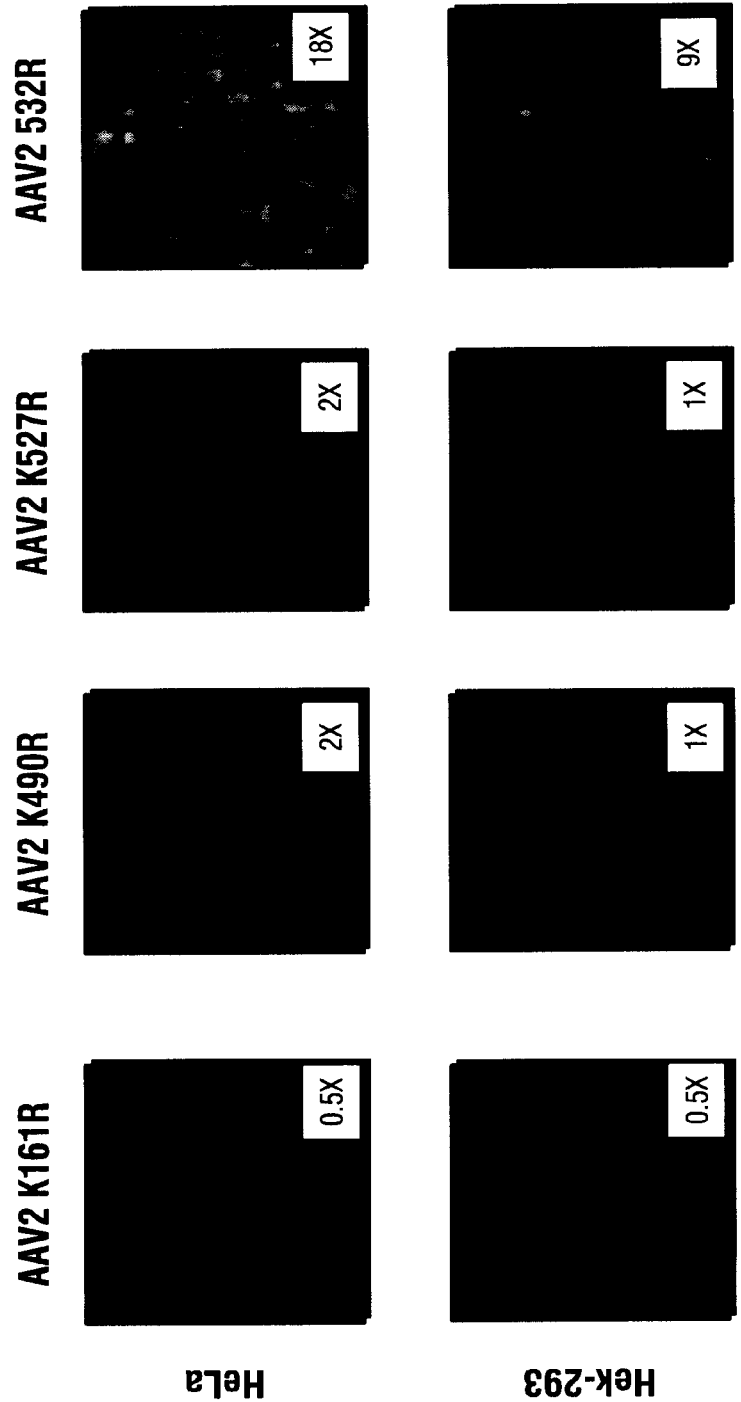
Figure 23A:
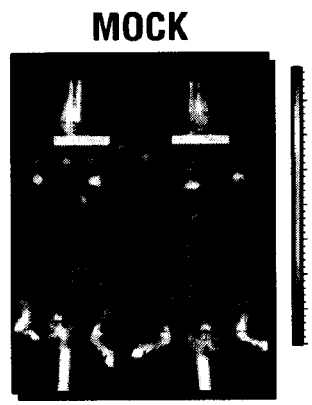
FIG. 23A, FIG. 23B, FIG. 23C, FIG. 23D, FIG. 23E, and FIG. 23F show transduction efficiency of exemplary AAV2 lysine mutants prepared in accordance with the methods disclosed herein in HeLa and HEK293 cells in vitro (MOI 2000). The relative fold-increase in gene expression is shown as inserts.
Figure 23B:
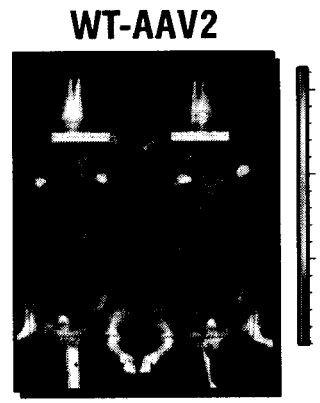
Figure 23C:
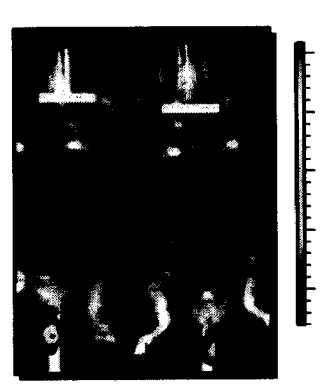
Figure 23D:
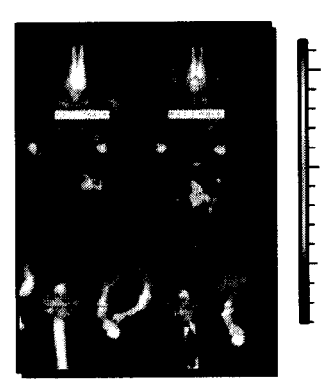
Figure 23E:
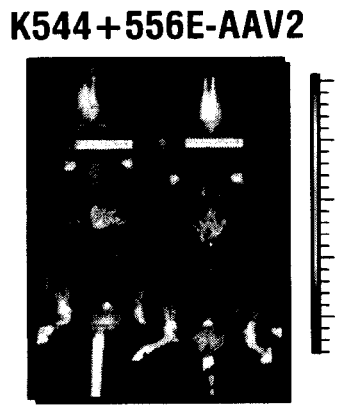
Figure 23F:
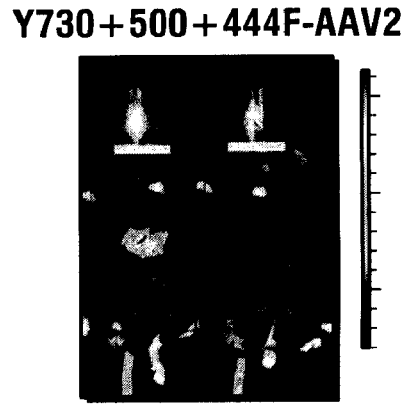
Figure 24:
FIG. 24 shows the transduction efficiency of WT- and exemplary lysine-mutated capsid-expressing scAAV8 vectors in murine hepatocytes in vivo (C57BL/6 mice; $1\times10^{10}$ scAAV-2-CBAp-Fluc vectors; tail-vein injections; 2-weeks) (experiment 1)
Figure 25:
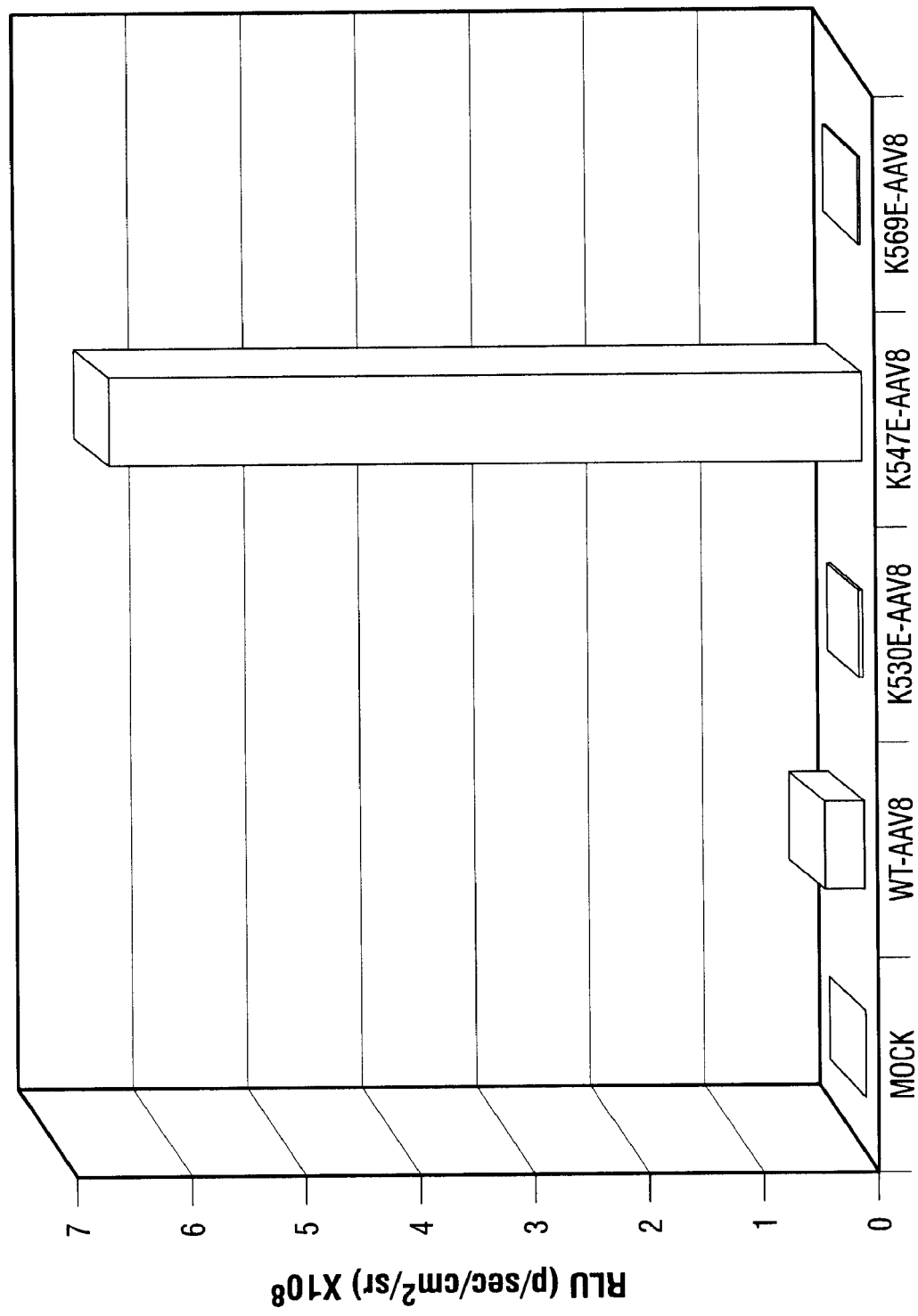
FIG. 25 shows the quantification of transgene expression by exemplary AAV8 vectors expressing particular lysine-substituted capsid protein mutants. Shown are the representative constructs AAV8-K530E, AAV8-K547E, and AAV8-K569E.

AAV2 vectors with a single mutation in the surface-exposed lysine (K) residues (K258, K490, K527, K532, K544, 549, and K556) with glutamic acid (E) were prepared and analyzed. The transduction efficiency of K490E, K544E, K549E, and K556E scAAV2 vectors expressing the EGFP reporter gene increased as much as 5-fold, when compared with the corresponding unmodified WT AAV2 vectors (see FIG. 16). Of the exemplary constructs analyzed in this study, the K556E single mutant had the highest transduction efficiency (with a transduction rate of 2,000 vgs/cell in vitro in Hela cells) among the lysine-substituted mutants. Similar results were also obtained when $1 \times 10^{10}$ vgs of each vector was delivered intravenously to C57BL/6 mice in vivo, and the transgene expression in hepatocytes evaluated at 2-weeks' post-injection. Bioluminescence imaging two weeks post injection following intravenous delivery of $1 \times 10^{10}$ vgs/animal of either the WT or the lysine-mutated ssAAV2 vectors expressing the firefly luciferase (Fluc) reporter gene further corroborated these results.

Importantly, two of the most efficient single amino acid residue mutations were combined to generate a double-mutant (K544E+K556E). The transduction efficiency of this double-mutant ssAAV2-Fluc vector in murine hepatocytes in vivo increased by ~2-fold compared to either of the single mutants, and ~10-fold as compared to the WT, unmodified ssAAV2 control vector.

AAV8 vectors have previously been shown to transduce murine hepatocytes exceedingly well. As some of the surface-exposed K residues are also conserved in this serotype, ssAAV8-Fluc vectors with K530E-, K547E-, or K569E-mutant were also generated. The transduction efficiency of K547E and K569E ssAAV8-Fluc vectors in murine hepatocytes in vivo increased by ~3-fold and ~2-fold, respectively, when compared with WT ssAAV9 vectors (FIG. 17A, FIG. 17B, FIG. 17C, FIG. 17D, FIG. 17E, and FIG. 18).

The results (summarized herein in FIG. 19A, FIG. 19B, FIG. 20A and FIG. 20B, FIG. 21A-FIG. 21I, FIG. 22A-FIG. 22I, FIG. 23A-FIG. 23F, FIG. 24, and FIG. 25) demonstrated that targeting the surface-exposed lysine residues could also be exploited to create new, improved AAV-based viral vectors for increased transduction of human cells, and, importantly, new targeting vectors useful in gene therapy.

REFERENCES

The following references, to the extent that they provide exemplary procedural or other details supplementary to those set forth herein, are specifically incorporated herein by reference:

Aldrich, W A et al., "Enhanced transduction of mouse bone marrow-derived dendritic cells by repetitive infection with self-complementary adeno-associated virus 6 combined with immunostimulatory ligands," *Gene Ther.*, 13:29-39 (2006).

Aslanidi, G el al., "Ectopic expression of Wnt10b decreases adiposity and improves glucose homeostasis in obese rats,' *Am. J. Physiol.—Endocrinol. Metab.*, 293:E726-E736 (2007).

Aslanidi, G et al., "An inducible system for highly efficient production of recombinant adeno-associated virus (rAAV) vectors in insect Sf9 cells," *Proc. Nat'l. Acad. Sci. USA*, 106:5059-5064 (2009).

Banchereau, J and Steinman, R M, "Dendritic cells and the control of immunity," *Nature*, 392:245-252 (1998).

Beatty, G L and Vonderheide, R H "Telomerase as a universal tumor antigen for cancer vaccines," *Exp. Rev. Vaccines*, 7:881-887 (2008).

Boisleve, F et al., "Implication of the MAPK pathways in the maturation of human dendritic cells induced by nickel and TNF-alpha," *Toxicology*, 206:233-244 (2005).

Chapuis, F et al., "Differentiation of human dendritic cells from monocytes in vitro, *Eur. J. Immunol.*, 27:431-441 (1997).

Cheng, B et al., "Development of optimized AAV3 serotype vectors: mechanism of high-efficiency transduction of human liver cancer cells," *Gene Ther.*, 19(4):375-84 (2012).

Daya, S and Berns, K I, "Gene therapy using adeno-associated virus vectors," *Clin. Microbiol. Rev.*, 21:583-593 (2008).

den Brok, M H et al., "Dendritic cells: tools and targets for antitumor vaccination," *Exp. Rev. Vaccines*, 4:699-710 (2005).

DiPrimio, N et al., "Surface loop dynamics in adeno-associated virus capsid assembly," *J. Virol.*, 82:5178-5189 (2008).

Eisold, S et al., "Induction of an antitumoral immune response by wild-type adeno-associated virus type 2 in an in vivo model of pancreatic carcinoma," *Pancreas*, 35:63-72 (2007).

Figdor, C O et al., "Dendritic cell immunotherapy: mapping the way," *Nat. Med.*, 10:475-480 (2004).

Gao, G et al., "Adeno-associated viruses undergo substantial evolution in primates during natural infections," *Proc. Nat'l. Acad. Sci. USA*, 100:6081-6086 (2003).

Girod, A et al., "Genetic capsid modifications allow efficient re-targeting of adeno-associated virus type 2," *Nat. Med.*, 5:1438 (1999).

Harley, C B, "Telomerase and cancer therapeutics," *Nat. Rev.*, 8:167-179 (2008).

Heiser, A et al., "Autologous dendritic cells transfected with prostate-specific antigen RNA stimulate CTL responses against metastatic prostate tumors," *J. Clin. Investig.*, 109:409-417 (2002).

Jayandharan, G R et al., "Activation of the NF-kB pathway by adeno-associated virus (AAV) vectors and its implications in immune response and gene therapy," *Proc. Nat'l. Acad. Sci. USA*, 108:3743-3748 (2011).

Levy, H C et al., "Heparin binding induces conformational changes in Adeno-associated virus serotype 2," *J. Struct. Biol.*, 165:146-156 (2009).

Liu, M A, "Immunologic basis of vaccine vectors," *Immunity*, 33:504-515 (2010).

Mah, C et al., "Adeno-associated virus type 2-mediated gene transfer: role of epidermal growth factor receptor protein tyrosine kinase in transgene expression," *J. Virol.*, 72:9835-9843 (1998).

Mahadevan, M et al., "Generation of robust cytotoxic T lymphocytes against prostate specific antigen by transduction of dendritic cells using protein and recombinant adeno-associated virus," *Cancer Immunol. Immunother.*, 56:1615-1624 (2007).

Markusic, D M et al., "High-efficiency transduction and correction of murine hemophilia B using AAV2 vectors devoid of multiple surface-exposed tyrosines," *Mol. Ther.*, 18:2048-2056 (2011).

Mattis, A E et al., "Analyzing cytotoxic T lymphocyte activity: a simple and reliable flow cytometry-based assay," *J. Immunol. Methods*, 204:135-142 (1997).

Mueller, C and Flotte, T R, "Clinical gene therapy using recombinant adeno-associated virus vectors," *Gene Ther.*, 15:858-863 (2008).

Nakahara, T et al., "Differential role of MAPK signaling in human dendritic cell maturation and Th1/Th2 engagement," *J. Dermatol. Sci.*, 42:1-11 (2006).

Nakahara, T et al., "Role of c-Jun N-terminal kinase on lipopolysaccharide induced maturation of human monocyte-derived dendritic cells," *Int. Immunol.*, 16:1701-1709 (2004).

O'Neill, D W and Bhardwaj, N "Exploiting dendritic cells for active immunotherapy of cancer and chronic infections," *Molec. Biotechnol.*, 36:131-141 (2007).

Palucka, K et al., "Recent developments in cancer vaccines," *J. Immunol.*, 186:1325-1331 (2011).

Petrs-Silva, H el al., "High-efficiency transduction of the mouse retina by tyrosine-mutant AAV serotype vectors," *Mol. Ther.*, 17:463-471 (2009).

Ponnazhagan, S et al., "Adeno-associated virus type 2-mediated transduction of human monocyte-derived dendritic cells: implications for ex vivo immunotherapy," *J. Virol.*, 75:9493-9501 (2001).

Robert-Guroff, M, "Replicating and non-replicating viral vectors for vaccine development," *Curr. Opin. Biotechnol.*, 18:546-556 (2007).

Shin, O et al., "Effective transduction by self-complementary adeno-associated viruses of human dendritic cells with no alteration of their natural characteristics," *J. Gene Med.*, 10:762-769 (2008).

Smith, C L et al., "Immunodominance of poxviral-specific CTL in a human trial of recombinant-modified vaccinia Ankara," *J. Immunol.*, 175:8431-8437 (2005).

Srivastava, A "Adeno-associated virus-mediated gene transfer," *J. Cell Biochem.*, 105:17-24 (2008).

Tacken, P J et al., "Dendritic-cell immunotherapy: from ex vivo loading to in vivo targeting," *Nat. Rev. Immunol.*, 7:790-802 (2007).

Ussher, J E and Taylor, J A, "Optimized transduction of human monocyte-derived dendritic cells by recombinant adeno-associated virus serotype 6," *Hum. Gene Ther.*, 21:1675-1686 (2010).

Vandenberghe, L H et al., "Tailoring the AAV vector capsid for gene therapy," *Gene Ther.*, 16:311-319 (2009).

Veron, P et al., "Major subsets of human dendritic cells are efficiently transduced by self-complementary adeno-associated virus vectors 1 and 2," *J. Virol.*, 81:5385-5394 (2007).

Wang, W and Malcolm, B A, "Two-stage PCR protocol allowing introduction of multiple mutations, deletions and insertions using QuikChange site-directed mutagenesis," *BioTechniques*, 26:680-682 (1999).

Wang, Z et al., "Rapid and highly efficient transduction by double-stranded adeno-associated virus vectors in vitro and in vivo," *Gene Ther.*, 10:2105-2111 (2003).

Wu, P et al., "Mutational analysis of the adeno-associated virus type 2 (AAV2) capsid gene and construction of AAV2 vectors with altered tropism," *J. Virol.*, 74:8635-8647 (2000).

Wu, Z et al., "Adeno-associated virus serotypes: vector toolkit for human gene therapy," *Mol. Ther.*, 14:316-327 (2006).

Wu, Z et al., "Single amino acid changes can influence titer, heparin binding, and tissue tropism in different adeno-associated virus serotypes," *J. Virol.*, 80:11393-11397 (2006).

Xie, Q et al., "The atomic structure of adeno-associated virus (AAV-2), a vector for human gene therapy," *Proc. Nat'l. Acad. Sci. USA*, 99:10405-10410 (2002).

Yu, Y et al., "rAAV/Her-2/neu loading of dendritic cells for a potent cellular-mediated MHC class I restricted immune response against ovarian cancer." *Viral Immunol.*, 21:435-442 (2008).

Zhong, L et al., "A dual role of EGFR protein tyrosine kinase signaling in ubiquitination of AAV2 capsids and viral second-strand DNA synthesis," *Mol. Ther.*, 15:1323-1330 (2007).

Zhong, L et al., "Next generation of adeno-associated virus 2 vectors: Point mutations in tyrosines lead to high-efficiency transduction at lower doses," *Proc. Nat'l. Acad. Sci. USA*, 105:7827-7832 (2008).

Zhong, L et al., "Tyrosine-phosphorylation of AAV2 vectors and its consequences on viral intracellular trafficking and transgene expression," *Virology*, 381:194-202 (2008).

Zolotukhin, S et al., "Production and purification of serotype 1, 2, and 5 recombinant adeno-associated viral vectors," *Methods (San Diego, CA)*, 28:158-167 (2002).

It should be understood that the examples and embodiments described herein are for illustrative purposes only and that various modifications or changes in light thereof will be suggested to persons skilled in the art and are to be included within the spirit and purview of this application and the scope of the appended claims.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An AAV VP3 protein comprising a non-native, non-threonine amino acid residue at a position corresponding to T491 of the wild-type AAV2 capsid protein set forth in SEQ ID NO: 2, and:
   (i) a non-native, non-serine amino acid residue at a position corresponding to S662 of the wild-type AAV2 capsid protein set forth in SEQ ID NO: 2;
   (ii) a non-native, non-serine amino acid residue at a position corresponding to S662 and a non-native, non-tyrosine amino acid residue at a position corresponding to Y730 of the wild-type AAV2 capsid protein set forth in SEQ ID NO: 2;
   (iii) a non-native, non-tyrosine amino acid residue at a position corresponding to Y730 of the wild-type AAV2 capsid protein set forth in SEQ ID NO: 2;
   (iv) a non-native, non-tyrosine amino acid residue at a position corresponding to Y444 of the wild-type AAV2 capsid protein set forth in SEQ ID NO: 2;
   (v) non-native, non-tyrosine amino acid residues at positions corresponding to Y444 and Y730 of the wild-type AAV2 capsid protein set forth in SEQ ID NO: 2;
   (vi) non-native, non-tyrosine amino acid residues at positions corresponding to Y444, Y500, and Y730 of the wild-type AAV2 capsid protein set forth in SEQ ID NO: 2; and/or
   (vii) non-native, non-tyrosine amino acid residues at positions corresponding to Y272, Y444, Y500, and Y730 of the wild-type AAV2 capsid protein set forth in SEQ ID NO: 2;
   wherein the non-native, non-threonine amino acid residue is not alanine.

2. The AAV VP3 protein of claim 1, comprising the non-native, non-threonine amino acid residue at a position corresponding to T491 and the non-native, non-serine amino acid residue at a position corresponding to S662 of the wild-type AAV2 capsid protein set forth in SEQ ID NO: 2, and
   wherein non-native, non-threonine amino acid residue is valine; and the non-native, non-serine amino acid residue is valine.

3. The AAV VP3 protein of claim 1, comprising the non-native, non-threonine amino acid residue at a position corresponding to T491, the non-native, non-serine amino acid residue at a position corresponding to S662, and the non-native, non-tyrosine amino acid residue at a position corresponding to Y730 of the wild-type AAV2 capsid protein set forth in SEQ ID NO: 2, an
   wherein non-native, non-threonine amino acid residue is valine; the non-native, non-serine amino acid residue is valine; and the non-native, non-tyrosine amino acid residue is phenylalanine.

4. The AAV VP3 protein of claim 1, comprising the non-native, non-threonine amino acid residue at a position corresponding to T491 and the non-native, non-tyrosine amino acid residue at a position corresponding to Y730 of the wild-type AAV2 capsid protein set forth in SEQ ID NO: 2, and
   wherein non-native, non-threonine amino acid residue is valine; and the non-native, non-tyrosine amino acid residue is phenylalanine.

5. The AAV VP3 protein of claim 1, comprising the non-native, non-threonine amino acid residue at a position corresponding to T491 and the non-native, non-tyrosine amino acid residue at a position corresponding to Y444 of the wild-type AAV2 capsid protein set forth in SEQ ID NO: 2, and
   wherein non-native, non-threonine amino acid residue is valine; and the non-native, non-tyrosine amino acid residue is phenylalanine.

6. The AAV VP3 protein of claim 1, comprising the non-native, non-threonine amino acid residue at a position corresponding to T491 and the non-native, non-tyrosine amino acid residues at positions corresponding to Y444 and Y730 of the wild-type AAV2 capsid protein set forth in SEQ ID NO: 2, and
   wherein non-native, non-threonine amino acid residue is valine; and the non-native, non-tyrosine amino acid residues are phenylalanine.

7. The AAV VP3 protein of claim 1, comprising the non-native, non-threonine amino acid residue at a position corresponding to T491 and the non-native, non-tyrosine amino acid residues at positions corresponding to Y444, Y500, and Y730 of the wild-type AAV2 capsid protein set forth in SEQ ID NO: 2, and
   wherein non-native, non-threonine amino acid residue is valine, and the non-native, non-tyrosine amino acid residues are phenylalanine.

8. The AAV VP3 protein of claim 1, comprising the non-native, non-threonine amino acid residue at a position corresponding to T491 and the non-native, non-tyrosine amino acid residues at positions corresponding to Y272, Y444, Y500, and Y730 of the wild-type AAV2 capsid protein set forth in SEQ ID NO: 2, and wherein non-native, non-threonine amino acid residue is valine, and the non-native, non-tyrosine amino acid residues are phenylalanine.

9. The AAV VP3 protein of claim 1, wherein the AAV VP3 protein is an AAV1, AAV2, AAV3, AAV4, AAV5, AAV6, AAV7, AAV8, AAV9, AAV10, AAV11, or AAV12 serotype VP3 protein.

10. An isolated nucleic acid molecule that encodes the AAV VP3 protein of claim 1.

11. A recombinant AAV (rAAV) particle comprising the AAV VP3 protein of claim 1 and a nucleic acid segment comprising a sequence that encodes a therapeutic agent and/or a diagnostic agent.

12. The rAAV particle of claim 11, wherein the nucleic acid segment further comprises a promoter and/or an enhancer operably linked to the sequence that encodes the therapeutic agent and/or the diagnostic agent.

13. The rAAV particle of claim 12, wherein the promoter is a heterologous promoter, a tissue-specific promoter, a constitutive promoter, an inducible promoter, or any combination thereof.

14. The rAAV particle of claim 12, wherein the promoter is a cytomegalovirus (CMV) promoter, a desmin (DES) promoter, a beta-actin promoter, an insulin promoter, an enolase promoter, a BDNF promoter, an NGF promoter, an EGF promoter, a growth factor promoter, an axon-specific promoter, a dendrite-specific promoter, a brain-specific promoter, a hippocampal-specific promoter, a kidney-specific promoter, an elafin promoter, a cytokine promoter, an interferon promoter, a growth factor promoter, an alpha-1 antitrypsin promoter, a neural cell-specific promoter, a central nervous system cell-specific promoter, a peripheral nervous system cell-specific promoter, an interleukin promoter, a serpin promoter, a hybrid CMV promoter, a hybrid beta-actin promoter, an EF1 promoter, a U1a promoter, a U1b promoter, a Tet-inducible promoter, or a VP16-LexA promoter; and/or wherein the enhancer is a CMV enhancer, a synthetic enhancer, a liver-specific enhancer, a vascular-specific enhancer, a brain-specific enhancer, a neural cell-specific enhancer, a lung-specific enhancer, a muscle-specific enhancer, a kidney-specific enhancer, a pancreas-specific enhancer, or an islet cell-specific enhancer.

15. The rAAV particle of claim 12, wherein the therapeutic agent and/or the diagnostic agent comprises an adrenergic agonist, an anti-apoptosis factor, an apoptosis inhibitor, a cytokine receptor, a cytokine, a cytotoxin, an erythropoietic agent, a glutamic acid decarboxylase, a glycoprotein, a growth factor, a growth factor receptor, a hormone, a hormone receptor, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neuropilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinase inhibitor, a proteolytic protein, a proteolytic protein inhibitor, a semaphorin, a semaphorin receptor, a serotonin transport protein, a serotonin uptake inhibitor, a serotonin receptor, a serpin, a serpin receptor, a tumor suppressor, BDNF, CNTF, CSF, EGF, FGF, G-SCF, GM-CSF, gonadotropin, IFN, IFG-1, M-CSF, NGF, PDGF, PEDF, TGF, TGF-B2, TNF, VEGF, prolactin, somatotropin, XIAP1, IL-1, IL-2, IL-3, IL-4, IL-5, IL-6, IL-7, IL-8, IL-9, IL-10, IL-10(187A), viral IL-10, IL-11, IL-12, IL-13, IL-14, IL-15, IL-16, IL-17, or IL-18.

16. The rAAV particle of claim 11, wherein the rAAV particle is an AAV1, AAV2, AAV3, AAV4, AAV5, AAV6, AAV7, AAV8, AAV9, AAV10, AAV11, or AAV 12 serotype particle.

17. A method of transducing a cell, tissue, and/or organ of interest, the method comprising contacting the cell, tissue, and/or organ of interest with a composition comprising an effective amount of the rAAV particle of claim 11.

18. The method of claim 17, wherein the cell, tissue, and/or organ of interest comprises an endothelial, epithelial, vascular, liver, lung, heart, pancreas, intestinal, kidney, muscle, bone, dendritic, cardiac, neural, blood, brain, fibroblast and/or cancer cell.

19. A method of treating or ameliorating a symptom of a disease, injury, disorder, or dysfunction in a subject, the method comprising administering to the subject a composition comprising an effective amount of the rAAV particle of claim 11, thereby treating or ameliorating the symptom of the disease, injury, disorder, or dysfunction in the subject.

20. The method of claim 19, wherein the administering comprises intracerebro-ventricular administration, subarachnoid administration, intraspinal administration, epidural administration, intrasternal administration, intramuscular administration, intravenous administration, subcutaneous administration, intrathecal administration, intraperitoneal administration, pulmonary administration, intranasal administration, oral administration, administration by inhalation, transdermal administration, intradermal administration, transmucosal administration, intraorbital administration, intracardiac administration, transtracheal administration, subcuticular administration, intraarticular administration, subcapsular administration, or administration by direct injection into an organ or a tissue of the subject.

21. The method of claim 19, wherein the disease, injury, disorder, or dysfunction comprises Alzheimer's disease; Huntington's disease; Tay-Sach's disease; Parkinson's disease; memory loss; trauma; motor impairment; neuropathy; arthritis; palsy; cystic fibrosis (CF); a neural disease; amyotrophic lateral sclerosis (ALS); multiple sclerosis (MS); muscular dystrophy (MD); a peptide or polypeptide deficiency; a peptide or polypeptide overexpression; a musculoskeletal or neuromuscular disease; a cancer, tumor, or other malignant growth; a neurological deficit dysfunction; an autoimmune disease; an articular disease; a cardiac or pulmonary disease; ischemia; stroke; cerebrovascular accidents; transient ischemic attacks (TIA); diabetes or other disease of the pancreas; cardiocirculatory disease or dysfunction; hypotension; hypertension; atherosclerosis; hypercholesterolemia; vascular damage or disease; or a biliary, renal or hepatic disease or dysfunction.

* * * * *

SEQUENCE LISTING

```
Sequence total quantity: 12
SEQ ID NO: 1            moltype = AA  length = 736
FEATURE                 Location/Qualifiers
source                  1..736
                        mol_type = protein
                        note = adeno-associated virus 1
                        organism = unidentified
SEQUENCE: 1
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPFPADV FMIPQYGYLT LNNGSQAVGR SSFYCLEYFP SQMLRTGNNF TFSYTFEEVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD EDKFFPMSGV  540
MIFGKESAGA SNTALDNVMI TDEEEIKATN PVATERFGTV AVNFQSSSTD PATGDVHAMG  600
ALPGMVWQDR DVYLQGPIWA KIPHTDGHFH PSPLMGGFGL KNPPPQILIK NTPVPANPPA  660
EFSATKFASF ITQYSTGQVS VEIEWELQKE NSKRWNPEVQ YTSNYAKSAN VDFTVDNNGL  720
YTEPRPIGTR YLTRPL                                                 736

SEQ ID NO: 2            moltype = AA  length = 735
FEATURE                 Location/Qualifiers
source                  1..735
                        mol_type = protein
                        note = adeno-associated virus 2
                        organism = unidentified
SEQUENCE: 2
MAADGYLPDW LEDTLSEGIR QWWKLKPGPP PPKPAERHKD DSRGLVLPGY KYLGPFNGLD   60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFQ FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNRQA ATADVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRY LTRNL                                                  735

SEQ ID NO: 3            moltype = AA  length = 736
FEATURE                 Location/Qualifiers
source                  1..736
                        mol_type = protein
```

```
                        note = adeno-associated virus 3
                        organism = unidentified
SEQUENCE: 3
MAADGYLPDW LEDNLSEGIR EWWALKPGVP QPKANQQHQD NRRGLVLPGY KYLGPGNGLD   60
KGEPVNEADA AALEHDKAYD QQLKAGDNPY LKYNHADAEF QERLQEDTSF GGNLGRAVFQ  120
AKKRILEPLG LVEEAAKTAP GKKGAVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGASNDN HYFGYSTPWG YFDFNRFHCH FSPRDWQRLI  300
NNNWGFRPKK LSFKLFNIQV RGVTQNDGTT TIANNLTSTV QVFTDSEYQL PYVLGSAHQG  360
CLPPFPADVF MVPQYGYLTL NNGSQAVGRS SFYCLEYFPS QMLRTGNNFQ FSYTFEDVPF  420
HSSYAHSQSL DRLMNPLIDQ YLYYLNRTQG TTSGTTNQSR LLFSQAGPQS MSLQARNWLP  480
GPCYRQQRLS KTANDNNNSN FPWTAASKYH LNGRDSLVNP GPAMASHKDD EEKFFPMHGN  540
LIFGKEGTTA SNAELDNVMI TDEEEIRTTN PVATEQYGTV ANNLQSSNTA PTTGTVNHQG  600
ALPGMVWQDR DVYLQGPIWA KIPHTDGHFH PSPLMGGFGL KHPPPQIMIK NTPVPANPPT  660
TFSPAKFASF ITQYSTGQVS VEIEWELQKE NSKRWNPEIQ YTSNYNKSVN VDFTVDTNGV  720
YSEPRPIGTR YLTRNL                                                  736

SEQ ID NO: 4           moltype = AA   length = 734
FEATURE                Location/Qualifiers
source                 1..734
                        mol_type = protein
                        note = adeno-associated virus 4
                        organism = unidentified
SEQUENCE: 4
MTDGYLPDWL EDNLSEGVRE WWALQPGAPK PKANQQHQDN ARGLVLPGYK YLGPGNGLDK   60
GEPVNAADAA ALEHDKAYDQ QLKAGDNPYL KYNHADAEFQ QRLQGDTSFG GNLGRAVFQA  120
KKRVLEPLGL VEQAGETAPG KKRPLIESPQ QPDSSTGIGK KGKQPAKKKL VFEDETGAGD  180
GPPEGSTSGA MSDDSEMRAA AGGAAVEGGQ GADGVGNASG DWHCDSTWSE GHVTTTSTRT  240
WVLPTYNNHL YKRLGESLQS NTYNGFSTPW GYFDFNRFHC HFSPRDWQRL INNNWGMRPK  300
AMRVKIFNIQ VKEVTTSNGE TTVANNLTST VQIFADSSYE LPYVMDAGQE GSLPPFPNDV  360
FMVPQYGYCG LVTGNTSQQQ TDRNAFYCLE YFPSQMLRTG NNFEITYSFE KVPFHSMYAH  420
SQSLDRLMNP LIDQYLWGLQ STTTGTTLNA GTATTNFTKL RPTNFSNPKK NWLPGPSIKQ  480
QGFSKTANQN YKIPATGSDS LIKYETHSTL DGRWSALTPG PPMATAGPAD SKFSNSQLIF  540
AGPKQNGNTA TVPGTLIFTS EEELAATNAT DTDMWGNLPG GDQSNSNLPT VDRLTALGAV  600
PGMVWQNRDI YYQGPIWAKI PHTDGHFHPS PLIGGFGLKH PPPQIFIKNT PVPANPATTF  660
SSTPVNSFIT QYSTGQVSVQ IDWEIQKERS KRWNPEVQFT SNYGQQNSLL WAPDAAGKYT  720
EPRAIGTRYL THHL                                                    734

SEQ ID NO: 5           moltype = AA   length = 724
FEATURE                Location/Qualifiers
source                 1..724
                        mol_type = protein
                        note = adeno-associated virus 5
                        organism = unidentified
SEQUENCE: 5
MSFVDHPPDW LEEVGEGLRE FLGLEAGPPK PKPNQQHQDQ ARGLVLPGYN YLGPGNGLDR   60
GEPVNRADEV AREHDISYNE QLEAGDNPYL KYNHADAEFQ EKLADDTSFG GNLGRAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSTWMGDRVV TKSTRTWVLP  240
SYNNHQYREI KSGSVDGSNA NAYFGYSTPW GYFDFNRFHS HWSPRDWQRL INNYWGFRPR  300
SLRVKIFNIQ VKEVTVQDST TIANNLTSTV QVFTDDDYQ LPYVVGNGTE GCLPAFPPQV  360
FTLPQYGYAT LNRDNTENPT ERSSFFCLEY FPSKMLRTGN NFEFTYNFEE VPFHSSFAPS  420
QNLFKLANPL VDQYLYRFVS TNNTGGVQFN KNLAGRYANT YKNWFPGPMG RTQGWNLGSG  480
VNRASVSAFA TTNRMELEGA SYQVPPQPNG MTNNLQGSNT YALENTMIFN SQPANPGTTA  540
TYLENGNMLIT SESETQPVNR VAYNVGGQMA TNNQSSTTAP ATGTYNLQEI VPGSVWMERD  600
VYLQGPIWAK IPETGAHFHP SPAMGGFGLK HPPPMMLIKN TPVPGNITSF SDVPVSSFIT  660
QYSTGQVTVE MEWELKKENS KRWNPEIQYT NNYNDPQFVD FAPDSTGEYR TTRPIGTRYL  720
TRPL                                                               724

SEQ ID NO: 6           moltype = AA   length = 736
FEATURE                Location/Qualifiers
source                 1..736
                        mol_type = protein
                        note = adeno-associated virus 6
                        organism = unidentified
SEQUENCE: 6
MAADGYLPDW LEDNLSEGIR EWWDLKPGAP KPKANQQKQD DGRGLVLPGY KYLGPFNGLD   60
KGEPVNEADA AALEHDKAYD QQLKAGDNPY LRYNHADAEF QERLQEDTSF GGNLGRAVFQ  120
AKKRVLEPFG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPFPADV FMIPQYGYLT LNNGSQAVGR SSFYCLEYFP SQMLRTGNNF TFSYTFEDVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD KDKFFPMSGV  540
MIFGKESAGA SNTALDNVMI TDEEEIKATN PVATERFGTV AVNLQSSSTD PATGDVHVMG  600
ALPGMVWQDR DVYLQGPIWA KIPHTDGHFH PSPLMGGFGL KHPPPQILIK NTPVPANPPA  660
EFSATKFASF ITQYSTGQVS VEIEWELQKE NSKRWNPEVQ YTSNYAKSAN VDFTVDNNGL  720
YTEPRPIGTR YLTRPL                                                  736
```

```
SEQ ID NO: 7               moltype = AA   length = 737
FEATURE                    Location/Qualifiers
source                     1..737
                           mol_type = protein
                           note = adeno-associated virus 7
                           organism = unidentified
SEQUENCE: 7
MAADGYLPDW LEDNLSEGIR EWWDLKPGAP KPKANQQKQD NGRGLVLPGY KYLGPFNGLD  60
KGEPVNAADA AALEHDKAYD QQLKAGDNPY LRYNHADAEF QERLQEDTSF GGNLGRAVFQ 120
AKKRVLEPLG LVEEGAKTAP AKKRPVEPSP QRSPDSSTGI GKKGQQPARK RLNFGQTGDS 180
ESVPDPQPLG EPPAAPSSVG SGTVAAGGGA PMADNNEGAD GVGNASGNWH CDSTWLGDRV 240
ITTSTRTWAL PTYNNHLYKQ ISSETAGSTN DNTYFGYSTP WGYFDFNRFH CHFSPRDWQR 300
LINNNWGFRP KKLRFKLFNI QVKEVTTNDG VTTIANNLTS TIQVFSDSEY QLPYVLGSAH 360
QGCLPPFPAD VFMIPQYGYL TLNNGSQSVG RSSFYCLEYF PSQMLRTGNN FEFSYSFEDV 420
PFHSSYAHSQ SLDRLMNPLI DQYLYYLART QSNPGGTAGN RELQFYQGGP STMAEQAKNW 480
LPGPCFRQQR VSKTLDQNNN SNFAWTGATK YHLNGRNSLV NPGVAMATHK DDEDRFFPSS 540
GVLIFGKTGA TNKTTLENVL MTNEEEIRPT NPVATEEYGI VSSNLQAANT AAQTQVVNNQ 600
GALPGMVWQN RDVYLQGPIW AKIPHTDGNF HPSPLMGGFG LKHPPPQILI KNTPVPANPP 660
EVFTPAKFAS FITQYSTGQV SVEIEWELQK ENSKRWNPEI QYTSNFEKQT GVDFAVDSQG 720
VYSEPRPIGT RYLTRNL                                               737

SEQ ID NO: 8               moltype = AA   length = 738
FEATURE                    Location/Qualifiers
source                     1..738
                           mol_type = protein
                           note = adeno-associated virus 8
                           organism = unidentified
SEQUENCE: 8
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ 120
AKKRVLEPLG LVEEGAKTAP GKKRPVEPSP QRSPDSSTGI GKKGQQPARK RLNFGQTGDS 180
ESVPDPQPLG EPPAAPSGVG PNTMAAGGGA PMADNNEGAD GVGSSSGNWH CDSTWLGDRV 240
ITTSTRTWAL PTYNNHLYKQ ISNGTSGGAT NDNTYFGYST PWGYFDFNRF HCHFSPRDWQ 300
RLINNNWGFR PKRLSFKLFN IQVKEVTQNE GTKTIANNLT STIQVFTDSE YQLPYVLGSA 360
HQGCLPPFPA DVFMIPQYGY LTLNNGSQAV GRSSFYCLEY FPSQMLRTGN NFQFTYTFED 420
VPFHSSYAHS QSLDRLMNPL IDQYLYYLSR TQTTGGTANT QTLGFSQGGP NTMANQAKNW 480
LPGPCYRQQR VSTTTGQNNN SNFAWTAGTK YHLNGRNSLA NPGIAMATHK DDEERFFPSN 540
GILIFGKQNA ARDNADYSDV MLTSEEEIKT TNPVATEEYG IVADNLQQQN TAPQIGTVNS 600
QGALPGMVWQ NRDVYLQGPI WAKIPHTDGN FHPSPLMGGF GLKHPPPQIL IKNTPVPADP 660
PTTFNQSKLN SFITQYSTGQ VSVEIEWELQ KENSKRWNPE IQYTSNYYKS TSVDFAVNTE 720
GVYSEPRPIG TRYLTRNL                                              738

SEQ ID NO: 9               moltype = AA   length = 736
FEATURE                    Location/Qualifiers
source                     1..736
                           mol_type = protein
                           note = adeno-associated virus 9
                           organism = unidentified
SEQUENCE: 9
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ 120
AKKRLLEPLG LVEEAAKTAP GKKRPVEQSP QEPDSSAGIG KSGAQPAKKR LNFGQTGDTE 180
SVPDPQPIGE PPAAPSGVGS LTMASGGGAP VADNNEGADG VGSSSGNWHC DSQWLGDRVI 240
TTSTRTWALP TYNNHLYKQI SNSTSGGSSN DNAYFGYSTP WGYFDFNRFH CHFSPRDWQR 300
LINNNWGFRP KRLNFKLFNI QVKEVTDNNG VKTIANNLTS TVQVFTDSDY QLPYVLGSAH 360
EGCLPPFPAD VFMIPQYGYL TLNDGSQAVG RSSFYCLEYF PSQMLRTGNN FQFSYEFENV 420
PFHSSYAHSQ SLDRLMNPLI DQYLYYLSKT INGSGQNQQT LKFSVAGPSN MAVQGRNYIP 480
GPSYRQQRVS TTVTQNNNSE FAWPGASSWA LNGRNSLMNP GPAMASHKEG EDRFFPLSGS 540
LIFGKQGTGR DNVDADKVMI TNEEEIKTTN PVATESYGQV ATNHQSAQAQ AQTGWVQNQG 600
ILPGMVWQDR DVYLQGPIWA KIPHTDGNFH PSPLMGGFGM KHPPPQILIK NTPVPADPPT 660
AFNKDKLNSF ITQYSTGQVS VEIEWELQKE NSKRWNPEIQ YTSNYYKSNN VEFAVNTEGV 720
YSEPRPIGTR YLTRNL                                                736

SEQ ID NO: 10              moltype = AA   length = 738
FEATURE                    Location/Qualifiers
source                     1..738
                           mol_type = protein
                           note = adeno-associated virus 10
                           organism = unidentified
SEQUENCE: 10
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ 120
AKKRVLEPLG LVEEGAKTAP GKKRPVEPSP QRSPDSSTGI GKKGQQPAKK RLNFGQTGDS 180
ESVPDPQPIG EPPAGPSGLG SGTMAAGGGA PMADNNEGAD GVGSSSGNWH CDSTWLGDRV 240
ITTSTRTWAL PTYNNHLYKQ ISNGTSGGST NDNTYFGYST PWGYFDFNRF HCHFSPRDWQ 300
RLINNNWGFR PKRLNFKLFN IQVKEVTQNE GTKTIANNLT STIQVFTDSE YQLPYVLGSA 360
HQGCLPPFPA DVFMIPQYGY LTLNNGSQAV GRSSFYCLEY FPSQMLRTGN NFEFSYQFED 420
VPFHSSYAHS QSLDRLMNPL IDQYLYYLSR TQSTGGTAGT QQLLFSQAGP NNMSAQAKNW 480
```

```
LPGPCYRQQR VSTTLSQNNN SNFAWTGATK YHLNGRDSLV NPGVAMATHK DDEERFFPSS    540
GVLMFGKQGA GKDNVDYSSV MLTSEEEIKT TNPVATEQYG VVADNLQQQN AAPIVGAVNS    600
QGALPGMVWQ NRDVYLQGPI WAKIPHTDGN FHPSPLMGGF GLKHPPPQIL IKNTPVPADP    660
PTTFSQAKLA SFITQYSTGQ VSVEIEWELQ KENSKRWNPE IQYTSNYYKS TNVDFAVNTD    720
GTYSEPRPIG TRYLTRNL                                                  738

SEQ ID NO: 11           moltype = DNA  length = 21
FEATURE                 Location/Qualifiers
source                  1..21
                        mol_type = other DNA
                        organism = synthetic construct
SEQUENCE: 11
tcccatagta acgccaatag g                                              21

SEQ ID NO: 12           moltype = DNA  length = 23
FEATURE                 Location/Qualifiers
source                  1..23
                        mol_type = other DNA
                        organism = synthetic construct
SEQUENCE: 12
cttggcatat gatacacttg atg                                            23
```